(12) United States Patent
Long

(10) Patent No.: US 8,796,504 B2
(45) Date of Patent: *Aug. 5, 2014

(54) METHODS FOR ENHANCING THE PRODUCTION AND CONSUMER TRAITS OF PLANTS

(75) Inventor: Bryant Jerome Long, Wellington, FL (US)

(73) Assignee: ACAABCO Holdings, LLC, Boca Raton, FL (US)

( * ) Notice: Subject to any disclaimer, the term of this patent is extended or adjusted under 35 U.S.C. 154(b) by 452 days.

This patent is subject to a terminal disclaimer.

(21) Appl. No.: 12/806,472

(22) Filed: Aug. 12, 2010

(65) Prior Publication Data

US 2012/0054896 A1    Mar. 1, 2012

Related U.S. Application Data

(63) Continuation-in-part of application No. 12/462,959, filed on Aug. 12, 2009.

(51) Int. Cl.
| | |
|---|---|
| *A01H 1/04* | (2006.01) |
| *A01H 1/06* | (2006.01) |
| *A01H 5/00* | (2006.01) |
| *A01H 5/10* | (2006.01) |
| *C12P 19/02* | (2006.01) |
| *C12P 19/12* | (2006.01) |

(52) U.S. Cl.
USPC ........... 800/275; 800/263; 800/266; 800/267; 800/270; 800/320.1

(58) Field of Classification Search
None
See application file for complete search history.

(56) References Cited

U.S. PATENT DOCUMENTS

| | | | |
|---|---|---|---|
| 3,971,161 A | 7/1976 | Bonucci | 47/58 |
| 4,630,393 A | 12/1986 | Bonucci | 47/58 |
| 5,589,618 A | 12/1996 | Hannah et al. | 800/205 |
| 5,650,557 A | 7/1997 | Hannah et al. | 800/205 |
| 5,746,023 A | 5/1998 | Hanafey et al. | 800/200 |
| 5,912,413 A | 6/1999 | Myers et al. | 800/205 |
| 6,184,438 B1 * | 2/2001 | Hannah | 800/284 |
| 6,188,003 B1 * | 2/2001 | Plaisted et al. | 800/320.1 |
| 6,756,524 B2 | 6/2004 | Tanksley | 800/278 |
| 7,084,320 B2 | 8/2006 | De Block | 800/268 |
| 2003/0066110 A1 * | 4/2003 | Natti | 800/320.1 |
| 2005/0160500 A1 | 7/2005 | Castigioni et al. | 800/288 |
| 2007/0083943 A1 | 4/2007 | Hannah et al. | 800/278 |

OTHER PUBLICATIONS

Paulis et al. Theoretical and Applied Genetics 79: 314-320 (1990).*
Paulis, J.W. et al., "Expression of Alcohol-Soluble Endosperm Proteins in Maize Single and Double Mutants," Theor Appl Genet 79:314-320 (1990).
Yousef, Gad G., "Comparison of Phenotypic and Marker-Assisted Selection for Quantitative Traits in Sweet Corn," Crop Sci. 41:645-655 (2001).
Debra Levey Larson, "Supersweet Sweet Corn: 50 Years in the Making," University of Illinois at Urbana-Champaign, *Inside* Illinois, vol. 23, No. 3 (2003).
George W. Crookham, Letter dated Oct. 12, 2009 sent by Crookham Company, P.O. Box 520 Caldwell, ID 83606-0520, to Abbott & Cobb, Inc., P.O. Box 307, Feasterville, PA 19053-0307.
International Searching Authority, International Search Report and a Written Opinion of International Patent Application No. PCT/US10/02212, filed internationally on Aug. 6, 2010.

\* cited by examiner

*Primary Examiner* — David T Fox
(74) *Attorney, Agent, or Firm* — Roberta L. Hastreiter; Keith D. Parr; Locke Lord LLP

(57) ABSTRACT

The invention provides methods for producing plants, plant materials and seeds that have multiple desirable attributes for consumers of these products, as well as for commercial plant growers, and to improved plants, plant materials and seeds that are produced by these methods. These inventive methods provide hybrid plants, plant materials and seeds having the mutant shrunken-2i (sh2-i) allele incorporated into their genomes, preferably sequentially along with one or more other mutant alleles, such as the sugary-1 (su1), sugary enhancer-1 (se1) and/or shrunken-2 (sh2) alleles, and that have multiple beneficial traits, including an extended sugar retention ability at the post prime eating stage and a significantly enhanced vigor and fitness to the plant, plant material and/or seed during seed germination, seedling emergence from soil, and plant development.

81 Claims, 34 Drawing Sheets

Percent Endosperm Sucrose (Dry Weight Basis)
for the SU1, SE1 and SH2 Genetic Types at the Prime Eating Stage Representative Changes in Percent Endosperm Sucrose (Dry Weight Basis) for the SU1, SE1 and SH2 Genetic Types over Seven Days at Room Temperature at the Prime Eating Stage Percent Pericarp (Dry Weight Basis) for the
SU1, SE1 and SH2 Genetic Types at the Prime Eating Stage Representative Changes in Percent Pericarp (Dry Weight Basis)
for the SU1, SE1 and SH2 Genetic Types over Seven Days
at Room Temperature at the Prime Eating Stage The Sh2 Gene Organoleptic Averages for Starch Accumulation for the
Conventional Hybrid sh2 NILs either Containing, or not Containing, SH2-i
in the Seven Days Following the Prime Eating Stage at 75% Moisture Organoleptic Averages for Sweetness for the Varieties Beyond, Passion and ACX SS 7501Y in the Seven Days Following the Prime Eating Stage at 75% Moisture Organoleptic Averages for Pericarp Tenderness for the Varieties Beyond, Passion and ACX SS 7501Y in the Seven Days Following the Prime Eating Stage at 75% Moisture Diagram of the Genomic Sequence Bearing the Splice Site Alterations of the Mutant Shrunken-2i (sh2-i) Allele

FIG. 10A

Molecular Map of Samples of Individual Inbred NILs

| sample No | sample | su1 | se | phi056 | phi056 | A-1<br>1<br>27<br>Phi427913 | A-1<br>1<br>27<br>Phi427913 | A-1<br>1<br>72<br>Phi339017 | A-1<br>1<br>72<br>Phi339017 | A-1<br>1<br>174<br>phi423298 | A-1<br>1<br>174<br>phi423298 | A-1<br>1<br>179<br>phi323065 | A-1<br>1<br>179<br>phi323065 | A-1<br>1<br>181<br>phi335539 | A-1<br>1<br>181<br>phi335539 |
|---|---|---|---|---|---|---|---|---|---|---|---|---|---|---|---|
| 2005 IBM neigbors chr. | | | | 1 | 1 | 1 | 1 | 1 | 1 | 1 | 1 | 1 | 1 | 1 | 1 |
| 2005 IBM neigbors position | | | | 2.5 | 2.5 | 27 | 27 | 72 | 72 | 174 | 174 | 179 | 179 | 181 | 181 |
| 1 | 017 | n | n | 249 | 249 | 133 | 133 | 145 | 145 | 134 | 134 | . | . | 87 | 87 |
| 2 | 044 | n | n | 249 | 249 | 133 | 133 | 145 | 145 | 134 | 134 | . | . | 87 | 87 |
| 3 | 006 | n | p | 249 | 249 | 133 | 133 | 145 | 145 | 134 | 134 | . | . | 87 | 87 |
| 4 | 007 | n | p | 249 | 249 | 133 | 133 | 145 | 145 | 134 | 134 | . | . | 87 | 87 |
| 5 | 009 | n | p | 249 | 249 | 133 | 133 | 145 | 145 | 134 | 134 | . | . | 87 | 87 |
| 6 | 047 | n | p | 249 | 249 | 130 | 130 | 145 | 145 | 134 | 134 | . | . | 87 | 87 |
| 7 | 637 | n | p | 249 | 249 | 130 | 130 | 145 | 145 | 134 | 134 | . | . | 87 | 87 |
| 8 | 001 | p | n | 249 | 249 | 130 | 130 | 145 | 145 | 134 | 134 | . | . | 87 | 87 |
| 9 | 046 | p | n | 249 | 249 | 130 | 130 | 145 | 145 | 134 | 134 | . | . | 87 | 87 |
| 10 | 048 | p | n | 249 | 249 | 130 | 130 | 145 | 145 | 134 | 134 | . | . | 87 | 87 |
| 11 | 049 | p | n | 249 | 249 | 130 | 130 | 145 | 145 | 134 | 134 | . | . | 87 | 87 |
| 12 | 109 | p | n | 249 | 249 | 130 | 130 | 145 | 145 | 134 | 134 | . | . | 87 | 87 |
| 13 | 354 | p | n | 249 | 249 | 130 | 130 | 145 | 145 | 134 | 134 | . | . | 87 | 87 |
| 14 | sh2-i | n | n | 249 | 249 | 130 | 130 | 148 | 148 | 129 | 129 | 329 | 329 | 90 | 90 |

FIG. 10B

| 2005 IBM neigbors | chr. | | | 1 | 1 | 1 | 1 | 1 | 1 | 1 | 1 | 1 | 1 | 1 | 1 |
|---|---|---|---|---|---|---|---|---|---|---|---|---|---|---|---|
| 2005 IBM neigbors | position | | | 290 | 290 | 721 | 721 | 839 | 839 | 927 | 927 | 973 | 973 | 1097.4 | 1097.4 |
| sample No | sample | su1 | se | Phi109275 | Phi109275 | phi002 | phi002 | phi011 | phi011 | phi308707 | phi308707 | Phi265454 | Phi265454 | phi227562 | phi227562 |
| 1 | 017 | n | n | 125 | 125 | 72 | 72 | 214 | 214 | 129 | 129 | 218 | 218 | 307 | 307 |
| 2 | 044 | n | n | 125 | 125 | 72 | 72 | 218 | 218 | 129 | 129 | 218 | 218 | 307 | 307 |
| 3 | 006 | n | p | 125 | 125 | 68 | 68 | 218 | 218 | 132 | 132 | 229 | 229 | 307 | 307 |
| 4 | 007 | n | p | 125 | 125 | 68 | 68 | 218 | 218 | 129 | 129 | 229 | 229 | 307 | 307 |
| 5 | 009 | n | p | 125 | 125 | 72 | 72 | 218 | 218 | 117 | 117 | 218 | 218 | 307 | 307 |
| 6 | 047 | n | p | 125 | 125 | 68 | 68 | 218 | 218 | 117 | 117 | 218 | 218 | 307 | 307 |
| 7 | 637 | n | p | 125 | 125 | 72 | 72 | 218 | 218 | 117 | 129 | 218 | 218 | 307 | 307 |
| 8 | 001 | p | n | 125 | 125 | 68 | 68 | 218 | 218 | 117 | 117 | 218 | 218 | 307 | 307 |
| 9 | 046 | p | n | 125 | 125 | 72 | 72 | 218 | 218 | 117 | 117 | 218 | 218 | 307 | 307 |
| 10 | 048 | p | n | 125 | 125 | 68 | 72 | 218 | 218 | 117 | 117 | 218 | 218 | 307 | 307 |
| 11 | 049 | p | n | 125 | 125 | 72 | 72 | 218 | 218 | 129 | 129 | 218 | 218 | 307 | 307 |
| 12 | 109 | p | n | 125 | 125 | 72 | 72 | 218 | 218 | 117 | 117 | 218 | 218 | 307 | 307 |
| 13 | 354 | p | n | 125 | 125 | 68 | 68 | 218 | 218 | 117 | 117 | 218 | 218 | 307 | 307 |
| 14 | sh2-i | n | n | 125 | 125 | 72 | 72 | 218 | 218 | 129 | 129 | 201 | 201 | 313 | 313 |

FIG. 10C

| 2005 IBM neigbors | chr. | | | 1 | 1 | A-2 | | | | A-2 | | A-2 | | | |
|---|---|---|---|---|---|---|---|---|---|---|---|---|---|---|---|
| | | | | | | 2 | 2 | 2 | 2 | 2 | 2 | 2 | 2 | 2 | 2 |
| 2005 IBM neigbors | position | | | 1103 | 1103 | 0 | 0 | 28 | 28 | 125 | 125 | 145 | 145 | 285 | 285 |
| sample No | sample | su1 | se | phi064 | phi064 | Phi402893 | Phi402893 | phi96100 | phi96100 | phi127 | phi127 | phi328189 | phi328189 | phi083 | phi083 |
| 1 | 017 | n | n | 73 | 73 | 212 | 212 | 294 | 294 | 122 | 122 | . | . | 124 | 124 |
| 2 | 044 | n | n | 73 | 73 | 212 | 212 | 294 | 294 | 122 | 122 | . | . | 124 | 124 |
| 3 | 006 | n | p | 73 | 73 | 212 | 212 | 294 | 294 | 122 | 122 | . | . | 129 | 129 |
| 4 | 007 | n | p | 100 | 100 | 212 | 212 | 294 | 294 | 124 | 124 | . | . | 129 | 129 |
| 5 | 009 | n | p | 100 | 100 | 212 | 212 | 294 | 294 | 122 | 122 | . | . | 124 | 124 |
| 6 | 047 | n | p | 73 | 73 | 212 | 212 | 294 | 294 | 124 | 124 | . | . | 124 | 124 |
| 7 | 637 | n | p | 73 | 73 | 212 | 212 | 294 | 294 | 124 | 124 | . | . | 124 | 124 |
| 8 | 001 | p | n | 73 | 73 | 212 | 212 | 294 | 294 | 124 | 124 | . | . | 124 | 124 |
| 9 | 046 | p | n | 73 | 73 | 212 | 212 | 294 | 294 | 124 | 124 | . | . | 124 | 124 |
| 10 | 048 | p | n | 100 | 100 | 212 | 212 | 294 | 294 | 124 | 124 | . | . | 124 | 124 |
| 11 | 049 | p | n | 73 | 73 | 212 | 212 | 294 | 294 | 124 | 124 | . | . | 124 | 124 |
| 12 | 109 | p | n | 100 | 100 | 212 | 212 | 294 | 294 | 124 | 124 | . | . | 129 | 129 |
| 13 | 354 | p | n | 73 | 73 | 212 | 212 | 294 | 294 | 124 | 124 | . | . | 124 | 124 |
| 14 | sh2-i | n | n | 73 | 73 | 212 | 212 | 275 | 275 | 122 | 122 | . | . | 129 | 129 |

FIG. 10D

| 2005 IBM neigbors | chr. | | | 2 | 2 | 2 | 2 | 2 | 2 | 2 | 2 | 2 | 2 | 2 | 2 |
|---|---|---|---|---|---|---|---|---|---|---|---|---|---|---|---|
| 2005 IBM neigbors | position | | | 454 | 454 | 481 | 481 | 485 | 485 | 509 | 509 | 509 | 509 | 521 | 521 |
| sample No | sample | su1 | se | phi251315 | phi251315 | umc1049 | umc1049 | umc1745 | umc1745 | bmc1662 | bmc1662 | umc1126 | umc1126 | phi435417 | phi435417 |
| 1 | 017 | n | n | 127 | 127 | 96 | 96 | 138 | 138 | 124 | 124 | 139 | 139 | 215 | 215 |
| 2 | 044 | n | n | 127 | 127 | 123 | 123 | 128 | 128 | 124 | 124 | 139 | 139 | 215 | 215 |
| 3 | 006 | n | p | 127 | 127 | 96 | 96 | 128 | 128 | 124 | 124 | 139 | 139 | 215 | 215 |
| 4 | 007 | n | p | 127 | 127 | 96 | 96 | 138 | 138 | 124 | 124 | 139 | 139 | 215 | 215 |
| 5 | 009 | n | p | 127 | 127 | 96 | 96 | 128 | 128 | 124 | 124 | 139 | 139 | 215 | 215 |
| 6 | 047 | n | p | 127 | 127 | 96 | 96 | 138 | 138 | 124 | 124 | 139 | 139 | 215 | 215 |
| 7 | 637 | n | p | 127 | 127 | 96 | 96 | . | . | 124 | 124 | 139 | 139 | 215 | 215 |
| 8 | 001 | p | n | 127 | 127 | 96 | 96 | 138 | 138 | 124 | 124 | 139 | 139 | 215 | 215 |
| 9 | 046 | p | n | 127 | 127 | 96 | 96 | 138 | 138 | 124 | 124 | 139 | 139 | 215 | 215 |
| 10 | 048 | p | n | 127 | 127 | 96 | 96 | 138 | 138 | 124 | 124 | 139 | 139 | 215 | 215 |
| 11 | 049 | p | n | 127 | 127 | 96 | 96 | 138 | 138 | 124 | 124 | 139 | 139 | 215 | 215 |
| 12 | 109 | p | n | 127 | 127 | 96 | 96 | 138 | 138 | 124 | 124 | 139 | 139 | 215 | 215 |
| 13 | 354 | p | n | 127 | 127 | 96 | 96 | 138 | 138 | 124 | 124 | 139 | 139 | 215 | 215 |
| 14 | sh2-I | n | n | 124 | 124 | 84 | 84 | 138 | 138 | 160 | 160 | 139 | 139 | 215 | 215 |

FIG. 10E

| 2005 IBM neigbors | chr. | | | 2 | 2 | 2 | 2 | 2 | 2 | 2 | 2 | 2 | 2 |
|---|---|---|---|---|---|---|---|---|---|---|---|---|---|
| 2005 IBM neigbors | position | | | 529 | 529 | 548 | 548 | 549 | 549 | 573 | 573 | 578 | 578 |
| sample No | sample | su1 | se | bmc1316 | bmc1316 | phi090 | phi090 | p-umc1633 | p-umc1633 | bnlg1908 | bnlg1908 | bmc1940 | bmc1940 |
| 1 | 017 | n | n | 102 | 102 | 145 | 145 | 107 | 107 | 177 | 177 | 217 | 217 |
| 2 | 044 | n | n | 112 | 112 | 145 | 145 | 107 | 107 | 177 | 177 | 222 | 222 |
| 3 | 006 | n | p | 112 | 112 | 145 | 145 | 107 | 107 | 177 | 177 | 222 | 222 |
| 4 | 007 | n | p | 110 | 110 | 138 | 138 | 107 | 107 | 177 | 177 | 222 | 222 |
| 5 | 009 | n | p | 112 | 112 | 145 | 145 | 107 | 107 | 177 | 177 | 222 | 222 |
| 6 | 047 | n | p | 110 | 110 | 138 | 138 | 107 | 107 | 177 | 177 | 222 | 222 |
| 7 | 637 | n | p | 110 | 110 | 138 | 138 | 107 | 107 | 177 | 177 | 224 | 224 |
| 8 | 001 | p | n | 110 | 110 | 138 | 138 | 107 | 107 | 177 | 177 | 222 | 222 |
| 9 | 046 | p | n | 110 | 110 | 138 | 138 | 107 | 107 | 177 | 177 | 222 | 222 |
| 10 | 048 | p | n | 110 | 110 | 138 | 138 | 107 | 107 | 177 | 177 | 222 | 222 |
| 11 | 049 | p | n | 110 | 110 | 138 | 138 | 107 | 107 | 177 | 177 | 222 | 222 |
| 12 | 109 | p | n | 110 | 110 | 138 | 138 | 107 | 107 | 177 | 177 | 222 | 222 |
| 13 | 354 | p | n | 110 | 110 | 138 | 138 | 107 | 107 | 177 | 177 | 222 | 222 |
| 14 | sh2-i | n | n | 102 | 102 | 112 | 112 | 109 | 109 | 195 | 195 | 190 | 190 |

FIG. 10F

| sample No | sample | su1 | se | umc1230 | umc1230 | umc2358 | umc2358 | umc1551 | umc1551 | bnlg1520 | bnlg1520 | phi427434 | phi427434 | umc1256 | umc1256 |
|---|---|---|---|---|---|---|---|---|---|---|---|---|---|---|---|
| 2005 IBM neigbors chr. | | | | 2 | 2 | 2 | 2 | 2 | 2 | 2 | 2 | 2 | 2 | 2 | 2 |
| 2005 IBM neigbors position | | | | 592 | 592 | 592 | 592 | 592 | 592 | 592 | 592 | 600 | 600 | 601 | 601 |
| 1 | 017 | n | n | 206 | 206 | 118 | 118 | 154 | 154 | 177 | 177 | 122 | 122 | 176 | 176 |
| 2 | 044 | n | n | 206 | 206 | 118 | 118 | 154 | 154 | 170 | 170 | 131 | 131 | 176 | 176 |
| 3 | 006 | n | p | 206 | 206 | 118 | 118 | 150 | 150 | 170 | 170 | 131 | 131 | 176 | 176 |
| 4 | 007 | n | p | 206 | 206 | 118 | 118 | 150 | 150 | 195 | 195 | 122 | 122 | 176 | 176 |
| 5 | 009 | n | p | 206 | 206 | 118 | 118 | 150 | 150 | 170 | 170 | 122 | 122 | 176 | 176 |
| 6 | 047 | n | p | 206 | 206 | 118 | 118 | 150 | 150 | 195 | 195 | 122 | 122 | 176 | 176 |
| 7 | 637 | n | p | 206 | 206 | 118 | 118 | 150 | 150 | 195 | 195 | 131 | 131 | 176 | 176 |
| 8 | 001 | p | n | 206 | 206 | 118 | 118 | 150 | 150 | 195 | 195 | 122 | 122 | 176 | 176 |
| 9 | 046 | p | n | 206 | 206 | 118 | 118 | 150 | 150 | 195 | 195 | 122 | 122 | 176 | 176 |
| 10 | 048 | p | n | 206 | 206 | 118 | 118 | 150 | 150 | 195 | 195 | 122 | 131 | 176 | 176 |
| 11 | 049 | p | n | 206 | 206 | 118 | 118 | 150 | 150 | 195 | 195 | 122 | 122 | 176 | 176 |
| 12 | 109 | p | n | 206 | 206 | 118 | 118 | 150 | 150 | 195 | 195 | 122 | 122 | . | . |
| 13 | 354 | p | n | 206 | 206 | 118 | 118 | 150 | 150 | 195 | 195 | 122 | 122 | 176 | 176 |
| 14 | sh2-I | n | n | 122 | 122 | 115 | 115 | 142 | 142 | 179 | 179 | 126 | 126 | 139 | 139 |

Reported Region of the se gene

FIG. 10G

Reported Region of the se gene

| sample No | 2005 IBM neigbors sample | su1 | se | chr. 2 umc1252 position 601 | 2 umc1252 601 | 2 umc1525 602 | 2 umc1525 602 | 2 umc1736 602 | 2 umc1736 602 | 2 p-bnlg469 650 | 2 p-bnlg469 650 | 2 bnlg1893 655 | 2 bnlg1893 655 | 2 umc1207 665 | 2 umc1207 665 |
|---|---|---|---|---|---|---|---|---|---|---|---|---|---|---|---|
| 1 | 017 | n | n | 131 | 131 | 134 | 134 | 134 | 134 | . | . | 140 | 140 | 156 | 156 |
| 2 | 044 | n | n | 131 | 131 | 134 | 134 | . | . | . | . | 138 | 138 | 134 | 134 |
| 3 | 006 | n | p | 131 | 131 | 134 | 134 | 134 | 134 | . | . | 138 | 138 | 134 | 134 |
| 4 | 007 | n | p | 131 | 131 | 134 | 134 | 134 | 134 | . | . | 140 | 140 | 156 | 156 |
| 5 | 009 | n | p | 131 | 131 | 134 | 134 | 134 | 134 | . | . | 140 | 140 | 156 | 156 |
| 6 | 047 | n | p | 131 | 131 | 134 | 134 | 134 | 134 | . | . | 140 | 140 | 156 | 156 |
| 7 | 637 | n | p | 131 | 131 | 134 | 134 | 134 | 134 | . | . | 140 | 140 | 156 | 156 |
| 8 | 001 | p | n | 131 | 131 | 134 | 134 | 134 | 134 | . | . | 140 | 140 | 156 | 156 |
| 9 | 046 | p | n | 131 | 131 | 134 | 134 | 134 | 134 | . | . | 140 | 140 | 156 | 156 |
| 10 | 048 | p | n | 131 | 131 | 134 | 134 | 134 | 134 | . | . | 140 | 140 | 156 | 156 |
| 11 | 049 | p | n | 131 | 131 | 134 | 134 | 134 | 134 | . | . | 140 | 140 | 156 | 156 |
| 12 | 109 | p | n | 131 | 131 | 134 | 134 | 134 | 134 | . | . | 140 | 140 | 156 | 156 |
| 13 | 354 | p | n | 127 | 127 | 134 | 134 | 134 | 134 | . | . | 140 | 140 | 156 | 156 |
| 14 | sh2-i | n | n | 131 | 131 | 132 | 132 | 131 | 131 | . | . | 138 | 138 | 147 | 147 |

FIG. 10H

| 2005 IBM neigbors | chr. | | | Reported Region of the se gene | | | | | | | | | | | |
|---|---|---|---|---|---|---|---|---|---|---|---|---|---|---|---|
| | | | | 2 | 2 | 2 | 2 | 2 | 2 | 2 | 2 | 2 | 2 | 2 | 2 |
| 2005 IBM neigbors | position | | | 685 | 685 | 692 | 692 | 692 | 692 | 712 | 712 | 713 | 713 | 716 | 716 |
| sample No | sample | su1 | se | umc1704 | umc1704 | umc2077 | umc2077 | umc2184 | umc2184 | phi101049 | phi101049 | umc2214 | umc2214 | umc1696 | umc1696 |
| 1 | 017 | n | n | 258 | 258 | 153 | 153 | 94 | 94 | 227 | 227 | 272 | 272 | 107 | 107 |
| 2 | 044 | n | n | 255 | 255 | 153 | 153 | 101 | 101 | 231 | 231 | 227 | 227 | 107 | 107 |
| 3 | 006 | n | p | 255 | 255 | 153 | 153 | 111 | 111 | 231 | 231 | 227 | 227 | 107 | 107 |
| 4 | 007 | n | p | 264 | 264 | 150 | 150 | 94 | 94 | 235 | 235 | 227 | 227 | 107 | 107 |
| 5 | 009 | n | p | 255 | 255 | . | . | 111 | 111 | 231 | 231 | 227 | 227 | 107 | 107 |
| 6 | 047 | n | p | 264 | 264 | 150 | 150 | 94 | 94 | 235 | 235 | 227 | 227 | 107 | 107 |
| 7 | 637 | n | p | 255 | 255 | 153 | 153 | 101 | 101 | 231 | 231 | 227 | 227 | 107 | 107 |
| 8 | 001 | p | n | 264 | 264 | 150 | 150 | 94 | 94 | 235 | 235 | 227 | 227 | 107 | 107 |
| 9 | 046 | p | n | 264 | 264 | 150 | 150 | 94 | 94 | 235 | 235 | 227 | 227 | 107 | 107 |
| 10 | 048 | p | n | 264 | 264 | 150 | 150 | 94 | 94 | 235 | 235 | 227 | 227 | 107 | 107 |
| 11 | 049 | p | n | 264 | 264 | 150 | 150 | 94 | 94 | 235 | 235 | 227 | 227 | 107 | 107 |
| 12 | 109 | p | n | 264 | 264 | 150 | 150 | 94 | 94 | 235 | 235 | 227 | 227 | 107 | 107 |
| 13 | 354 | p | n | 264 | 264 | 150 | 150 | 94 | 94 | 235 | 235 | 227 | 227 | 107 | 107 |
| 14 | sh2-I | n | n | . | . | 138 | 138 | 111 | 111 | 225 | 225 | 227 | 227 | . | . |

FIG. 10I

|  |  |  |  |  |  |  |  | A- 3 |  | A- 3 |  |  |  |  |  |
|---|---|---|---|---|---|---|---|---|---|---|---|---|---|---|---|
| 2005 IBM neigbors | chr. |  |  | 3 | 3 | 3 | 3 | 3 | 3 | 3 | 3 | 3 | 3 | 3 | 3 |
| 2005 IBM neigbors | position |  |  | 7.5 | 7.5 | 38 | 38 | 52 | 52 | 55 | 55 | 164 | 164 | 168 | 168 |
| sample No | sample | su1 | se | phi453121 | phi453121 | phi104127 | phi104127 | phi374118 | phi374118 | phi193225 | phi193225 | phi243966 | phi243966 | phi029 | phi029 |
| 1 | 017 | n | n | 213 | 213 | 163 | 163 | . | . | 136 | 136 | 209 | 209 | 152 | 152 |
| 2 | 044 | n | n | 213 | 213 | 163 | 163 | . | . | 136 | 136 | 209 | 209 | 152 | 152 |
| 3 | 006 | n | p | 213 | 213 | 163 | 163 | . | . | 136 | 136 | 209 | 209 | 152 | 152 |
| 4 | 007 | n | p | 213 | 213 | 163 | 163 | . | . | 136 | 136 | 209 | 209 | 152 | 152 |
| 5 | 009 | n | p | 213 | 213 | 163 | 163 | . | . | 136 | 136 | 209 | 209 | 152 | 152 |
| 6 | 047 | n | p | 213 | 213 | 163 | 163 | . | . | 136 | 136 | 209 | 209 | 152 | 152 |
| 7 | 637 | n | p | 213 | 213 | 163 | 163 | . | . | 136 | 136 | 209 | 209 | 152 | 152 |
| 8 | 001 | p | n | 213 | 213 | 163 | 163 | . | . | 136 | 136 | 209 | 209 | 152 | 152 |
| 9 | 046 | p | n | 213 | 213 | 163 | 163 | . | . | 136 | 136 | 209 | 209 | 152 | 152 |
| 10 | 048 | p | n | 213 | 213 | 163 | 163 | . | . | 136 | 136 | 209 | 209 | 152 | 152 |
| 11 | 049 | p | n | 213 | 213 | 163 | 163 | . | . | 136 | 136 | 209 | 209 | 152 | 152 |
| 12 | 109 | p | n | 213 | 213 | 163 | 163 | . | . | 136 | 136 | 209 | 209 | 152 | 152 |
| 13 | 354 | p | n | 213 | 213 | 163 | 163 | . | . | 136 | 136 | 209 | 209 | 152 | 152 |
| 14 | sh2-i | n | n | 213 | 213 | 163 | 163 | 212 | 212 | 123 | 123 | 209 | 209 | 152 | 152 |

FIG. 10J

| 2005 IBM neigbors | chr. | | | | | 3 | 3 | 3 | 3 | 3 | 3 | 3 | 3 | 3 | 3 | 3 | 3 |
|---|---|---|---|---|---|---|---|---|---|---|---|---|---|---|---|---|---|
| 2005 IBM neigbors | position | | | | | 298 | 298 | 306 | 306 | 445 | 445 | 618 | 618 | 619 | 619 | 627 | 627 |
| sample No | sample | su1 | se | phi053 | phi053 | phi073 | phi073 | phi102228 | phi102228 | umc1915 | umc1915 | bmc1108 | bmc1108 | umc2081 | umc2081 |
| 1 | 017 | n | n | . | . | | | 185 | 185 | 128 | 128 | . | . | . | . | . | . |
| 2 | 044 | n | n | . | . | | | 185 | 185 | 128 | 128 | . | . | . | . | . | . |
| 3 | 006 | n | p | . | . | | | 185 | 185 | 128 | 128 | . | . | . | . | . | . |
| 4 | 007 | n | p | . | . | | | 185 | 185 | 128 | 128 | . | . | . | . | . | . |
| 5 | 009 | n | p | . | . | | | 185 | 185 | 128 | 128 | . | . | . | . | . | . |
| 6 | 047 | n | p | . | . | | | 185 | 185 | 121 | 121 | . | . | . | . | . | . |
| 7 | 637 | n | p | . | . | | | 185 | 185 | 128 | 128 | . | . | . | . | . | . |
| 8 | 001 | p | n | . | . | | | 185 | 185 | 121 | 121 | . | . | . | . | . | . |
| 9 | 046 | p | n | . | . | | | 185 | 185 | 121 | 121 | . | . | . | . | . | . |
| 10 | 048 | p | n | . | . | | | 185 | 185 | 121 | 121 | . | . | . | . | . | . |
| 11 | 049 | p | n | . | . | | | 185 | 185 | 121 | 121 | . | . | . | . | . | . |
| 12 | 109 | p | n | . | . | | | 185 | 185 | 128 | 128 | . | . | . | . | . | . |
| 13 | 354 | p | n | . | . | | | 185 | 185 | 121 | 121 | . | . | . | . | . | . |
| 14 | sh2-i | n | n | 134 | 134 | | | 185 | 185 | 128 | 128 | . | . | . | . | . | . |

FIG. 10K

| | | | | | | | | | | | | | | | sh2 gene | |
|---|---|---|---|---|---|---|---|---|---|---|---|---|---|---|---|---|
| 2005 IBM neigbors | chr. | | | 3 | 3 | 3 | 3 | 3 | 3 | 3 | 3 | 3 | 3 | 3 | 3 | |
| 2005 IBM neigbors | position | | | 627 | 627 | 634 | 634 | 635 | 635 | 652 | 652 | 684 | 684 | 699 | 699 | |
| sample No | sample | su1 | se | umc1521 | umc1521 | umc1320 | umc1320 | umc1273 | umc1273 | umc2276 | umc2276 | umc2174 | umc2174 | sh2 | sh2 | |
| 1 | 017 | n | n | 129 | 129 | . | . | 113 | 113 | . | . | 127 | 127 | . | . | |
| 2 | 044 | n | n | 129 | 129 | . | . | 119 | 119 | . | . | 127 | 127 | . | . | |
| 3 | 006 | n | p | 129 | 129 | . | . | 119 | 119 | . | . | 127 | 127 | . | . | |
| 4 | 007 | n | p | 129 | 129 | . | . | 119 | 119 | . | . | 127 | 127 | . | . | |
| 5 | 009 | n | p | 129 | 129 | . | . | 119 | 119 | . | . | 127 | 127 | . | . | |
| 6 | 047 | n | p | 129 | 129 | . | . | 117 | 117 | . | . | 127 | 127 | . | . | |
| 7 | 637 | n | p | 129 | 129 | . | . | 119 | 119 | . | . | 118 | 118 | . | . | |
| 8 | 001 | p | n | 129 | 129 | . | . | 119 | 119 | . | . | 127 | 127 | . | . | |
| 9 | 046 | p | n | 129 | 129 | . | . | 119 | 119 | . | . | 127 | 127 | . | . | |
| 10 | 048 | p | n | 129 | 129 | . | . | 113 | 113 | . | . | 127 | 127 | . | . | |
| 11 | 049 | p | n | 129 | 129 | . | . | 119 | 119 | . | . | 127 | 127 | . | . | |
| 12 | 109 | p | n | 129 | 129 | . | . | 113 | 113 | . | . | 127 | 127 | . | . | |
| 13 | 354 | p | n | 129 | 129 | . | . | 119 | 119 | . | . | 127 | 127 | . | . | |
| 14 | sh2-i | n | n | 129 | 129 | . | . | 113 | 113 | . | . | 118 | 118 | . | . | |

FIG. 10L

| 2005 IBM neigbors | chr. | | | 3 | 3 | 3 | 3 | 3 | 3 | 3 | 3 | 3 | 3 | 3 | 3 |
|---|---|---|---|---|---|---|---|---|---|---|---|---|---|---|---|
| 2005 IBM neigbors | position | | | 702 | 702 | 702 | 702 | 730 | 730 | 739 | 739 | 747 | 747 | 748 | 748 |
| sample No | sample | su1 | se | bmc1257 | bmc1257 | bmc1182 | bmc1182 | dupssr33 | dupssr33 | umc2152 | umc2152 | umc2008 | umc2008 | umc2277 | umc2277 |
| 1 | 017 | n | n | 171 | 171 | . | . | 90 | 90 | . | . | 120 | 120 | 140 | 140 |
| 2 | 044 | n | n | 171 | 171 | . | . | 90 | 90 | . | . | 120 | 120 | 140 | 140 |
| 3 | 006 | n | p | 171 | 171 | . | . | 90 | 90 | . | . | 120 | 120 | 140 | 140 |
| 4 | 007 | n | p | 171 | 171 | . | . | 90 | 90 | . | . | 120 | 120 | 140 | 140 |
| 5 | 009 | n | p | 171 | 171 | . | . | 90 | 90 | . | . | 120 | 120 | 140 | 140 |
| 6 | 047 | n | p | 171 | 171 | . | . | 90 | 90 | . | . | 120 | 120 | 140 | 140 |
| 7 | 637 | n | p | 171 | 171 | . | . | 86 | 86 | . | . | . | . | 136 | 136 |
| 8 | 001 | p | n | 171 | 171 | . | . | 90 | 90 | . | . | 120 | 120 | 140 | 140 |
| 9 | 046 | p | n | 171 | 171 | . | . | 90 | 90 | . | . | 120 | 120 | 140 | 140 |
| 10 | 048 | p | n | 171 | 171 | . | . | 90 | 90 | . | . | 120 | 120 | 140 | 140 |
| 11 | 049 | p | n | 171 | 171 | . | . | 90 | 90 | . | . | 120 | 120 | 140 | 140 |
| 12 | 109 | p | n | 171 | 171 | . | . | 90 | 90 | . | . | 120 | 120 | 140 | 140 |
| 13 | 354 | p | n | 171 | 171 | . | . | 90 | 90 | . | . | . | . | 140 | 140 |
| 14 | sh2-i | n | n | 173 | 173 | 120 | 120 | 86 | 86 | 132 | 132 | . | . | 138 | 138 |

FIG. 10M

| sample No | 2005 IBM neigbors sample | su1 | se | chr. 3 position 749 umc1813 | 3 749 umc1813 | 3 752 bmc1536 | 3 752 bmc1536 | 4 9.9 phi072 | 4 9.9 phi072 | A- 4 4 24 phi213984 | A- 4 4 24 phi213984 | A- 4 4 53 Phi308090 | A- 4 4 53 Phi308090 | 4 81 phi295450 | 4 81 phi295450 |
|---|---|---|---|---|---|---|---|---|---|---|---|---|---|---|---|
| 1 | 017 | n | n | 106 | 106 | 158 | 158 | 136 | 136 | 303 | 303 | 216 | 216 | 185 | 185 |
| 2 | 044 | n | n | 106 | 106 | 158 | 158 | 136 | 136 | 303 | 303 | 216 | 216 | 185 | 185 |
| 3 | 006 | n | p | 106 | 106 | 158 | 158 | 136 | 136 | 303 | 303 | 218 | 218 | 185 | 185 |
| 4 | 007 | n | p | 106 | 106 | 158 | 158 | 136 | 136 | 303 | 303 | 218 | 218 | 185 | 185 |
| 5 | 009 | n | p | 106 | 106 | 158 | 158 | 136 | 136 | 303 | 303 | 216 | 216 | 185 | 185 |
| 6 | 047 | n | p | 106 | 106 | 158 | 158 | 136 | 136 | 303 | 303 | 218 | 218 | 185 | 185 |
| 7 | 637 | n | p | . | . | . | . | 136 | 136 | 303 | 303 | 216 | 216 | 185 | 185 |
| 8 | 001 | p | n | 106 | 106 | 158 | 158 | 136 | 136 | 303 | 303 | 218 | 218 | 185 | 185 |
| 9 | 046 | p | n | 106 | 106 | 158 | 158 | 136 | 136 | 303 | 303 | 218 | 218 | 185 | 185 |
| 10 | 048 | p | n | 106 | 106 | 158 | 158 | 136 | 136 | 303 | 303 | 218 | 218 | 185 | 185 |
| 11 | 049 | p | n | 106 | 106 | 158 | 158 | 136 | 136 | 303 | 303 | 218 | 218 | 185 | 185 |
| 12 | 109 | p | n | 106 | 106 | 158 | 158 | 136 | 136 | 303 | 303 | 218 | 218 | 185 | 185 |
| 13 | 354 | p | n | 106 | 106 | 158 | 158 | 136 | 136 | 303 | 303 | 218 | 218 | 185 | 185 |
| 14 | sh2-i | n | n | 106 | 106 | 158 | 158 | 136 | 136 | 303 | 303 | 201 | 201 | 170 | 170 |

FIG. 10N

| 2005 IBM neigbors | chr. | | | A-4 4 | 4 | 4 | 4 | 4 | 4 | su1 4 | 4 | 4 | 4 | 4 | 4 |
|---|---|---|---|---|---|---|---|---|---|---|---|---|---|---|---|
| 2005 IBM neigbors | position | | | 102 | 102 | 232 | 232 | 254 | 254 | 264 | 264 | 522 | 522 | 744 | 744 |
| sample No | sample | su1 | se | phi438301 | phi438301 | phi096 | phi096 | phi079 | phi079 | su1 | su1 | phi093 | phi093 | phi076 | phi076 |
| 1 | 017 | n | n | 208 | 208 | 185 | 185 | 184 | 184 | wt | wt | . | . | 159 | 159 |
| 2 | 044 | n | n | 208 | 208 | 185 | 185 | 184 | 184 | wt | wt | . | . | 170 | 170 |
| 3 | 006 | n | p | 208 | 208 | 185 | 185 | 184 | 184 | wt | wt | . | . | 170 | 170 |
| 4 | 007 | n | p | 208 | 208 | 185 | 185 | 184 | 184 | wt | wt | . | . | 164 | 164 |
| 5 | 009 | n | p | 208 | 208 | 185 | 185 | 184 | 184 | wt | wt | . | . | 170 | 170 |
| 6 | 047 | n | p | 208 | 208 | 185 | 185 | 186 | 186 | wt | wt | . | . | 170 | 170 |
| 7 | 637 | n | p | 208 | 208 | 185 | 185 | 184 | 184 | wt | wt | . | . | 170 | 170 |
| 8 | 001 | p | n | 208 | 208 | 185 | 185 | 186 | 186 | su1 | su1 | . | . | 170 | 170 |
| 9 | 046 | p | n | 208 | 208 | 185 | 185 | 184 | 184 | wt | wt | . | . | 170 | 170 |
| 10 | 048 | p | n | 208 | 208 | 185 | 185 | 186 | 186 | su1 | su1 | . | . | 170 | 170 |
| 11 | 049 | p | n | 208 | 208 | 185 | 185 | 186 | 186 | su1 | su1 | . | . | 170 | 170 |
| 12 | 109 | p | n | 208 | 208 | 185 | 185 | 186 | 186 | su1 | su1 | . | . | 170 | 170 |
| 13 | 354 | p | n | 208 | 208 | 185 | 185 | 186 | 186 | su1 | su1 | . | . | 170 | 170 |
| 14 | sh2-i | n | n | 208 | 208 | 185 | 185 | 184 | 184 | . | . | . | . | 164 | 164 |

Note: Both marker phi079 and the su1 marker give the same result for these lines suggesting that line 46 may not have su1. Also Marker phi079 indicates that line 047 may have su1 but the su1 marker indicates it does not.

FIG. 10O

| sample No | 2005 IBM neigbors chr. | | | A-5 5 | 5 | 5 | 5 | A-5 5 | 5 | 5 | 5 | 5 | 5 | 5 | 5 |
|---|---|---|---|---|---|---|---|---|---|---|---|---|---|---|---|
| | 2005 IBM neigbors position | | | 73 | 73 | 82 | 82 | 91 | 91 | 286 | 286 | 307 | 307 | 394 | 394 |
| | sample | su1 | se | phi396160 | phi396160 | phi024 | phi024 | Phi330507 | Phi330507 | Phi109188 | Phi109188 | phi331888 | phi331888 | phi333597 | phi333597 |
| 1 | 017 | n | n | 298 | 298 | 358 | 358 | 131 | 131 | 160 | 160 | 134 | 134 | 216 | 216 |
| 2 | 044 | n | n | 298 | 298 | 358 | 358 | 131 | 131 | 160 | 160 | 124 | 124 | 216 | 216 |
| 3 | 006 | n | p | 298 | 298 | 355 | 355 | 131 | 131 | 160 | 160 | 124 | 124 | 216 | 216 |
| 4 | 007 | n | p | 298 | 298 | 355 | 355 | 131 | 131 | 160 | 160 | 124 | 124 | 216 | 216 |
| 5 | 009 | n | p | 298 | 298 | 358 | 358 | 131 | 131 | 160 | 160 | 124 | 124 | 216 | 216 |
| 6 | 047 | n | p | 298 | 298 | 355 | 355 | 131 | 131 | 160 | 160 | 124 | 124 | 216 | 216 |
| 7 | 637 | n | p | 298 | 298 | 355 | 355 | 131 | 131 | 160 | 160 | 124 | 124 | 216 | 216 |
| 8 | 001 | p | n | 298 | 298 | 355 | 355 | 131 | 131 | 160 | 160 | 124 | 124 | 216 | 216 |
| 9 | 046 | p | n | 298 | 298 | 355 | 355 | 131 | 131 | 160 | 160 | 124 | 124 | 216 | 216 |
| 10 | 048 | p | n | 298 | 298 | 355 | 355 | 131 | 131 | 160 | 160 | 124 | 124 | 220 | 220 |
| 11 | 049 | p | n | 298 | 298 | 355 | 355 | 131 | 131 | 160 | 160 | 124 | 124 | 216 | 216 |
| 12 | 109 | p | n | 298 | 298 | 355 | 355 | 131 | 131 | 160 | 160 | 124 | 124 | 216 | 216 |
| 13 | 354 | p | n | 298 | 298 | 355 | 355 | 131 | 131 | 160 | 160 | 124 | 124 | 216 | 216 |
| 14 | sh2-i | n | n | 274 | 274 | 358 | 358 | 131 | 131 | 160 | 160 | 132 | 132 | . | . |

FIG. 10P

| 2005 IBM neigbors | chr. | | | 5 | 5 | A- 6 | | A- 6 | | A- 6 | | A- 6 | | | |
|---|---|---|---|---|---|---|---|---|---|---|---|---|---|---|---|
| | | | | | | 6 | 6 | 6 | 6 | 6 | 6 | 6 | 6 | 6 | 6 |
| 2005 IBM neigbors | position | | | 529 | 529 | 81 | 81 | 95 | 95 | 107 | 107 | 125 | 125 | 200 | 200 |
| sample No | sample | su1 | se | phi85 | phi85 | phi389203 | phi389203 | phi452693 | phi452693 | phi445613 | phi445613 | phi364545 | phi364545 | phi423796 | phi423796 |
| 1 | 017 | n | n | 257 | 257 | 300 | 300 | 130 | 130 | 104 | 104 | 131 | 131 | 128 | 128 |
| 2 | 044 | n | n | 257 | 257 | 309 | 309 | 130 | 130 | 98 | 98 | 133 | 133 | 128 | 128 |
| 3 | 006 | n | p | 234 | 234 | 300 | 300 | 130 | 130 | 98 | 98 | 133 | 133 | 128 | 128 |
| 4 | 007 | n | p | 257 | 257 | 300 | 300 | 130 | 130 | 98 | 98 | 133 | 133 | 128 | 128 |
| 5 | 009 | n | p | 257 | 257 | 309 | 309 | 130 | 130 | 98 | 98 | 133 | 133 | 128 | 128 |
| 6 | 047 | n | p | 257 | 257 | 309 | 309 | 130 | 130 | 98 | 98 | 131 | 131 | 128 | 128 |
| 7 | 637 | n | p | 257 | 257 | 309 | 309 | 130 | 130 | 98 | 98 | 131 | 131 | 128 | 128 |
| 8 | 001 | p | n | 257 | 257 | 309 | 309 | 130 | 130 | 98 | 98 | 131 | 131 | 128 | 128 |
| 9 | 046 | p | n | 257 | 257 | 309 | 309 | 130 | 130 | 98 | 98 | 133 | 133 | 123 | 123 |
| 10 | 048 | p | n | 257 | 257 | 309 | 309 | 130 | 130 | 98 | 98 | 131 | 131 | 123 | 128 |
| 11 | 049 | p | n | 257 | 257 | 309 | 309 | 130 | 130 | 98 | 98 | 131 | 131 | 128 | 128 |
| 12 | 109 | p | n | 257 | 257 | 309 | 309 | 130 | 130 | 98 | 98 | 133 | 133 | 123 | 123 |
| 13 | 354 | p | n | 257 | 257 | 309 | 309 | 130 | 130 | 98 | 98 | 131 | 131 | 128 | 128 |
| 14 | sh2-i | n | n | 257 | 257 | 309 | 309 | 130 | 130 | 104 | 104 | 133 | 133 | 128 | 128 |

FIG. 10Q

| 2005 IBM neigbors | chr. | | | | | 6 | 6 | 6 | 6 | 7 | 7 | A- 7  7 | 7 | 7 | 7 | 7 | 7 |
|---|---|---|---|---|---|---|---|---|---|---|---|---|---|---|---|---|---|
| 2005 IBM neigbors | position | | | | | 451 | 451 | 453 | 453 | 134 | 134 | 180 | 180 | 473 | 473 | 545 | 545 |
| sample No | sample | su1 | se | phi299852 | phi299852 | | | phi070 | phi070 | phi260485 | phi260485 | phi034 | phi034 | phi328175 | phi328175 | phi069 | phi069 |
| 1 | 017 | n | n | 132 | 132 | | | . | . | 285 | 285 | 120 | 120 | 127 | 127 | 203 | 203 |
| 2 | 044 | n | n | 129 | 129 | | | . | . | 285 | 285 | 120 | 120 | 127 | 127 | 205 | 205 |
| 3 | 006 | n | p | 129 | 129 | | | . | . | 285 | 285 | 120 | 120 | 127 | 127 | 205 | 205 |
| 4 | 007 | n | p | 129 | 129 | | | . | . | 300 | 300 | 138 | 138 | 127 | 127 | 205 | 205 |
| 5 | 009 | n | p | 110 | 110 | | | . | . | 285 | 285 | 138 | 138 | 127 | 127 | 205 | 205 |
| 6 | 047 | n | p | 110 | 110 | | | . | . | 285 | 285 | 138 | 138 | 127 | 127 | 205 | 205 |
| 7 | 637 | n | p | 110 | 110 | | | . | . | 285 | 285 | 138 | 138 | 127 | 127 | 205 | 205 |
| 8 | 001 | p | n | 110 | 110 | | | . | . | 285 | 285 | 120 | 138 | 127 | 127 | 205 | 205 |
| 9 | 046 | p | n | 110 | 110 | | | . | . | 285 | 285 | 120 | 120 | 127 | 127 | 205 | 205 |
| 10 | 048 | p | n | 110 | 110 | | | . | . | 285 | 285 | 138 | 138 | 127 | 127 | 205 | 205 |
| 11 | 049 | p | n | 110 | 110 | | | . | . | 285 | 285 | 120 | 120 | 127 | 127 | 205 | 205 |
| 12 | 109 | p | n | 110 | 110 | | | . | . | 285 | 285 | 138 | 138 | 127 | 127 | 205 | 205 |
| 13 | 354 | p | n | 110 | 110 | | | . | . | 285 | 285 | 120 | 120 | 127 | 127 | 205 | 205 |
| 14 | sh2-i | n | n | 110 | 110 | | | . | . | 302 | 302 | 138 | 138 | . | . | 195 | 195 |

FIG. 10R

| 2005 IBM neigbors | chr. | | | 7 | 7 | 7 | 7 | 8 | 8 | 8 | 8 | 8 | 8 | 8 | 8 |
|---|---|---|---|---|---|---|---|---|---|---|---|---|---|---|---|
| 2005 IBM neigbors | position | | | 593 | 593 | 612 | 612 | 250 | 250 | 275 | 275 | 281 | 281 | 290 | 290 |
| sample No | sample | su1 | se | phi051 | phi051 | phi116 | phi116 | phi420701 | phi420701 | phi100175 | phi100175 | phi115 | phi115 | phi121 | phi121 |
| 1 | 017 | n | n | 138 | 138 | 168 | 168 | 290 | 290 | . | . | 291 | 291 | 92 | 92 |
| 2 | 044 | n | n | 138 | 138 | 158 | 158 | 290 | 290 | . | . | 291 | 291 | 92 | 92 |
| 3 | 006 | n | p | 138 | 138 | 158 | 158 | 290 | 290 | . | . | 303 | 303 | 92 | 92 |
| 4 | 007 | n | p | 138 | 138 | 158 | 158 | 290 | 290 | . | . | 303 | 303 | 92 | 92 |
| 5 | 009 | n | p | 138 | 138 | 168 | 168 | 290 | 290 | . | . | 291 | 291 | 92 | 92 |
| 6 | 047 | n | p | 138 | 138 | 158 | 158 | 290 | 290 | . | . | 303 | 303 | 92 | 92 |
| 7 | 637 | n | p | 138 | 138 | 168 | 168 | 290 | 290 | . | . | 303 | 303 | 92 | 92 |
| 8 | 001 | p | n | 138 | 138 | 158 | 158 | 290 | 290 | . | . | 303 | 303 | 92 | 92 |
| 9 | 046 | p | n | 138 | 138 | 158 | 158 | 290 | 290 | . | . | 303 | 303 | 92 | 92 |
| 10 | 048 | p | n | 138 | 138 | 158 | 158 | 290 | 290 | . | . | 303 | 303 | 92 | 92 |
| 11 | 049 | p | n | 138 | 138 | 158 | 158 | 290 | 290 | . | . | 303 | 303 | 92 | 92 |
| 12 | 109 | p | n | 138 | 138 | 158 | 158 | 290 | 290 | . | . | 303 | 303 | 92 | 92 |
| 13 | 354 | p | n | 138 | 138 | 158 | 158 | 290 | 290 | . | . | 303 | 303 | 92 | 92 |
| 14 | sh2-i | n | n | 136 | 136 | 170 | 170 | . | . | 130 | 130 | 291 | 291 | 141 | 141 |

FIG. 10S

| 2005 IBM neigbors | chr. | | | 8 | 8 | 8 | 8 | 9 | 9 | A-9 9 | 9 | A-9 9 | 9 | 9 | 9 |
|---|---|---|---|---|---|---|---|---|---|---|---|---|---|---|---|
| 2005 IBM neigbors | position | | | 572 | 572 | 609 | 609 | 80 | 80 | 124 | 124 | 126 | 126 | 312 | 312 |
| sample No | sample | su1 | se | phi015 | phi015 | phi233376 | phi233376 | phi033 | phi033 | phi236654 | phi236654 | phi108411 | phi108411 | phi032 | phi032 |
| 1 | 017 | n | n | 82 | 82 | 140 | 140 | 249 | 249 | 117 | 117 | . | . | 233 | 233 |
| 2 | 044 | n | n | 82 | 82 | 140 | 140 | 240 | 240 | 117 | 117 | . | . | 233 | 233 |
| 3 | 006 | n | p | 94 | 94 | 140 | 140 | 240 | 240 | 117 | 117 | . | . | 233 | 233 |
| 4 | 007 | n | p | 82 | 82 | 140 | 140 | 240 | 240 | 117 | 117 | . | . | 239 | 239 |
| 5 | 009 | n | p | 82 | 82 | 140 | 140 | 240 | 240 | 117 | 117 | . | . | 239 | 239 |
| 6 | 047 | n | p | 82 | 82 | 140 | 140 | 249 | 249 | 117 | 117 | . | . | 239 | 239 |
| 7 | 637 | n | p | 94 | 94 | 140 | 140 | 240 | 240 | 117 | 117 | . | . | 233 | 233 |
| 8 | 001 | p | n | 82 | 82 | 140 | 140 | 240 | 240 | 117 | 117 | . | . | 239 | 239 |
| 9 | 046 | p | n | 82 | 82 | 140 | 140 | 240 | 240 | 117 | 117 | . | . | 239 | 239 |
| 10 | 048 | p | n | 82 | 82 | 140 | 140 | 240 | 240 | 117 | 117 | . | . | 239 | 239 |
| 11 | 049 | p | n | 82 | 82 | 140 | 140 | 249 | 249 | 117 | 117 | . | . | 239 | 239 |
| 12 | 109 | p | n | 82 | 82 | 140 | 140 | 249 | 249 | 117 | 117 | . | . | 239 | 239 |
| 13 | 354 | p | n | 82 | 82 | 140 | 140 | 240 | 240 | 117 | 117 | . | . | 239 | 239 |
| 14 | sh2-i | n | n | 86 | 86 | 128 | 128 | 249 | 249 | 117 | 117 | 112 | 112 | 239 | 239 |

FIG. 10T

| sample No | sample | su1 | se | 2005 IBM neigbors chr. | | | | A-10 | | A-10 | | A-10 | | | | |
|---|---|---|---|---|---|---|---|---|---|---|---|---|---|---|---|---|
| | | | | 9 | 9 | 10 | 10 | 10 | 10 | 10 | 10 | 10 | 10 | 10 | 10 | 10 |
| | | | | 2005 IBM neigbors position | | | | | | | | | | | | |
| | | | | 537 | 537 | 31 | 31 | 53 | 53 | 62 | 62 | 86 | 86 | 144 | 144 | 261 |
| | | | | phi448880 | phi448880 | phi041 | phi041 | phi96342 | phi96342 | phi050 | phi050 | phi301654 | phi301654 | phi059 | phi059 | phi062 |
| 1 | 017 | n | n | 185 | 185 | 195 | 195 | 246 | 246 | . | . | . | . | 152 | 152 | 160 |
| 2 | 044 | n | n | 185 | 185 | 195 | 195 | 246 | 246 | . | . | . | . | 152 | 152 | 160 |
| 3 | 006 | n | p | 185 | 185 | 195 | 195 | 246 | 246 | . | . | . | . | 152 | 152 | 160 |
| 4 | 007 | n | p | 185 | 185 | 195 | 195 | 246 | 246 | . | . | . | . | 142 | 142 | 160 |
| 5 | 009 | n | p | 185 | 185 | 195 | 195 | 246 | 246 | . | . | . | . | 152 | 152 | 160 |
| 6 | 047 | n | p | 185 | 185 | 195 | 195 | 246 | 246 | . | . | . | . | 152 | 152 | 160 |
| 7 | 637 | n | p | 185 | 185 | 195 | 195 | 246 | 246 | . | . | . | . | 152 | 152 | 160 |
| 8 | 001 | p | n | 185 | 185 | 195 | 195 | 246 | 246 | . | . | . | . | 152 | 152 | 160 |
| 9 | 046 | p | n | 185 | 185 | 195 | 195 | 246 | 246 | . | . | . | . | 152 | 152 | 160 |
| 10 | 048 | p | n | 185 | 185 | 195 | 195 | 246 | 246 | . | . | . | . | 152 | 152 | 160 |
| 11 | 049 | p | n | 185 | 185 | 195 | 195 | 246 | 246 | . | . | . | . | 152 | 152 | 160 |
| 12 | 109 | p | n | 185 | 185 | 195 | 195 | 246 | 246 | . | . | . | . | 152 | 152 | 160 |
| 13 | 354 | p | n | 185 | 185 | 195 | 195 | 246 | 246 | . | . | . | . | 152 | 152 | 160 |
| 14 | sh2-i | n | n | 185 | 185 | 195 | 195 | 246 | 246 | . | . | . | . | 142 | 142 | 158 |

FIG. 10U

| 2005 IBM neigbors | chr. | | | 10 | 10 | 10 | 11 | 11 | 11 | 11 | 11 | 11 | 11 | 11 | 11 | 11 |
|---|---|---|---|---|---|---|---|---|---|---|---|---|---|---|---|---|
| 2005 IBM neigbors | position | | | 261 | 290 | 290 | 1 | 1 | 2 | 2 | 3 | 3 | 4 | 4 | 5 | 5 |
| sample No | sample | su1 | se | phi062 | phi323152 | phi323152 | phi101249 | phi101249 | Phi346482 | Phi346482 | Phi213398 | Phi213398 | phi109624 | phi109624 | Phi159819 | Phi159819 |
| 1 | 017 | n | n | 160 | 137 | 137 | . | . | 119 | 119 | 302 | 302 | 131 | 131 | 125 | 125 |
| 2 | 044 | n | n | 160 | 137 | 137 | . | . | 119 | 119 | 302 | 302 | 131 | 131 | 125 | 125 |
| 3 | 006 | n | p | 160 | 137 | 137 | . | . | 119 | 119 | 302 | 302 | 140 | 140 | 125 | 125 |
| 4 | 007 | n | p | 160 | 134 | 134 | . | . | 119 | 119 | 302 | 302 | 140 | 140 | 125 | 125 |
| 5 | 009 | n | p | 160 | 137 | 137 | . | . | 119 | 119 | 302 | 302 | 131 | 131 | 125 | 125 |
| 6 | 047 | n | p | 160 | 137 | 137 | . | . | 119 | 119 | 302 | 302 | 131 | 131 | 125 | 125 |
| 7 | 637 | n | p | 160 | 137 | 137 | . | . | 119 | 119 | 302 | 302 | 140 | 140 | 125 | 125 |
| 8 | 001 | p | n | 160 | 137 | 137 | . | . | 119 | 119 | 302 | 302 | 131 | 131 | 133 | 133 |
| 9 | 046 | p | n | 160 | 137 | 137 | . | . | 119 | 119 | 302 | 302 | 131 | 131 | 133 | 133 |
| 10 | 048 | p | n | 160 | 137 | 137 | . | . | 119 | 119 | 302 | 302 | 131 | 131 | 125 | 133 |
| 11 | 049 | p | n | 160 | 137 | 137 | . | . | 119 | 119 | 302 | 302 | 131 | 131 | 133 | 133 |
| 12 | 109 | p | n | 160 | 137 | 137 | . | . | 119 | 119 | 302 | 302 | 140 | 140 | 133 | 133 |
| 13 | 354 | p | n | 160 | 137 | 137 | . | . | 119 | 119 | 302 | 302 | 140 | 140 | 125 | 125 |
| 14 | sh2-i | n | n | 158 | 135 | 135 | 141 | 141 | 119 | 119 | 302 | 302 | 136 | 136 | 125 | 125 |

METHODS FOR ENHANCING THE PRODUCTION AND CONSUMER TRAITS OF PLANTS

REFERENCE TO SEQUENCE LISTING SUBMITTED ON A COMPACT DISC

All material that is present in a replacement Sequence Listing in a computer readable form (CRF), in a form of two identical CD-R compact discs, that was filed with the U.S. Patent and Trademark Office ("Patent Office") on Jul. 14, 2010 for related parent U.S. patent application Ser. No. 12/462,959, filed on Aug. 12, 2009, which was created using PatentIn Version 3.5 computer software, and which has been determined to be compliant by the Patent Office, is hereby incorporated into this application by reference in its entirety. Each of these two identical CD-R compact discs is separately identified below.

Copy 1 Replacement Jul. 14, 2010

Patent Applicant: Bryant Jerome Long
Patent Application: U.S. Ser. No. 12/462,959
Filed: Aug. 12, 2009
Title: Methods for Enhancing the Production and Consumer Traits of Plants
Data Recordation Date: Jul. 14, 2010
Machine Format Used: IBM-PC
Operating System Used: Microsoft Windows XP
File Name: 3001401-00003—CRF Sequence Listing . . .
File Size: 35.7 KB
Number of Sequences: 29

Copy 2 Replacement Jul. 14, 2010

Patent Applicant: Bryant Jerome Long
Patent Application: U.S. Ser. No. 12/462,959
Filed: Aug. 12, 2009
Title: Methods for Enhancing the Production and Consumer Traits of Plants
Data Recordation Date: Jul. 14, 2010
Machine Format Used: IBM-PC
Operating System Used: Microsoft Windows XP
File Name: 3001401-00003—CRF Sequence Listing . . .
File Size: 35.7 KB
Number of Sequences: 29—

BACKGROUND OF THE INVENTION

1. Field of the Invention

This application is a continuation-in-part patent application of pending non-provisional patent application U.S. Ser. No. 12/462,959, filed on Aug. 12, 2009. This continuation-in-part patent application claims the benefit of prior non-provisional patent application U.S. Ser. No. 12/462,959, filed on Aug. 12, 2009, which patent application is hereby incorporated into this continuation-in-part patent application in its entirety by reference herein, including all drawings, all seed and/or other deposits made with the American Type Culture Collection (ATCC) and all sequence listings.

The present invention is directed to unique methods for producing plants, plant materials and seeds that very advantageously have enhanced production and consumer traits, such as an improved vigor and hardiness of the seeds, an enhanced seedling emergence and plant growth in both warm and cold soils (i.e., in different types of climates and at different temperatures), combined with a superior taste quality and kernel pericarp tenderness, and to improved plants, plant materials and seeds that are produced in accordance with these methods, or that have such traits. The invention provides a novel approach for combining a unique assembly of genetic traits in plants, plant materials and seeds, using double, triple and other allelic combinations, resulting in enhanced growing potential along with desirable consumer qualities.

2. Background

Maize

Corn (maize) is one of the most diverse grain crops that is present in nature, and there are a number of different types of corn, which are generally classified by characteristics of their kernel endosperm. The most common types of corn include flint, flour, dent, pop, sweet, waxy and pod. The physical appearance of each kernel type is determined by its endosperm pattern, quality and quantity.

Sweet corn is a kind of corn plant that is classified as *Zea mays*, var. *rugosa*, and that has white, yellow or bi-colored kernels that are sweet when they are in the immature milky stage as a result of having a high sugar content. Higher levels of sugar in the sweet corn kernels result in a lower osmotic potential, causing greater water uptake into the kernels. Sweet corn is typically eaten by human beings as a vegetable, either directly from the maize cob, or by having the sweet kernels removed from the cob, and is a major vegetable crop that is grown all over the world primarily for fresh consumption, rather than as animal feed or for flour production.

Sweet corn occurs as a spontaneous mutation in field corn, and can be the result of naturally-occurring mutations in the genes that control conversion of sugar to starch inside the endosperm of the corn kernel. Unlike field corn varieties, which are intended for livestock, and are typically harvested when their kernels are dry and fully mature (at the dent stage), sweet corn is typically picked when it is immature (at the milk stage), and eaten as a vegetable, rather than as a grain. Because the process of maturation involves converting sugar into starch, sweet corn typically stores poorly, and must be eaten in a fresh, canned or frozen manner before the kernels become tough and/or starchy. Following harvest, or if left on the stalk too long, sucrose in standard sweet corn becomes rapidly converted to starch. Kernels can lose as much as 50% of their sucrose at room temperature at around 24 hours after harvest.

Open pollinated (non-hybrid) varieties of white sweet corn started to become widely available in the United States in the 19th century. Two of the most enduring varieties, which are still available today, are Country Gentleman (a Shoepeg corn with small, white kernels in irregular rows) and Stowell's Evergreen. Sweet corn production in the 20th century was influenced by the following key developments:

(i) hybridization, which allowed for more uniform maturity, improved quality and disease resistance; and
(ii) identification of the separate gene mutations that are responsible for sweetness in corn, and the ability to breed varieties based on these characteristics, for example:
su (normal sugary);
se (sugary enhanced); and
sh2 (shrunken-2).

There are currently hundreds of varieties of sweet corn, with more varieties continuously being developed.

The fruit of the sweet corn plant is the corn kernel, and the ear consists of a collection of kernels on the cob. Because corn is a monocot, there is always an even number of rows of kernels. The ear is covered by tightly wrapped leaves (the husk).

Sweet corn has significant antioxidant activity, which can reduce the possibilities of developing heart disease and/or cancer. It also releases increased levels of ferulic acid, which provides additional health benefits.

There are several known genetic mutations that are responsible for the various types of sweet corn. Early varieties were the result of the mutant su1 (sugary-1) allele. Conventional su1 varieties contain about 5-10% sugar by weight.

Varieties of sweet corn that contain the shrunken-2 (sh2) gene typically produce higher than normal levels of sugar, and have a longer shelf life, in comparison with conventional sweet corn, and are frequently referred to as supersweet varieties. One specific gene in sweet corn, the shrunken-2 (sh2) gene, causes the mature corn kernel to dry and shrivel as it matures past the milky stage, which is an undesirable trait for seedling germination, early emergence and plant growth. The endosperm of conventional sh2 sweet corn kernels store less amounts of starch, and from about 4 to about 10 times more sugar, than conventional su1 sweet corn. This has permitted the long-distance shipping of sweet corn, and has enabled manufacturers to can sweet corn without adding extra sugar or salt to it.

The third gene mutation is the se1 (sugary enhanced-1) allele, which is incorporated in the genome of Everlasting Heritage varieties. Conventional sweet corn varieties with the se1 alleles typically have a longer storage life, and contain from about 12% to about 20% sugar (i.e., a much higher sugar level in comparison with the conventional su1 varieties).

All of the alleles that are responsible for sweet corn are recessive, so sweet corn must generally be isolated from any field corn varieties that release pollen at the same time. The endosperm develops from genes from both parents (male and female), and kernels will generally be tough and starchy.

Maize was first classified according to the carbohydrate that is stored in its endosperm. The most distinguishable sugar component that is present in sweet corn is sucrose, which accounts for the vast majority of its sweetness differentiation. (Abbott and Cobb, Inc., Plant Protection No. 9600094 (1998).) The reducing free sugars, glucose and fructose, are present in sweet corn in significantly lower levels. These reducing sugars primarily result from the natural hydrolysis of sucrose.

Most commercially-available sweet corns are based upon single recessive alleles that alter carbohydrate composition of the endosperm. Until about thirty years ago, sweet corn was typically defined by the su1 mutant allele located on chromosome four. Although the primary difference between sweet corn and field corn is historically due to a single gene, there are many other genes, both exhibiting major and minor effects that differentiate the two classifications of corn. These genes affect the overall eating quality of the corn (flavor, texture, tenderness and the like) along with the appearance of the kernel, ear and plant, as well as the viability of the seed. Sweet corn is differentiated mainly from other types of corn, i.e., flint, flour, dent, waxy, pop, and the like, by the presence of genes that typically alter endosperm starch synthesis and its use as a vegetable for human consumption.

Many of the endosperm mutant genes in maize (and in other crop plants) that are presently being used commercially in different sweet corn varieties, and affect endosperm carbohydrate synthesis, are listed in Table 1 below. These endosperm mutations all are believed to affect starch synthesis during kernel development, and have been characterized and mapped in maize.

TABLE 1

Sweet Corn Endosperm Mutant Genes Used Commercially

| Gene | Gene Symbol | Chromosome |
|---|---|---|
| Amylose-extender | ae | 5 |
| Brittle | bt | 5 |
| Brittle-2 | bt2 | 4 |
| Dull | du | 10 |
| Shrunken-2 | sh2 | 3 |
| Sugary-1 | su1 | 4 |
| Sugary enhancer-1 | se1 | 2 |
| Waxy | wx | 9 |

Of the endosperm mutants that are listed in Table 1, the mutants that are most widely used commercially are sugary-1 (su 1), sugary enhancer-1 (se1) and shrunken-2 (sh2).

Endosperm Mutants

Sweet corn eating quality is typically largely determined by its sweetness which, in turn, is affected by the amount of sugar and starch that are present in the endosperm of its kernels. The major and, therefore, most distinguishable sugar component in sweet corn is sucrose, which accounts for most of its sweetness differentiation. The reducing sugars, glucose and fructose, are typically present in sweet corn in significantly lower levels in comparison with sucrose. These reducing sugars typically result from the natural hydrolysis of sucrose. Sugary-1 (su1), sugary enhancer-1 (se1), and shrunken-2 (sh2) mutant alleles have been determined to markedly increase sugar content, and decrease starch levels, in sweet corn in comparison with corn that does not include one or more of these mutant alleles in its genome.

Another determining characteristic of sweet corn is that its kernels (seeds) tend to be markedly more tender in comparison with other types of corn. Significant degrees of tenderness levels may occur within sweet corn varieties expressing one or more of the above three (or other) endosperm mutant alleles. Elevated sugar levels and increased kernel pericarp tenderness that typically occur in these varieties generally allows for extended holding abilities or shelf lives. An extended holding ability or shelf life, both on and off of a corn plant (or other production or distribution facility), is generally extremely important when considering shipping sweet corn varieties over potentially long geographical distances to market, for example, across the United States, or from one country to another country.

Currently, for reasons related to elevated sugar and pericarp tenderness levels, the shrunken-2 (sh2) sweet corn class is the most popular type of sweet corn commercially available. However, as is described hereinbelow, such class has some very significant disadvantages, which are overcome by the processes and products of the present invention.

Su1 (Sugary-1) Mutant Gene

Sweet corn in its original form differs from field corn primarily by the presence of a single recessive mutant gene, sugary-1 (su1). The recessive sugary-1 (su1) genotype that is present in sweet corn has an effect of retarding (significantly slowing) a normal conversion of sugar into starch during endosperm development, which very desirably results in a sweet taste, rather than in a starchy taste. This gene has been cloned and mapped to the short arm of chromosome 4 in sweet corn, and its genomic sequence and amino acid sequence translation are set forth in U.S. Pat. No. 5,912,413 entitled "Isolation of the SU1 Starch Debranching Enzyme, the Product of the Maize Gene Sugary 1," and herein.

The sugary (su1) gene encodes a Class II starch debranching enzyme that is active in cellular plastids. It is an isoamylase that hydrolyzes the α-(1,6) branch linkages in starch during starch synthesis. (J A Shultz et al., "Current Models for Starch Synthesis and the Sugary Enhancer 1 (se1) Mutation in *Zea mays*," Plant Physiology and Biochemistry 42(6), 457-464 (2004).)

The sugary-1 (su1) gene confers a moderate increase in overall sugar levels to corn kernels, but disadvantageously has only about one half of the total sugar content of "supersweet" corn varieties conferred by the Shrunken-2 (sh2) gene, which is significantly less desirable to corn consumers. Also disadvantageously, the conversion of sugar to starch in the corn kernels is comparatively rapid, generally resulting in a reduced or narrow harvest window before the sweetness (i.e., sugar levels) of the corn kernels deteriorates after the prime eating stage (at approximately 75% kernel moisture).

The sugary-1 (su1) gene, contrary to its name, therefore, does not generally result in exceptionally high levels of sugars. However, it does generally result in greatly increased levels of phytoglycogen or water soluble polysaccharides (WSP). (W. F. Tracey, In A. R. Hellauer (ED) Specialty Corns (CRC Press, Boca Raton, Fla.) 147-187 (1994).) Phytoglycogen and WSP tend to give the endosperm of the kernels of conventional su1 sweet corn varieties the smooth texture and creaminess characteristic of traditional sweet corn varieties. Mature endosperm of non-mutant corn generally contains approximately 2% WSP, whereas corn lines that are homozygous for the sugary-1 (su1) gene may contain up to approximately 35% WSP.

The mutant sugary-1 (su1) gene present in conventional varieties of sweet corn disadvantageously tends to result in a significantly reduced seed quality and use compared to field corn varietal counterparts.

Additional information about the recessive sugary-1 (su1) gene is present in M. G. James et al., "Characterization of the Maize Gene Sugary-1, a Determinant of Starch Composition in Kernels," The Plant Cell, Vol. 7, 417-429 (1995); and D. Pan et al., "A Debranching Enzyme Deficiency in Endosperms of the Sugary-1 Mutants of Maize," Plant Physiol. 74(2), 324-328 (1984).

Se1 (Sugary Enhancer-1) Mutant Gene

The sugary enhancer-1 (se1) mutant gene is a recessive modifier of the sugary-1 (su1) gene mutation. (J A Shultz et al., "Current Models for Starch Synthesis and the Sugary Enhancer 1 (se1) Mutation in *Zea mays*," supra.). The effects of the sugary enhancer-1 (se1) mutant gene were originally observed in 111677a, a line derived from a three-way cross (Bolivia 1035X Illinois 44b X Illinois 442a). (J. W. Gonzales et al., "A New Inbred Line With High Sugar Content in Sweet Corn," *Hort Science* 9, 79 (1974)). When homozygous, the sugary enhancer-1 (se1) allele increases total sugar in conventional sugary-1 (su1) sweet corn variety corn kernels to levels that are comparable to those in shrunken-2 (sh2) sweet corn variety corn kernels, and without a reduction in phytoglycogen content or an appreciable reduction in WSP levels. This allele also increases total sugar in conventional shrunken-2 (sh2) sweet corn variety corn kernels (also without a reduction in phytoglycogen content or an appreciable reduction in WSP levels).

The effects of the sugary enhancer-1 (se1) gene are corn kernel elevated total sugars, lighter color, and slow dry down, and were originally observed in an inbred corn line designated as IL1677a. It was only later that these effects were attributed to the sugary enhancer-1 (se1) gene. (Y. Tadmer et al., "RFLP Mapping of the Sugar Enhancer 1 Gene in Maize," TAG Theoretical and Applied Genetics 91, 489-494 (1995); R A Brink, "Identity and Sources of a Sugar Enhancer Gene Located on the Long Arm of Chromosome 4 in Maize," J. Heredity 82, 176 (1991).)

The sugary enhancer-1 (se1) gene confers a higher moisture content to sweet corn kernels during postharvest periods of time, and also maintains relatively increased levels of phytoglycogen during this time. Additional benefits of this gene are reduced kernel pericarp levels (i.e., thickness), rendering corn kernels with an improved tenderness, and elevated levels of the sugar maltose. (J E Ferguson et al., "Genetics of Sugary Enhancer (Se), an Independent Modifier of Sweet Corn (Su)," J. Heredity 69(6), 377-380 (1978).)

When both the sugary enhancer-1 (se1) gene and the sugary-1 (su1) gene are recessive, the sugary enhancer-1 (se1) gene very advantageously confers from about 1.5 to about 2 times more sucrose to corn kernels at their peak harvest maturity in comparison with sugary (su1) gene mutant corn kernels.

The sugary enhancer-1 (se1) gene locus is situated on the long arm of chromosome 2 in sweet corn. Identifiable variants of the sugary enhancer-1 (se1) gene are currently being evaluated and characterized.

Apparent difficulties in the genomic characterization of the sugary enhancer-1 (se1) gene have previously been encountered by scientists. Such difficulties are considered, in part, to be due to its rather difficult concomitant phenotypic measurement.

The enzymatic basis for the sugary enhancer-1 (se1) gene currently does not appear to be known, and the nucleotide sequence of the sugary enhancer-1 (se1) gene currently does not appear to be known, and is not present in the Maize Genetics and Genomics Database or GenBank database. However, the inheritance of the sugary enhancer-1 (se1) gene can be determined by those having ordinary skill in the art by following nearby molecular markers on chromosome 2, as is described herein. Such a determination may also be made for other mutant genes.

Additional information about the sugary enhancer-1 (se1) gene is present in D. R. La Bonte et al., "Sugary Enhancer (se) Gene Located on the Long Arm of Chromosome 4 in Maize (*Zea mays* L.), The Journal of Heredity 82, 176-178 (1991); and J. E. Ferguson et al., "The Genetics of Sugary Enhancer (se), an Independent Modifier of Sweet Corn," The Journal of Heredity 69(6), 377-380 (1978).

Sh2 (Shrunken-2) Mutant Gene

In 1953, it was suggested that the mutant, recessive shrunken-2 (sh2) gene may have an application in the sweet corn industry. (J. R. Laughnan, "The Effects of sh2 Factor on Carbohydrate Reserves in the Mature Endosperm of Maize," Genetics 38, 485-499 (1953).) Since then, a significant amount of research has been performed in connection with high sugar-content corn and the shrunken-2 (sh2) gene, which is located on the long arm of chromosome 3 in sweet corn, and encodes the large subunit of ADP-glucose pyrophosphorylase (AGP), a Class I enzyme. This enzyme is important in the conversion pathway of sucrose to starch.

The conventional shrunken-2 (sh2) class of sweet corns (designated as "supersweet") comprises the vast majority of the U.S. commercial corn market. Mature dry shrunken-2 (sh2) variety corn kernels contain approximately twice the total sugar content, approximately ⅓ to ½ of the starch levels, and only trace levels of phytoglycogen, in comparison with conventional sugary-1 (su1) variety corn kernels. Shrunken-2 (sh2) type sweet corns generally result in dramatically reduced total carbohydrate levels at peak maturity, and express approximately two or more times the sucrose in comparison with conventional sugary-1 (su1) mutant sweet corn. Further, sugar retention at the post prime eating stage (i.e., during the period of time immediately following the prime eating stage) in these sweet corns is generally significantly extended relative to conventional sugary-1 (su1) and sugary enhancer-1 (se1) mutant sweet corns.

It has been determined that including the shrunken-2 (sh2) gene in the genetic makeup of corn advantageously has an effect of increasing the corn's total sugar content and, thus, sweetness. It has also been determined, however, that including this gene in the genetic makeup of corn very disadvantageously significantly lowers the corn's water soluble polysaccharide (WSP) content, reducing its endosperm content, and lowering its starch content (and its associated energy level). Disadvantageously, conventional shrunken-2 (sh2) varieties of corn generally lack the smooth and creamy texture of the conventional sugary-1 (su1) and sugary enhancer-1 (se1) mutant corn varieties as a result of such decreased levels of water soluble polysaccharides. (J A Shultz et al., "Current Models for Starch Synthesis and the Sugary Enhancer 1 (se1) Mutation in Zea mays," supra.) Also very disadvantageously, as a result of a reduced starch content, and an associated reduced level of energy, conventional shrunken-2 (sh2) varieties of corn generally have a significantly reduced germination and seedling vigor, fitness and/or health during germination, seedling emergence from soil, and plant development and growth in comparison with the conventional sugary-1 (su1) and sugary enhancer-1 (se1) sweet corn varieties, resulting in light-weight, thin and spindly-looking, easily-damaged corn plants, which often readily die when confronted with environmental or other stresses, potentially causing corn growers to lose entire crops of corn, and the associated potential earnings from such crops. Shrunken-2 (sh2) varieties of sweet corn generally express a markedly collapsed kernel physical appearance at the dry seed stage, and this dry seed "shrunken" appearance, and corresponding reduced kernel starch reserves, tends to render a relatively diminished seedling emergence and vigor at planting time or during germination. In general, mechanical precision seeding and stand establishment are markedly more difficult due to the dry seed collapsed and "shrunken" physical appearance. The germination of such seeds can be problematic both in inbred production and in hybrid stands.

To improve vigor and germination, dent corn (a species of field corn) has been used as the genetic background for the shrunken-2 (sh2) gene. However, the dominant dent corn genes can very disadvantageously necessitate an isolation of the shrunken-2 hybrids from both field and sweet corn, and any foreign pollen can cause all of the corn kernels to be dent corn in character. In addition, shrunken-2 hybrids require spatial or temporal isolation from sugary-1 (su1) and sugary enhanced-1 (se1) sweet corn varieties due to the presence of dominant Su1Su1 alleles utilized in the shrunken-2 (sh2) "supersweet" sweet corn varieties.

Comparison of Sucrose Levels, Sugar Retention Abilities and Pericarp Levels

Comparisons of the sucrose levels, sugar retention (holding) abilities, pericarp levels and changes in pericarp levels of conventional sweet corn varieties containing the sugary-1 (su1) gene, the sugary enhancer-1 (se1) gene or the shrunken-2 (sh2) gene at the prime eating stage, or over a seven-day period, are shown in FIGS. 1-4, respectively. (Abbott and Cobb, Inc., Plant Protection No. 9600094 (1998).)

FIG. 1 provides a generalized comparison of representative endosperm sucrose levels for the conventional sugary-1 (su1), sugary enhancer-1 (se1) and shrunken-2 (sh2) genetic mutant lines at the prime eating stage (at a level of approximately 75% moisture). FIG. 1 shows that the sugary-1 (su1) line has the lowest level of sucrose (about 7.5%), followed by the sugary enhancer-1 (se1) line (about 12.5%), and then by the shrunken-2 (sh2) line, which has a much higher level of sucrose in comparison with the other two lines (about 27.5%).

FIG. 2 shows the relative endosperm sugar retention or "holding ability" at room temperature for the conventional sugary-1 (su1), sugary enhancer-1 (se1) and shrunken-2 (sh2) genetic mutant lines at the prime eating stage (at a level of approximately 75% moisture) over a seven day interval (Days 1-7). It shows representative changes in endosperm sucrose levels over time for the three different genetic types. FIG. 2 shows that the sugary-1 (su1) line has the lowest level of sucrose at all times during the 7-day period (ranging from about 4% on Day 1 to about 1% on Day 7), followed by the sugary enhancer-1 (se1) line (ranging from about 12% on Day 1 to about 2% on Day 7), and then by the shrunken-2 (sh2) line, which has a much higher level of sucrose over each of Days 1-7 in comparison with the other two lines (ranging from about 25% on Day 1 to about 13% on Day 7).

FIG. 3 provides a comparison of representative pericarp levels for the conventional sugary-1 (su1), sugary enhancer-1 (se1) and shrunken-2 (sh2) genetic mutant lines at the prime eating stage (at a level of approximately 75% moisture). FIG. 3 shows that the sugary enhancer-1 (se1) line has the lowest level of pericarp (about 0.75%), followed by the sugary-1 (su1) line (about 1.1%), and then by the shrunken-2 (sh2) line, which has a much higher level of pericarp in comparison with the other two lines (about 1.6%).

FIG. 4 shows the relative pericarp levels at room temperature for the conventional sugary-1 (su1), sugary enhancer-1 (se1) and shrunken-2 (sh2) genetic mutant lines at the prime eating stage (at a level of approximately 75% moisture) over a seven day interval (Days 1-7). It shows representative changes in pericarp levels over time for the three different genetic types.

FIG. 4 shows that the shrunken-2 (sh2) line generally has the lowest level of pericarp during the 7-day period (ranging from about 1.6% on Day 1 to about 2.1% on Day 7), followed by the sugary enhancer-1 (se1) line (ranging from about 1.1% on Day 1 to about 4.9% on Day 7) and the sugary-1 (su1) line (ranging from about 1.7% on Day 1 to about 4.9% on Day 7).

The major advantages of the higher sugar types of corn, i.e., sugary enhancer-1 (se1) and shrunken-2 (sh2) varieties, are their: (i) greater sweetness; (ii) longer harvest window of time; and (iii) longer shelf life. A higher initial sugar level, and a slower sugar loss at harvest, or during the period of time immediately following the prime eating stage, provide greater flexibility of harvest, and of handling conditions, and a longer shelf life for the corn.

Sh2-i (Shrunken-2i) Mutant Gene

U.S. Pat. No. 6,184,438 B1 describes an identification and characterization of a mutant form of the shrunken-2 (sh2) gene, designated as shrunken-2i (sh2-i). When present in maize plants, this mutant allele (and variants thereof) is stated to confer enhanced germination characteristics to these plants as compared to maize plants that express the sh2. This patent describes methods for transforming plants with this mutant allele (and variants), and plants that have this mutant allele incorporated into their genomes.

ADP-glucose pyrophosphorylase is a maize endosperm enzyme that is an important enzyme in the synthesis of starch, and catalyzes a conversion of ATP and α-glucose-1-phosphate to ADP-glucose and pyrophosphate. ADP-glucose arising from the action of this enzyme is the major donor of glucose for starch biosynthesis in plants. AGP enzymes have been isolated from plant photosynthetic and non-photosynthetic tissues, and is a heterotetramer that contains two different subunits.

Maize endosperm ADP-glucose pyrophosphorylase is composed of two dissimilar subunits that are encoded by two unlinked genes, shrunken-2 (sh2) and brittle-2 (bt2). (M. Bhave et al., "Identification and Molecular Characterization of Shrunken-2 cDNA Clones of Maize," The Plant Cell 2:581-588 (1990); J. Bae et al., "Cloning and Characterization of the Brittle-2 Gene of Maize," Maydica 35:317-322 (1990).) These genes encode the large subunit and the small subunit of this enzyme, respectively. The protein produced by the shrunken-2 gene has a predicted molecular weight of 57,179 Da. (J. Shaw et al., "Genomic Nucleotide Sequence of a Wild-Type Shrunken-2 Allele of Zea mays," Plant Physiol. 98:1214-1216 (1992).)

Shrunken-2 (sh2) and brittle-2 (bt2) maize endosperm mutants generally have greatly reduced starch levels, which disadvantageously correspond with greatly reduced or deficient levels of AGP activity. Mutations of either gene have been shown to reduce AGP activity by about 95%. (C. Tsai et al., "Starch-Deficient Maize Mutant Lacking Adenosine Diphosphate Glucose Pyrophosphorylase Activity," Science 151:341-343 (1966); D. Dickinson et al., "Presence of ADP-Glucose Pyrophosphorylase in Shrunken-2 and Brittle-2 Mutants of Maize Endosperm," Plant Physiol. 44:1058-1062 (1969).) It has also been observed that enzymatic activities increase with the dosage of functional wild type shrunken-2 (sh2) and brittle-2 (bt2) alleles, whereas mutant enzymes generally have altered kinetic properties. AGP appears to be the rate limiting step in starch biosynthesis in plants. (D. Stark et al., "Regulation of the Amount of Starch in Plant Tissues by ADP Glucose Pyrophosphorylase," Science 258:287-292 (1992).)

The cloning and characterization of the genes encoding the AGP enzyme subunits have been reported for various plants, and include shrunken-2 (sh2) cDNA, shrunken-2 (sh2) genomic DNA, and brittle-2 (bt2) cDNA from maize, small subunit cDNA and genomic DNA from rice, small and large subunit cDNAs from spinach leaf, and potato tuber. In addition, cDNA clones have been isolated from wheat endosperm and leaf tissue and Arabidopsis thaliana leaf.

Gene splicing is essentially a two-step cleavage-ligation reaction that can produce molecular lesions in genes, such as the wildtype shrunken-2 (sh2) gene. The first step involves the cleavage at the 5' splice site that leads to the formation of an intron lariat with the adenosine residue of the branch point sequence located upstream to the 3' splice site. This is followed by the ligation of the exon and release of the intron lariat. (M. J. Moore et al., "Evidence of Two Active Sites in the Spliceosome Provided by Stereochemistry of Pre-mRNA Splicing," Nature 365:364-368 (1993); M. J. Moore et al., "Splicing of Precursors to mRNAs by the Spliceosome" in The RNA World. 303-308 (R. Gesteland and J. Atkins, eds., Cold Spring Harbor Laboratory Press, 1993); P. A. Sharp, "Split Genes and RNA Splicing," Cell 77:805-815 (1994); J. W. S. Brown, "Arabidopsis Intron Mutations and Pre-mRNA Splicing," Plant J. 10(5):771-780 (1996); G. G. Simpson et al., "Mutation of Putative Branchpoint Consensus Sequences in Plant Introns Reduces Splicing Efficiency," Plant J. 9(3): 369-380 (1996); G. G. Simpson et al., "Splicing of Precursors to mRNA in Higher Plants: Mechanism, Regulation and Subnuclear Organization of the Spliceosomal Machinery," Plant Mol. Biol. 32:1-41 (1996).) This set of events is carried out by pre-mRNA association with a conglomeration of small nuclear RNA (snRNAs) and nuclear proteins that forms a dynamic large ribonucleosome protein complex (a spliceosome). This fundamental process, common to all eukaryotic gene expression, can have a diverse impact on the regulation of gene expression. For example, imprecise or inaccurate pre-mRNA splicing often imparts a mutant phenotype, whereas alternative splicing is sometimes important in the regulation of gene expression. (C. F. Weil et al., "The Effects of Plant Transposable Element Insertion on Transcription Initiation and RNA Processing," Annu. Rev. Plant Physiol. Plant Mol. Biol. 41:527-552 (1990); R. Nishihama et al., "Possible Involvement of Differential Splicing in Regulation of the Activity of Arabidopsis ANP1 that is Related to Mitogen-Activated Protein Kinase Kinase Kinases (MAPKKKs)," Plant J. 12(1):39-48 (1997); M. Golovkin et al., "Structure and Expression of a Plant U1 snRNP 70K Gene: Alternative Splicing of U1 snRNP 70K Pre-mRNAs Produces Two Different Transcripts," Plant Cell 8:1421-1435 (1996); J. Callis et al., "Introns Increase Gene Expression in Cultured Maize Cells," Genes and Development 1: 1183-1200). There are structural/sequence differences that may differentiate plant introns from those of vertebrate and yeast introns. (G. J. Goodall et al., "The AU-Rich Sequences Present in the Introns of Plant Nuclear Pre-mRNAs Are Required for Splicing," Cell 58:473-483 (1989); G. J. Goodall et al., "Different Effects of Intron Nucleotide Composition and Secondary Structure on Pre-mRNA Splicing in Monocot and Dicot Plants," EMBO J. 10(9):2635-2644 (1991).) One feature that distinguishes plant introns from those of other organisms is their AU richness. This has been implicated to be essential for intron processing, and for a definition of the intron/exon junction. (H. Lou et al., "3' Splice Site Selection in Dicot Plant Nuclei is Position Dependent," Mol. Cell. Biol. 13(8):4485-4493 (1993); A. J. McCullough, "Factors Affecting Authentic 5' Splice Site Selection in Plant Nuclei," Mol. Cell. Biol. 13(3):1323-1331 (1993); J. C. Carle-Urioste et al., "In Vivo Analysis of Intron Processing using Splicing-Dependent Reporter Gene Assays," Plant Mol. Biol. 26:1785-1795 (1994).) The requirement of an AU rich region appears to be more stringent in dicots in comparison with monocots, and some monocot introns are GC-rich.

The wildtype shrunken-2 (sh2) gene, the nucleotide sequence of which is shown in SEQ ID NO. 1, has 16 exons which, in term, are separated by 15 introns, as is shown in FIG. 5. This gene is estimated to be approximately 6000 base pairs long. One intron, in particular, is of significance for the sh2-i allele. This intron, designated "intron 2," contains at least about 7,800 base pairs in the sh2-i gene.

In comparison with the wildtype shrunken-2 (sh2) gene, the mutant shrunken-2i (sh2-i) gene is characterized by a single base pair change at the end of intron 2, as is shown in FIGS. 5 and 9. The mutant polynucleotide comprises a substitution of the wild-type terminal base at the end of intron 2 from a G to another base, such as to A, C or T (and not the wild type G nucleotide), and preferably to A. For example, if the shrunken-2 gene of maize contains a G to A mutation of the terminal nucleotide of this intron, the result would be a change of the AG nucleotide sequence that is found at the terminus of this plant gene intron to an AA sequence at the 3'-terminus of this intron. In other words, the result is a molecular lesion of the sh2-i allele in which it has undergone a G to A mutation at the terminal base of intron 2 in the maize sh2 gene.

The mutant sh2-i allele (and variants thereof), when expressed in a plant, such as maize, provides the plant with enhanced growth characteristics, such as an enhanced germination, and an enhanced seedling, seed and/or plant vigor, in comparison with other sweet corn varieties, in combination with desirable consumer traits, such as sweetness.

Inbred sweet corn lines containing the mutant sh2-i allele ("sh2-i conversion inbreds") generally demonstrate sweetness, and sugar levels, that are similar to conventional shrunken-2 (sh2) counterparts at the peak eating stage (at approximately 75% moisture). However, at a point in time just past the prime eating stage, mutant sh2-i inbred plant lines initiate a rapid acceleration of starch synthesis. This results in dry seed phenotypes that are physically significantly fuller and heavier than their shrunken-2 (sh2) counterparts and, to some degree, resemble a modified flint corn seed appearance. The net result is an overall enhancement of seed and seedling germination and vigor, and plant vigor, along with associated enhanced plant growth characteristics. This improved germination, and accelerated plant growth phenomenon, directly results in improved varietal crop yield potentials and consistencies.

Laboratory cold soil germination testing conducted by the present inventor comparing conventional shrunken-2 (sh2) hybrid maize varieties with maize varieties expressing the shrunken-2i (sh2-i) gene resulted in substantially stronger scores for the sh2-i hybrids. Table 2 below provides laboratory cold soil germination scores for corn hybrid near isogenic lines (NILs) designated as ACX 5137Y (not expressing the sh2-i allele) and ACX SS 7501Y (expressing the sh2-i allele). These are essentially comparisons of two maize hybrids differing only in the presence of the sh2-i allele. Scores represent means of three replicated tests of 100 kernels each.

TABLE 2

Cold Soil Germination Scores for Isoline Hybrids

| Isoline Hybrid | Cold Soil Germination (% Germination) |
|---|---|
| ACX 5137Y (not containing the sh2-i allele in its genome) | 82 |
| ACX SS 7501Y (containing the sh2-i allele in its genome) | 97 |

Similar laboratory results have been generated for numerous other hybrid comparisons between conventional shrunken-2 (sh2) hybrids containing, or not containing, the sh2-i allele. In addition, field germination and stand establishment data in Florida and California have substantiated laboratory data findings.

Organoleptic testing of numerous corn hybrid near isogenic lines (NILs) (conventional shrunken-2 (sh2) hybrid backcross conversions containing, and not containing, the sh2-i allele), however, disadvantageously yielded sweetness evaluation scores indicating a rapid starch buildup in the sh2-i hybrids, generally immediately following the prime eating stage. The sh2-i hybrids exhibited reduced sweetness within about 24 to about 48 hours immediately following the prime eating stage, with a corresponding significant sugar degradation and loss at about three days post prime eating stage.

FIG. 6 presents mean organoleptic averages for starch accumulation for conventional shrunken-2 (sh2) hybrid near isogenic lines (NILs) that do not contain the mutant shrunken-2i (sh2-i) allele in comparison with those for conventional shrunken-2 (sh2) hybrid corresponding near isogenic lines (NILs) that contain the mutant shrunken-2i (sh2-i) allele over time in Days 1-7 immediately following the prime eating stage (at a level of approximately 75% moisture). The organoleptic scores range from 1 (sweet with little or no starch taste) to 10 (very little sweetness with a considerable starch taste). FIG. 6 shows that the conventional shrunken-2 (sh2) hybrid near isogenic lines (NILs) that do not contain the mutant shrunken-2i (sh2-i) allele have significantly lower organoleptic scores (ranging from about 1 on Day 1 to about 4 on Day 7) in comparison with the conventional shrunken-2 (sh2) hybrid corresponding near isogenic lines (NILs) that contain the mutant shrunken-2i (sh2-i) allele (ranging from about 1.9 on Day 1 to about 7.9 on Day 7).

In essence, the incorporation of the shrunken-2i (sh2-i) allele into conventional sweet corn varieties is considered to be impractical due to a rapid accumulation of starch in the period of time immediately following the prime eating state, and the associated loss of holding ability and shelf life.

DESCRIPTION OF OTHER ART

U.S. Pat. No. 3,971,161 describes methods that are stated to produce hybrid sweet corn seeds in commercial quantities, increase the sugar content of sweet corn without seriously reducing the water soluble polysaccharide content, and produce seeds that provide a sweet corn suitable for processing with a minimal amount of extraneous sweeteners. It states that the sugar content of sweet corn can be increased without seriously reducing the water soluble polysaccharide by using the shrunken-2 (sh2) gene, and that combining a sweet corn which is a homozygous sugary-1 (su1) inbred with a sweet corn (homozygous su1 sh2) inbred will result in a heterozygous hybrid that has approximately 50% more sucrose, 33% more total sugars and a water soluble polysaccharide level near that of sweet corn (homozygous su 1). The high water soluble polysaccharide and sucrose levels are stated to be particularly desirable in food processing industries, such as the canning and freezing industries.

U.S. Pat. Nos. 5,589,618 and 5,650,557 describe a variant of the maize gene shrunken-2 (sh2) that is designated Sh2-m1Rev6, and a method of using that gene. Sh2-m1Rev6 is stated to encode a subunit of the ADP-glucose pyrophosphorylase (AGP) enzyme that has additional amino acids inserted in, or near, the allosteric binding site of the protein. Corn seed expressing the Sh2-m1Rev6 gene is stated to have a 15% weight increase over wild type seed, and the increase in seed weight is stated not to be associated simply with an increase in percentage starch content of the seed.

U.S. Pat. No. 5,746,023 describes a method for identifying genetic markers that are stated to be linked to alleles conferring yield potential of a crop species. By conducting genetic marker analysis of a set of current elite lines, and the ancestral population from which they were derived by decades of plant breeding, the '023 patent states that one may determine and compare the expected, and observed, allele frequencies within elite populations at numerous polymorphic loci.

U.S. Pat. No. 5,912,413 describes the starch debranching enzyme encoded by the sugary (su1) gene that is active in maize (Zea mays) endosperm, and the cDNA and gene sequences encoding this enzyme. The amino acid sequence of the enzyme is stated to be significantly similar to that of bacterial isoamylases, enzymes that hydrolyze α-(1→46) glycosidic bonds. This patent states that amino acid sequence similarity establishes su1 as a member of the α-amylase super family of starch hydrolytic enzymes. The '413 patent also discloses antibodies that are reactive with the su1 protein, methods of producing antibodies to the su1 protein, methods of producing fusion proteins including su1, and methods of producing transgenic plants with a modified su1 gene.

U.S. Pat. No. 6,184,438 B1 describes mutant alleles of the genes that encode the large subunit of AGP-glucose pyrophosphorylase in plants, methods for transforming plants with the mutant alleles, and plants that have the mutant alleles incorporated into their genome. When present in maize plants, the mutant alleles are stated to confer enhanced germination characteristics to the plants, as compared to plants that express the sh2-R genes.

U.S. Pat. No. 6,756,524 B2 describes an isolation and identification of a nucleic acid molecule that is stated to regulate fruit size and/or cell division in plants, and the protein encoded by this nucleic acid molecule. The '524 patent also describes an expression vector containing the encoding nucleic acid, and methods whereby fruit size is stated to be reduced and/or increased, and cell division is stated to be regulated, by a transformation of plants with this nucleic acid molecule. It also discusses host cells, transgenic plants and plant seeds containing this nucleic acid molecule.

U.S. Pat. No. 7,084,320 B2 describes methods for selecting a parent inbred plant line (having a particular genetic background) that has a good combining ability, for example, for the production of hybrid plant lines, from a collection of parental lines. Such a parent inbred plant line is referred to as being "an excellent combiner" in breeding experiments that are described in this patent. Upon crossing of such parent inbred plant line with another parent inbred plant line (having a different genetic background), the two parent inbred plant lines are stated to be capable of yielding a hybrid plant line with high heterosis effect, and the seeds from the crossed selected inbred lines are collected and, optionally, planted and grown to obtain the hybrid plants. The '320 patent also describes methods for determining the agronomical performance of different plant lines, including the foregoing hybrids, which it states can be performed in vitro by determining the electron flow in mitochondria under control and stress conditions. The '320 patent describes an object as being to provide a method for selecting a hybrid (or other) plant line having the highest growth and yield vigor from a collection of plant lines from the same species (variety). It describes and shows (FIG. 1) a vigor assay that it states can be used to identify plant lines that are affected in their vigor.

M. Clancy and L C Hannah, "The Mutations sh2-i and sh2-N2340 Share an Identical Intron Splice Site Mutation and are Most Likely the Same Allele," Maize Genetics Cooperation Newsletter 80 (2006), states that the mutant alleles sh2-i and sh2-N2340, which are publicly available from the Maize Stock Center (Urbana/Champaign, Ill.), were generated using EMS mutagenesis, and condition an intermediate or leaky phenotype. It further states that sh2-i and sh2-N2340 kernels are visually similar, trace to the same source, and are less severely collapsed when mature in comparison with an sh2-R reference allele. It states that sequencing established that sh2-i contains a G to A transition at the 3-terminus of intron 2 (Lal et al., Plant Physiol. 120:65-72, 1999), and that approximately 10% of sh2-i transcripts are correctly spliced utilizing the mutant intron splice site, generating a low level of adenosine diphosphate glucose pyrophosphorylase activity that results in the intermediate kernel phenotype. It states that, in order to determine whether or not the alleles sh2-i and sh2-N2340 contain the same mutation, young shoot material was harvested from germinating sh2-N2340 kernels, genomic DNA was prepared using Plant DNAZOL Reagent (Invitrogen, Carlsbad, Calif.), and DNA spanning exons 1 through 4 was amplified via PCR using the primers described by Lal et al. It states that, because sequencing of the PCR product established that sh2-i and sh2-N2340 share the same G to A transition of the final nucleotide in intron 2, it appears that the same mutation bears two different designations (i.e., there are two different names for the same mutant allele).

Although the shrunken-2i (sh2-i), sugary-1 (su1) and sugary enhancer-1 (se1) genes are known, no one to date has been able to successfully combine these genes to produce plants, plant materials and seeds having an enhanced vigor, while also retaining desirable consumer traits, such as an elevated sugar level during the period following the prime eating stage, and this has led to frustration among plant breeders, plant growers and consumers. There has, thus, been a long-felt, but unresolved, need in the industry for cost-effective, reliable, efficient and successful methods for commercially producing inbred and hybrid plants having seeds that exhibit a fuller content (i.e., more stored energy) at the dry seed stage in comparison with conventional counterpart plants, resulting in an enhanced vigor during seed germination, seedling emergence from the soil and plant development (like conventional sh2-i sweet corn), but that also retain desirable consumer traits, such as an elevated sugar level during the period following the prime eating stage, maintaining a sweet or desirable flavor of the plant, or its plant parts (seeds, fruits, vegetables, corn kernels, ears of corn, or the like). Improved growth and taste characteristics of plants, such as sweet corn, would confer a significant advancement in the commercial production of these plants.

Various commercial plant breeders and growers, such as Rogers NK (Boise, Id.) and Syngenta Seeds, Inc. (Stanton, Minn.), have tried, and failed, to successfully combine traits to achieve a plant variety that is pleasing to both producers and consumers. While Rogers NK has one commercial maize product (named "Brighton") that includes the maize shrunken-2i (sh2-i) allele in its genome, this product has not been commercially successful because the eating quality (taste, texture and the like) of this product is not desirable to consumers. Because this product does not taste good (i.e., it has a starchy, unsweet taste), it has been very undesirable to corn growers and gardeners who are planting sweet corn for consumer acceptance.

Further, none of the above references, or others that are described herein, teach or suggest the methods, plants, plant materials or seeds of the present invention.

SUMMARY OF THE INVENTION

The present invention provides unique, cost-effective, reliable, efficient and successful methods for developing and producing plants, plant materials and seeds, such as sweet corn kernels, and sweet corn, that very advantageously receive, and have, multiple very desirable attributes for consumers of these products, as well as for commercial plant growers and home gardeners, and to improved plants, plant materials and seeds that are produced in accordance with these methods. These inventive methods provide novel hybrid plants, plant materials and seeds having the mutant shrunken-2i (sh2-i) allele incorporated into their genomes, preferably sequentially along with one or more other mutant alleles, such as the sugary-1 (su1), sugary enhancer-1 (se1) and/or shrunken-2 (sh2) alleles, and that very advantageously have multiple very beneficial and desirable characteristics, generally including a smooth and creamy texture, an enhanced sugar level that results in a very desirable sweet or other taste, an extended sugar retention ability (and associated taste benefits, such as the sweet taste of sweet corn) at the post prime eating stage, a longer harvest window of the plant, a longer holding ability of the plant (ears of sweet corn and the like), and a longer shelf life of the plant before sweetness deteriorates after the prime eating stage, seeds and/or kernels that physically are fuller, and have a higher carbohydrate and water soluble polysaccharides (WSP) content, at the dry seed stage, and/or significantly enhanced vigor and fitness to the plant, plant material and/or seed during seed germination, seedling emergence from soil, and plant development.

The present invention also provides methods for incorporating the mutant sh2-i gene into the genomes of commercially acceptable (and other) sweet corn female (and other) parent lines not originally including the sh2-i gene in their genomes, and for identifying female (and other) sweet corn parent lines into which the mutant sh2-i gene has successfully been incorporated (often referred to herein as "sh2-i conversion lines").

Further, the present invention provides unique and successful construction processes for producing hybrid sweet corn (and other plant) lines having a series of multiple very desirable traits, as are described in detail herein, which are optionally, but preferably, developed using the following types of female and male sweet corn (or other plant) parent lines:

(i) a female sweet corn (or other plant) parent line containing the mutant sh2-i endosperm allele in its genome (i.e., an "sh2-i conversion line"):

preferably as a conversion of a conventional "supersweet" female parent line including the allelic combination of Su1Su1 sh2sh2 in its genome, optionally, but preferably, using molecular markers and sequentially layering the mutant sh2-i allele against a genetic background (genotype) of Su1Su1 sh2sh2 to produce, for example, a female "Su1Su1 sh2-i sh2-i conversion line" including the desired endosperm mutant allele genotype Su1Su1 sh2-i sh2-i in its genome, and produced by incorporating the mutant sh2-i endosperm gene into a conventional "supersweet" female parent Su1Su1 sh2sh2 line (i.e., including an Su1Su1 sh2sh2 genetic background or genotype); and more preferably as a conversion of a female parent line including the double homozygous recessive allelic combination of su1su1 se1se1 in its genome, such as su1su1 se1se1 or su1su1 se1se1 sh2sh2, optionally, but preferably, using molecular markers and sequentially layering the mutant sh2-i allele against a genetic background (genotype) of the homozygous recessive se1se1 and su1su1 alleles to produce, for example, a female "su1su1 se1se1 sh2-i sh2-i conversion line" including the desired endosperm mutant allele genotype su1su1 se1se1 sh2-i sh2-i in its genome, and produced by incorporating the mutant sh2-i endosperm gene into a female plant line including a homozygous recessive genotype of su1su1 se1se1 in its genome (i.e., including an su1su1 se1se1 or su1su1 se1se1 sh2sh2 genetic background or genotype); and (ii) a male sweet corn (or other plant) parent line including in its genome a single, double or triple homozygous recessive allelic construction or combination in connection with the sugary (su 1), sugary enhancer-1 (se1) and/or shrunken-2 (sh2) mutant endosperm (or other) alleles, such as the genotype Su1Su1 Se1Se1 sh2sh2 (single construction), and preferably the double homozygous recessive allelic combination su1su1 Se1 Se1 sh2sh2 or su1su1 sh2sh2, and even more preferably the triple homozygous recessive allelic combination su1su1 se1se1 sh2sh2 (with both such double and triple homozygous recessive endosperm mutant allelic combinations including the double homozygous recessive endosperm mutant su1su1 and sh2sh2 alleles).

The above female parent sweet corn (or other plant) lines express, and pass down to hybrids produced therewith (when constructed in the manner that is described herein), the very desirable traits of an enhanced seedling germination and an enhanced seedling vigor. The above male parent sweet corn (or other plant) lines, on the other hand, express, and pass down to hybrids produced therewith (when constructed in the manner that is described herein), the very desirable grower and/or consumer traits of producing sweet corn kernels (or other plant parts) that: (i) are exceptionally high in sugar (sucrose) content and, as a result, have a very sweet taste; (ii) have very tender pericarps; and (iii) have significant holding abilities (retention of higher sugars and tender kernel pericarps). These male parent traits are believed to be a result of the double recessive homozygous su1su1 and sh2sh2 genotypic endosperm mutant allelic combinations that are preferably present in both the above double and triple recessive allelic combinations of the male parent lines (double: su1su1 Se1Se1 sh2sh2 or su1su1 sh2sh2; triple: su1su1 se1se1 sh2sh2).

The above female and male parent sweet corn (or other plant) line mutant endosperm alleles, when expressed in such a manner in a sweet corn (or other plant) hybrid, very advantageously provide the hybrid with significantly enhanced growth characteristics, such as an enhanced seedling germination and an enhanced seedling vigor, in comparison with very similar or other sweet corn (or other plant) hybrids that do not have such mutant endosperm alleles expressed in this manner (i.e., that were not developed using such female and male parental lines). This is very apparent from the comparison testing data that is set forth in the "Examples" section hereinbelow, for example, as a result of testing in both the laboratory and in the field, and of organoleptic testing, of two different parent sweet corn lines or hybrid sweet corn lines that are identical, with the one exception that one includes the sh2-i endosperm mutant allele in its genome, and the other one does not.

The present invention also provides an identification and incorporation of the mutant sh2-i endosperm gene into commercially acceptable (or other) sweet corn (or other plant) parental lines to produce hybrid plants, plant materials and seeds using a combination of: (i) female parental lines including in their genome the shrunken-2i (sh2-i) mutant endosperm allele preferably incorporated into a conventional "supersweet" (Su1Su1 sh2sh2) genetic background (genotype) to provide the resulting genotype Su1Su1 sh2-i sh2-i, which is characteristic of enhanced seedling germination and enhanced seedling vigor; and (ii) male parental lines including in their genome the double (su1su1 Se1Se1 sh2sh2 or su1su1 sh2sh2) or triple (su1su1 se1 se1 sh2 sh2) (or other) homozygous recessive mutant endosperm genotypes, which are characteristic of being exceptionally high in sugar, thereby providing a sweet taste to the products, with very tender kernel pericarps. The resulting hybrid products have multiple beneficial traits, including a significantly enhanced vigor and fitness to the plant, plant material and/or seed during germination, seedling emergence from the soil, and plant development. This benefit is coupled with adequate sugar retention, product holding ability and shelf life at peak eating stage, for example, at approximately 75% kernel moisture, and through at least a 48-hour harvest window (and often longer).

In one aspect, the present invention provides a method for producing a hybrid plant, plant material or seed that has an enhanced vigor in comparison with a conventional mutant shrunken-2 (sh-2) or mutant shrunken-2i (sh2-i) hybrid plant, plant material or seed, and an enhanced ability to retain sugar over a period of time immediately following a prime eating stage thereof, in comparison with a conventional mutant sugary-1 (su1) or shrunken-2i (sh2-i) hybrid plant, plant material or seed, comprising optionally using one or more molecular markers to preferably, but optionally, sequentially include in the genome of the plant, plant material or seed a mutant shrunken-2i (sh2-i) endosperm allele and one or more other mutant endosperm alleles that confer the foregoing characteristics to the plant, plant material or seed. Although such use of molecular markers in connection with such sequential layering of mutant endosperm alleles in the genome of the plant, plant material or seed, are both very desirable, and are preferable, as is discussed herein in detail, particularly in connection with Example 4 and Example 8 hereinbelow, such process step is optional.

In another aspect, the present invention provides a method for producing a hybrid plant, plant, plant material or seed that has both an enhanced vigor in comparison with a conventional mutant shrunken-2 (sh-2) or shrunken-2i (sh2-i) hybrid plant, plant, plant material or seed, and an enhanced ability to retain sugar over a period of time immediately following a prime eating stage thereof (or one or more other desirable traits), in comparison with a conventional mutant sugary-1 (su1) or shrunken-2i (sh2-i) hybrid plant, plant, plant material or seed, comprising the following steps in any suitable order:

(a) identifying an inbred plant line that includes one or more desired mutant alleles in its genome, singly or in combination, including, but not limited to, the sugary 1 (su1), sugary enhancer-1 (se1) and shrunken 2 (sh2) mutant alleles, optionally using molecular markers;

(b) constructing one or more female near isogenic plant lines (NILs) having a desired genotype, including, but not limited to the following triple mutant endosperm allelic combinations:
  (i) Su1Su1 Se1Se1 sh2sh2;
  (ii) Su1Su1 se1se1 sh2sh2; or
  (iii) su1su1 se1se1 sh2sh2 (a triple homozygous recessive mutant endosperm allelic combination);
for use as a genetic background (genotype) in a combination with a female parental plant line that has a shrunken-2i (sh2-i) mutant allele in its genome;

(c) optionally, incorporating a shrunken-2i (sh2-i) mutant allele into the genome of the female near isogenic plant line having a desired genetic background of step (b), for example including a genotype of su1su1 se1se1 sh2sh2 or su1su1 se1se1, optionally, using one or more molecular markers;

(d) selecting a female near isogenic plant line of step (c) having a shrunken-2i (sh2-i) allele layered over a genetic background (genotype) of su1su1 se1se1, or of one or more other desirable mutant alleles, individually or in combination, in its genome (a female "converted near isogenic line");

(e) optionally, crossing the selected female converted near isogenic plant line of step (d) with a male plant line including a triple homozygous recessive mutant endosperm allelic construction in its genome, wherein such homozygous recessive mutant endosperm allelic construction is su1su1 se1se1 sh2sh2 (or some other triple homozygous recessive allelic construction that can provide a hybrid plant with a high or enhanced eating quality) in its genome to produce a hybrid plant having one or more desired grower and/or consumer traits;

(f) optionally, examining a physical appearance (phenotype) of seeds (or kernels) resulting from the plants of step (d) and/or step (e) for characteristics such as smoothness, fullness and/or relative weight (in comparison with seeds or kernels from conventional or other plants);

(g) optionally, conducting warm, cold and/or other laboratory and/or field germinations of seeds (or kernels) resulting from the plants of step (d) and/or step (e) to verify that such seeds have one or more desired consumer and/or grower traits, such as an enhanced germination, seedling emergence and plant growth performance, and vigor, that is associated with a mutant shrunken-2i (sh2-i) allele; and (h) optionally, conducting one or more organoleptic taste, pericarp tenderness and/or other tests on plants (or parts thereof, such as ears of corn) that are grown from seeds (or kernels) produced by plants of step (d) and/or step (e) to determine their taste, pericarp tenderness and/or other organoleptic characteristics, optimally examining the overall physical and horticultural traits (i.e., phenotype) that are consistent with plants that express one or more desired grower and/or consumer traits.

By following the above processes, a regulation of carbohydrate accumulation and pericarp tenderness (among other traits) can be manipulated in a plant, plant material and/or seed, and a mutant shrunken-2i (sh2-i) allele can be incorporated into the genome of the plant, plant material or seed to give it the desired production and consumer traits. Plants, plant materials and seeds can be grown that exhibit a fuller content at the dry seed stage in comparison with other plant varieties or lines, and result in an enhanced vigor during seed germination, seedling emergence from the soil and/or plant development, and that also maintain an elevated sugar level, resulting in a sweet or other desirable flavor of the plant, plant material and/or seed over a period of time immediately following the prime eating stage thereof. Those having ordinary skill in the art may determine the number of times that a particular step in the above process, such as the backcrossing of near isogenic lines, should or must be performed in order to achieve a successful result of the process. As is indicated above, some of these steps are preferably performed multiple times.

In another aspect, the present invention provides a hybrid plant, plant, plant material or seed that has an enhanced vigor in comparison with a conventional mutant shrunken-2 (sh-2) or shrunken-2i (sh2-i) hybrid plant, plant, plant material or seed, and an enhanced ability to retain sugar over a period of time immediately following a prime eating stage thereof, in comparison with a conventional mutant sugary-1 (su 1) or shrunken-2i (sh2-i) hybrid plant, plant, plant material or seed, consisting of steps (a) through (h) above, in any suitable order.

In yet another aspect, the present invention provides a plant seed that is produced by any one of the methods that is described above (or otherwise herein).

In another aspect, the present invention provides a hybrid or other plant seed comprising a genome including the shrunken-2i (sh2-i) allele that is sequentially layered across a genetic background of one or more additional mutant alleles providing the plant seed with one or more desirable traits, wherein the plant seed is conferred with an enhanced vigor in comparison with a conventional mutant shrunken-2 (sh-2) or shrunken-2i (sh2-i) plant seed, and an enhanced ability to retain sugar over a period of time immediately following a prime eating stage thereof, in comparison with a conventional mutant sugary-1 (su1) or shrunken-2i (sh2-i) plant seed.

In still another aspect, the present invention provides a hybrid or other plant seed consisting of a genome including the shrunken-2i (sh2-i) allele that is sequentially layered across a genetic background of one or more additional mutant alleles providing the plant seed with one or more desirable traits, wherein the plant seed is conferred with an enhanced vigor in comparison with a conventional mutant shrunken-2 (sh-2) or shrunken-2i (sh2-i) plant seed, and an enhanced ability to retain sugar over a period of time immediately following a prime eating stage thereof, in comparison with a conventional mutant sugary-1 (su1) or shrunken-2i (sh2-i) plant seed.

In another aspect, the present invention provides a plant or plant material that is produced by any one of the methods that is described above (or otherwise herein).

In yet another aspect, the present invention provides a hybrid or other plant or plant material comprising a genome including the shrunken-2i (sh2-i) allele that is sequentially layered across a genetic background of one or more additional mutant alleles providing the plant or plant material with one or more desirable traits, wherein the plant or plant material is conferred with an enhanced vigor in comparison with a conventional mutant shrunken-2 (sh-2) or shrunken-2i (sh2-i) plant or plant material and an enhanced ability to retain sugar over a period of time immediately following a prime eating stage thereof, in comparison with a conventional mutant sugary-1 (su1) or shrunken-2i (sh2-i) plant or plant material.

In another aspect, the present invention provides a hybrid or other plant or plant material consisting of a genome including the shrunken-2i (sh2-i) allele that is sequentially layered across a genetic background of one or more additional mutant alleles providing the plant or plant material with one or more desirable traits, wherein the plant or plant material is conferred with an enhanced vigor in comparison with a conventional mutant shrunken-2 (sh-2) or a conventional mutant shrunken-2i (sh2-i) plant or plant material and an enhanced ability to retain sugar over a period of time immediately following a prime eating stage thereof, in comparison with a conventional mutant sugary-1 (su1) or conventional shrunken-2i (sh2-i) plant or plant material.

In yet another aspect, the present invention provides a method for producing a hybrid plant, plant, plant material or seed that has both an enhanced vigor in comparison with a conventional mutant shrunken-2 (sh-2) or shrunken-2i (sh2-i) hybrid plant, plant, plant material or seed, and an enhanced ability to retain sugar over a period of time immediately following a prime eating stage thereof (or one or more other desirable traits), in comparison with a conventional mutant sugary-1 (su 1) or shrunken-2i (sh2-i) hybrid plant, plant, plant material or seed, comprising the following steps in any suitable order:

(a) identifying an inbred plant line that includes one or more desired mutant alleles in its genome, singly or in combination, including, but not limited to, the sugary 1 (su1), sugary enhancer-1 (se1) and shrunken 2 (sh2) mutant endosperm alleles, optionally using molecular markers;

(b) constructing one or more female near isogenic plant lines (NILs) having a desired genotype, including, but not limited to the following triple allelic combinations:
  (i) Su1Su1 Se1Se1 sh2sh2;
  (ii) Su1Su1se1se1 sh2sh2; or
  (iii) su1su1 se1se1 sh2sh2 (a triple homozygous recessive mutant endosperm allelic combination);
for use as a genetic background (genotype) in a combination with a female parental plant line that includes a shrunken-2i (sh2-i) mutant allele in its genome;

(c) incorporating a shrunken-2i (sh2-i) mutant allele into the genome of the female near isogenic plant line having a desired genetic background (genotype) of step (b), optionally, using one or more molecular markers, wherein the desired genetic background is su1su1 se1se1 sh2sh2, su1su1 se1se1, Su1Su1se1se1 sh2sh2, Su1Su1 se1se1, Su1Su1 sh2sh2 or another desirable genetic background;

(d) selecting a female near isogenic plant line of step (c) having a mutant shrunken-2i (sh2-i) allele incorporated into a genetic background (genotype) of Su1Su1 sh2 sh2, or of one or more other desirable mutant alleles, individually or in combination, wherein the female near isogenic plant line includes an endosperm allelic combination of Su1Su1 sh2-i sh2-i, or another desirable endosperm allelic combination, in its genome (a female "converted near isogenic line"), which is characteristic of an enhanced seedling germination and vigor;

(e) optionally, crossing the selected female converted near isogenic plant line of step (d) with a male plant line including a homozygous recessive endosperm allelic construction in its genome, wherein such homozygous recessive endosperm allelic construction is Su1Su1Se1Se1 sh2sh2, su1su1 Se1Se1 sh2 sh2, su1su1 se1se1 sh2 sh2, or another homozygous recessive endosperm allelic combination that can provide a hybrid plant with a high or enhanced eating quality, to produce a hybrid plant having one or more desired grower traits, consumer traits, or both traits;

(f) optionally, examining a physical appearance (phenotype) of seeds (or kernels) resulting from the plants of step (d) and/or step (e) for characteristics such as smoothness, fullness and/or relative weight (in comparison with seeds or kernels from conventional or other plants);

(g) optionally, conducting one or more warm, cold, or both warm and cold, laboratory, field, or laboratory and field, germinations of seeds (or kernels) produced by the plants of step (d) and/or step (e) to verify that such seeds have one or more desired consumer and/or grower traits, such as an enhanced germination, seedling emergence and plant growth performance, and vigor, that is associated with a mutant shrunken-2i (sh2-i) allele, or a combination thereof; and (h) optionally, conducting one or more organoleptic taste, pericarp tenderness and/or other tests on plants, on plant parts (such as ears of corn), or a combination thereof, that are grown from seeds (or kernels) produced by the plants of step (d) and/or step (e) to determine their taste, pericarp tenderness and/or other organoleptic characteristics, optimally examining the overall physical and horticultural traits (i.e., phenotype) that are consistent with plants that express one or more desired grower and/or consumer traits.

As with the other processes that are described hereinabove, by following the process directly above, a regulation of carbohydrate accumulation and pericarp tenderness (among other desirable grower and/or consumer traits) can be manipulated in a plant, plant material and/or seed, and a mutant shrunken-2i (sh2-i) allele can be incorporated into the genome of the plant, plant material or seed to give it the desired production and consumer traits. Plants, plant materials and seeds can be grown that exhibit a fuller content at the dry seed stage in comparison with other plant varieties or lines, and result in an enhanced vigor during seed germination, seedling emergence from the soil and/or plant development, and that also maintain an elevated sugar level, resulting in a sweet or other desirable flavor of the plant, plant material and/or seed over a period of time immediately following the prime eating stage thereof. Those having ordinary skill in the art may determine the number of times that a particular step in the above process, such as the backcrossing of near isogenic lines, should or must be performed in order to achieve a successful result of the process. As is indicated above, some of these steps are preferably performed multiple times.

In another aspect, the present invention provides a hybrid plant, plant, plant material or seed that has an enhanced vigor in comparison with a conventional mutant shrunken-2 (sh-2) or shrunken-2i (sh2-i) hybrid plant, plant, plant material or seed, and an enhanced ability to retain sugar over a period of time immediately following a prime eating stage thereof, in comparison with a conventional mutant sugary-1 (su1) or shrunken-2i (sh2-i) hybrid plant, plant, plant material or seed, consisting of steps (a) through (h) above in any suitable order.

In yet another aspect, the present invention provides a plant seed that is produced by any one of the methods that is described above (or otherwise herein).

In another aspect, the present invention provides a plant or plant material that is produced by any one of the methods that is described above (or otherwise herein).

In still another aspect, the present invention provides a method for producing a hybrid plant, plant material, or seed comprising crossing an inbred plant line that is homozygous recessive for the mutant shrunken2-i endosperm allele, and also homozygous recessive for one or more other endosperm alleles, as the female parent plant line with a different male parent plant line, which may be, for example, a conventional male parent sweet corn or other plant line.

BRIEF DESCRIPTION OF THE DRAWINGS

FIG. 2 shows representative changes in endosperm sucrose levels over time for the three different genetic types.

FIG. 4 shows representative changes in pericarp levels over time for the three different genetic types.

FIG. 10 (FIGS. 10A-10U) is a molecular map of samples of individual inbred NILs that were prepared in the experiments that are described in Example 1.

BRIEF DESCRIPTION OF THE SEQUENCES

Figure 1:
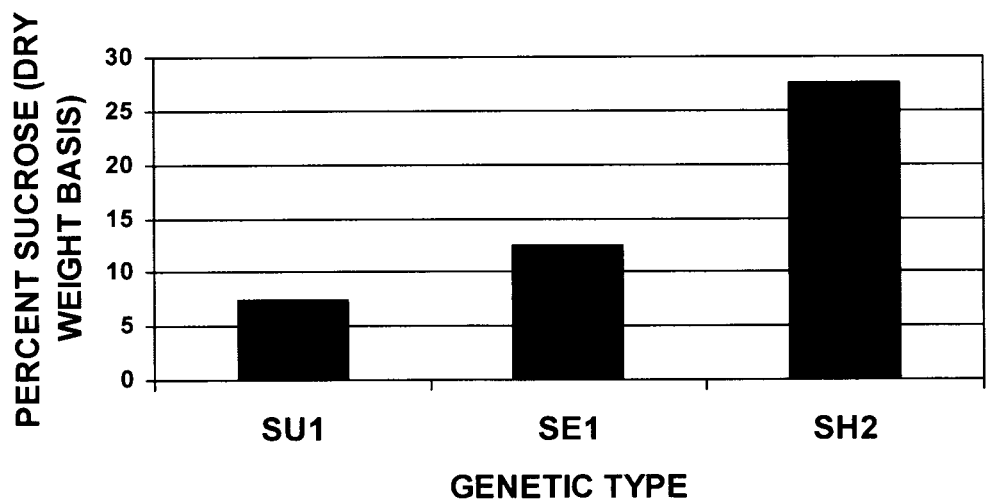
FIG. 1 is a bar graph that provides a generalized comparison of representative endosperm sucrose levels for the conventional sugary-1 (su1), sugary enhancer-1 (se1) and shrunken-2 (sh2) genetic mutant lines at the prime eating stage (at a level of approximately 75% moisture).
Figure 2:
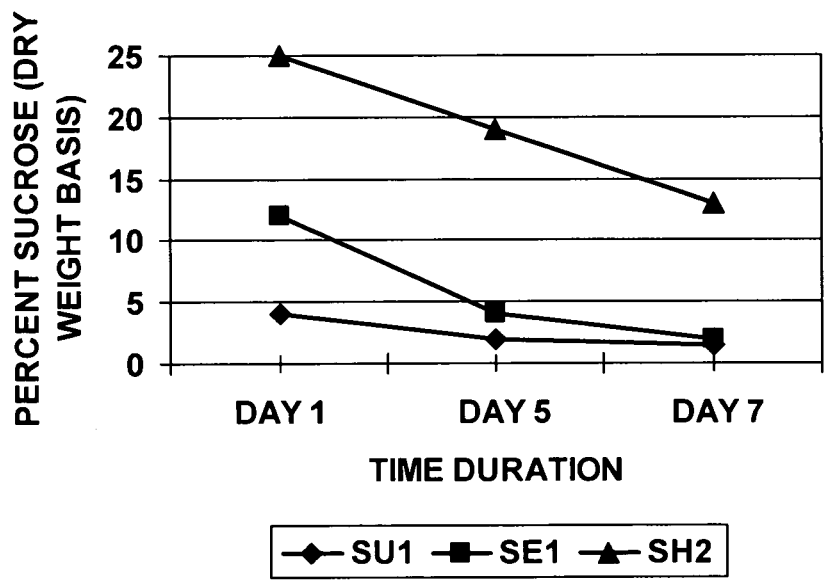
FIG. 2 is a line graph that shows the relative endosperm sugar retention or "holding ability" at room temperature for the conventional sugary-1 (su1), sugary enhancer-1 (se1) and shrunken-2 (sh2) genetic mutant lines at the prime eating stage (at a level of approximately 75% moisture) through a seven day interval (Days 1-7).
Figure 3:
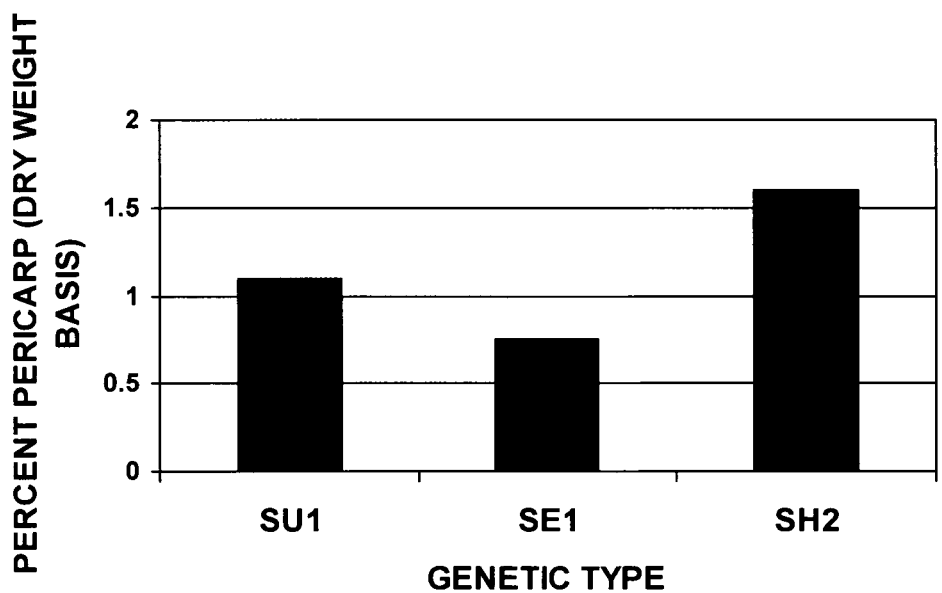
FIG. 3 is a bar graph that provides a comparison of representative pericarp levels for the conventional sugary-1 (su1), sugary enhancer-1 (se1) and shrunken-2 (sh2) genetic mutant lines at the prime eating stage (at a level of approximately 75% moisture).
Figure 4:
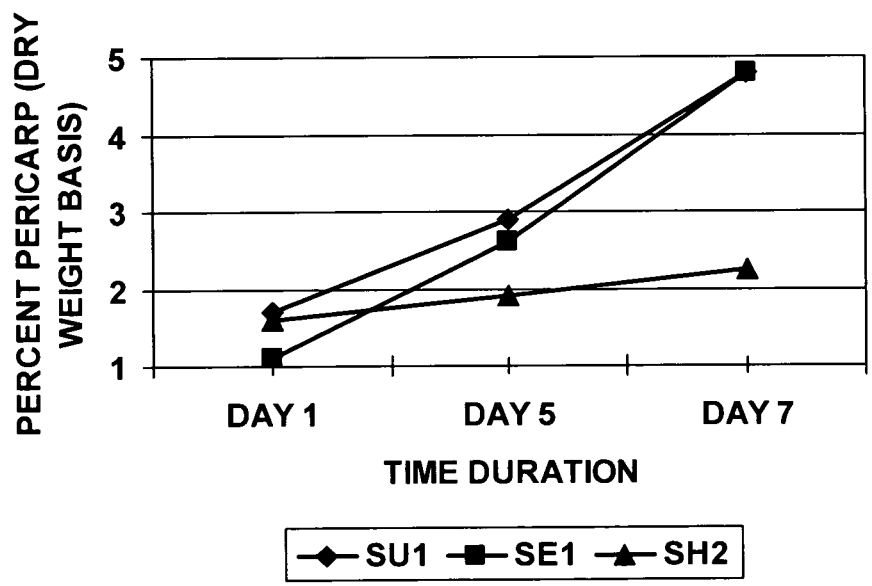
FIG. 4 is a line graph that shows the relative pericarp levels at room temperature for the conventional sugary-1 (su1), sugary enhancer-1 (se1) and shrunken-2 (sh2) genetic mutant lines at the prime eating stage (at a level of approximately 75% moisture) through a seven day interval (Days 1-7).
Figure 5:
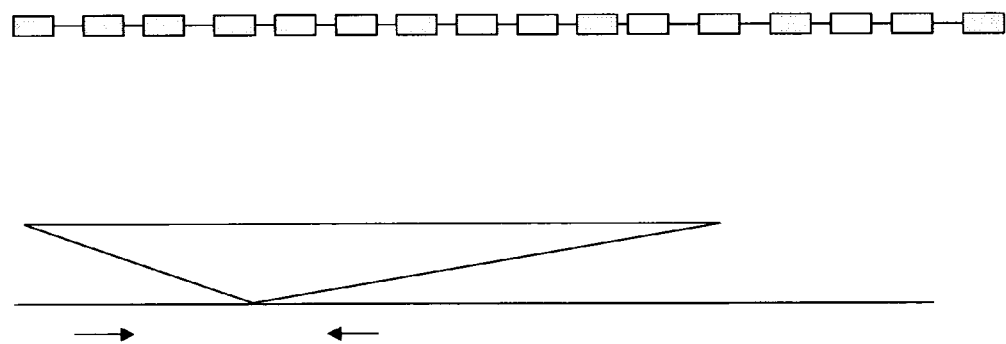
FIG. 5 is a diagram of the wildtype sh2 gene (sh2-R), which is composed of 16 exons (represented by boxes in FIG. 5) that are separated by introns (represented by lines in FIG. 5). This gene is approximately 6,000 base pairs long. The sh2-R gene has a large (at least 7,800 base pair) insertion in the intron 2-exon 4 region (represented by the triangle in FIG. 5). Primers (represented by the arrows in FIG. 5) bordering this insertion will not yield a Polymerase Chain Reaction (PCR) product because of the large size of the insertion. In contrast, the sh2-i gene has a single base pair change at the end of intron 2, and primers flanking the insertion site of sh2-i will yield a PCR product.
Figure 6:
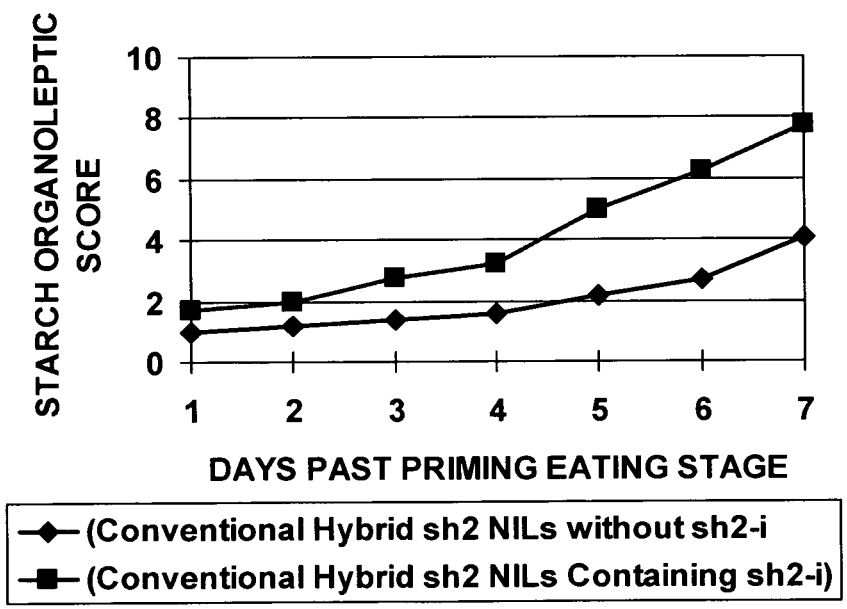
FIG. 6 is a line graph that shows mean starch organoleptic scores (organoleptic averages for starch accumulation) for conventional hybrid shrunken-2 (sh2) near isogenic lines (NILS), either containing, or not containing, the sh2-i allele over time in days 1-7 past the prime eating stage (at a level of approximately 75% moisture).

SEQ ID NO. 1 is the 7739 base pair genomic nucleotide sequence of a wild type Shrunken-2 (sh2) allele of *Zea Mays*, which is also published in U.S. Pat. No. 6,184,438 B1. (FIG. 1 of U.S. Pat. No. 6,184,438 B1, which is incorporated herein in its entirety by reference, also shows the genomic nucleotide sequence of a wild type Shrunken-2 (sh2) allele of *Zea Mays*. Introns are indicated by lower case letters. Base number 1 is the transcription start site. The arrow indicates the 3'-end of cDNA. Putative TATA, RY dyad and enhancer sequences are underlined.)

SEQ ID NO. 2 is the cDNA sequence encoding the sugary-1 (su1) allele of *Zea Mays*, which is also published in U.S. Pat. No. 5,912,413. The 2712 base pair nucleotide sequence of the su1 cDNA clone includes a sequence of 14 consecutive T residues located at one end of the clone, identifying the polyadenylation site and the 3' end of the mRNA. A continuous open reading frame (ORF) of 789 codons begins 88 nucleotides from the 5' end of the cDNA clone and terminates 240 nucleotides prior to the poly(A) adenylation site. This ORF corresponds to a polypeptide of 789 amino acids (SEQ ID NO. 3). Comparison of the cDNA and a partial genomic sequence (SEQ ID NO: 4) identifies four exons and introns in the genomic DNA. The four exons extend from nucleotide 658 to nucleotide 1107, nucleotide 1352 to nucleotide 1536, nucleotide 1657 to nucleotide 1753, and nucleotide 2076 to nucleotide 2227. The exon sequences or the full sequence of SEQ ID NO: 4 can be used as probes to obtain the full length genomic sequence by methods that are well known by those having ordinary skill in the art.

SEQ ID NO. 3 is an amino acid translation of the sugary-1 (su1) nucleotide sequence of the cDNA clone that is shown in SEQ ID NO. 2, which is also published in U.S. Pat. No. 5,912,413.

SEQ ID NO. 4 is a partial sugary-1 (su1) genomic nucleotide sequence, which is also published in U.S. Pat. No. 5,912,413.

SEQ ID NO. 5 is the deduced amino acid sequence of su1 (SEQ ID NO. 4), which is also published in U.S. Pat. No. 5,912,413.

SEQ ID NO. 6 is a nucleotide sequence of the primer umc1551 (a primer for molecular markers for the sugary enhancer-1 (se1) allele on chromosome 2).

SEQ ID NO. 7 is a nucleotide sequence of the primer umc1551 (a primer for molecular markers for the sugary enhancer-1 (se1) allele on chromosome 2).

SEQ ID NO. 8 is a nucleotide sequence of the primer bnlg1520 (a primer for molecular markers for the sugary enhancer-1 (se1) allele on chromosome 2).

SEQ ID NO. 9 is a nucleotide sequence of the primer bnlg1520 (a primer for molecular markers for the sugary enhancer-1 (se1) allele on chromosome 2).

SEQ ID NO. 10 is a nucleotide sequence of the primer phi427434 (a primer for molecular markers for the sugary enhancer-1 (se1) allele on chromosome 2).

SEQ ID NO. 11 is a nucleotide sequence of the primer phi427434 (a primer for molecular markers for the sugary enhancer-1 (se1) allele on chromosome 2).

SEQ ID NO. 12 is a nucleotide sequence of the primer umc2077 (a primer for molecular markers for the sugary enhancer-1 (se1) allele on chromosome 2).

SEQ ID NO. 13 is a nucleotide sequence of the primer umc2077 (a primer for molecular markers for the sugary enhancer-1 (se1) allele on chromosome 2).

SEQ ID NO. 14 is a nucleotide sequence of the primer umc2174 (a primer for molecular markers for the shrunken-2 (sh2) allele on chromosome 3).

SEQ ID NO. 15 is a nucleotide sequence of the primer umc2174 (a primer for molecular markers for the shrunken-2 (sh2) allele on chromosome 3).

SEQ ID NO. 16 is a nucleotide sequence of the primer dupssr33 (a primer for molecular markers for the shrunken-2 (sh2) allele on chromosome 3).

SEQ ID NO. 17 is a nucleotide sequence of the primer dupssr33 (a primer for molecular markers for the shrunken-2 (sh2) allele on chromosome 3).

SEQ ID NO. 18 is a nucleotide sequence of the primer bmc1257 (a primer for molecular markers for the shrunken-2 (sh2) allele on chromosome 3).

SEQ ID NO. 19 is a nucleotide sequence of the primer bmc1257 (a primer for molecular markers for the shrunken-2 (sh2) allele on chromosome 3).

SEQ ID NO. 20 is a nucleotide sequence of the primer umc2277 (a primer for molecular markers for the shrunken-2 (sh2) allele on chromosome 3).

SEQ ID NO. 21 is a nucleotide sequence of the primer umc2277 (a primer for molecular markers for the shrunken-2 (sh2) allele on chromosome 3).

SEQ ID NO. 22 is a nucleotide sequence of the primer phi295450 (a primer for molecular markers for the sugary-1 (su1) allele on chromosome 4).

SEQ ID NO. 23 is a nucleotide sequence of the primer phi295450 (a primer for molecular markers for the sugary-1 (su1) allele on chromosome 4).

SEQ ID NO. 24 is a nucleotide sequence of the primer phi308090 (a primer for molecular markers for the sugary-1 (su1) allele on chromosome 4).

SEQ ID NO. 25 is a nucleotide sequence of the primer phi308090 (a primer for molecular markers for the sugary-1 (su1) allele on chromosome 4).

SEQ ID NO. 26 is a nucleotide sequence of the primer phi076 (a primer for molecular markers for the sugary-1 (su1) allele on chromosome 4).

SEQ ID NO. 27 is a nucleotide sequence of the primer phi076 (a primer for molecular markers for the sugary-1 (su1) allele on chromosome 4).

SEQ ID NO. 28 is a nucleotide sequence of the primer phi079 (a primer for molecular markers for the sugary-1 (su1) allele on chromosome 4).

SEQ ID NO. 29 is a nucleotide sequence of the primer phi079 (a primer for molecular markers for the sugary-1 (su1) allele on chromosome 4).

The sequences that are present in SEQ ID NOS. 1-29 use abbreviations that are described in the World Intellectual Property Organization (WIPO) Handbook on Industrial Property Information and Documentation, Standard ST.25, which is hereby incorporated herein by reference in its entirety.

DETAILED DESCRIPTION OF THE PREFERRED EMBODIMENTS

The present invention may be understood more readily by reference to the following detailed description of the preferred embodiments of the invention, and to the examples included therein.

DEFINITIONS

For purposes of clarity, various terms and phrases that are used throughout this specification and the appended claims are defined in the manner that is set forth below. If a term or phrase that is used in this specification, or in the appended claims, is not defined below, or otherwise in this specification, the term or phrase should be given its ordinary meaning.

The term "agronomy" as is used herein means the science of crop production.

The term "allele" as is used herein refers to one of multiple alternative form of a gene (one member of a pair) that is located at a specific position or locus on a specific chromosome, and controls the same phenotype (with potentially differing effects). Alleles are variants of a gene that produce different traits in a gene's characteristics, and can differ in either coding sequences or non-coding sequences.

The phrase "amino acid" as is used herein means a molecule that generally contains the basic amino group ($NH_2$), the acidic carboxylic group (COOH), a hydrogen atom (—H) and an organic side group (R) attached to the carbon atom, thus having the basic formula of $NH_2CHRCOOH$. Amino acids are the building blocks of proteins in which each is coded for by a codon and linked together through peptide bonds. More than 100 amino acids have been found to occur naturally, with each of them differing in their R group. Twenty of them are involved in making up a protein, and are classified as whether they are non-essential or essential. Non-essential amino acids include alanine, arginine, aspartic acid, asparagine, cysteine, glutamic acid, glutamine, glycine, proline, serine and tyrosine. Essential amino acids include histidine, isoleucine, leucine, lysine, methionine, phenylalanine, threonine, tryptophan and valine. The abbreviations for amino acids are well known by those having ordinary skill in the art.

The phrase "backcross" as is used herein means to cross (a hybrid or other plant) with one of its parents, or with an individual that is genetically identical or similar to one of its parents. It is a cross of an $F_1$ to either parent used to generate it.

The term "breeding" as is used herein means the science and/or art of manipulating the heredity of an organism for a specific purpose.

The term "carbohydrates" as is used herein means simple organic compounds comprising carbon, oxygen and hydrogen, generally with many hydroxyl groups added (usually one on each carbon atom that is not part of the aldehyde or ketone functional group). The basic carbohydrate units are monosaccharides, such as glucose, galactose and fructose. Carbohydrates have numerous roles in living things, such as the storage and transport of energy (e.g., starch or glycogen) and structural components (e.g., cellulose in plants). They serve as energy stores, fuels, and metabolic intermediates. Ribose and deoxyribose sugars form part of the structural framework of RNA and DNA. Polysaccharides are structural elements that are present in the cell walls of plants. Carbohydrates are linked to many proteins and lipids, where they play key roles in mediating interactions between cells and interactions between cells and other elements in the cellular environment. Monosaccharides can be linked together into polysaccharides in a large variety of ways.

The term "cellular respiration" as is used herein means a series of metabolic processes that generally take place within a cell in which biochemical energy is harvested from an organic substance, such as glucose, and is stored as energy carriers (ATP) for use in energy-requiring activities of the cell. It consists of glycolysis, citric acid cycle or Krebs Cycle, and oxidative phosphorylation. The cell appears to "respire" in a way that it takes in molecular oxygen (as an electron acceptor) and releases carbon dioxide (as an end product) (an aerobic process). Cellular respiration is essential to both eukaryotic and prokaryotic cells because biochemical energy is produced to fuel many metabolic processes, such as biosynthesis, locomotion, transportation of molecules across membranes, and the like. While the entire process generally occurs in the cytoplasm of prokaryotes, in eukaryotes, generally glycolysis occurs in the cytoplasm, whereas the Krebs Cycle and oxidative phosphorylation occur in the mitochondrion. While prokaryotic cells can generally yield a maximum of 38 ATP molecules, eukaryotic cells can generally yield a maximum of 36 ATP molecules.

The phrase "coding sequence" as is used herein refers to a portion of a gene or an mRNA that codes for a protein.

The term "codon" as is used herein means a set of three adjacent nucleotides (triplets), in mRNA that base-pair with the corresponding anticodon of tRNA molecule that carries a particular amino acid, hence specifying the type and sequence of amino acids for protein synthesis. For example, GCC (Guanine-Cytocine-Cytocine)→alanine, GUU (Guanine-Uracil-Uracil)→valine, CUA (Cytosine-Uracil-Adenine)→leucine and UCA (Uracil-Cytosine-Adenine)→serine.

The phrases "complimentary DNA" and "cDNA" as are used herein mean a single stranded DNA molecule that is complimentary to a specific RNA molecule, and that is synthesized from it. Complimentary DNAs are important laboratory tools as DNA probes and for isolating and studying various genes.

The phrase "conventional mutant hybrid plant, plant material, seed, line or variety" as is used herein in connection with a sugary-1 (su1), sugary enhancer-1 (se1), shrunken-2 (sh2), shrunken-2i (sh2-i) or other mutant allele means that the hybrid plant, plant material, seed, line or variety is a typical hybrid plant, plant material, seed, line or variety that generally only includes one mutant allele in its genome that confers the traits that are described herein, rather than a sequential or other combination of two or more mutant alleles, for example, one that includes the mutant shrunken-2i (sh2-i) allele in its genome, but not the sugary-1 (su1), sugary enhancer-1 (se1) or shrunken-2 (sh2) mutant alleles, or one that includes the mutant sugary-1 (su1) allele in its genome, but not the sugary enhancer-1 (se1), shrunken-2 (sh2) or shrunken-2i (sh2-i) mutant alleles.

The terms "corn" and "maize" as is used herein means any of numerous cultivated forms of a widely grown, usually tall annual cereal grass (*Zea mays*) bearing grains or kernels on large ears, and includes the numerous varieties of sweet corn and supersweet corn. The grains or kernels of this plant may be used as food for humans and livestock, or for the extraction of an edible oil or starch. The kernels may be eaten raw or cooked, and may be canned, frozen and/or stored in other manners that are known by those of ordinary skill in the art.

The terms "cross," "crossing," "interbreeding" and "crossbreeding" as are used herein mean the act of mixing different species or varieties of plants to produce hybrids. A monohybrid cross is a breeding experiment between parental generation organisms that differ in one trait. In a monohybrid cross, there is generally a genetic cross between parents that differ in the alleles they possess for one particular gene, with one parent having two dominant alleles, and the other parent having two recessive alleles. All of the offspring (monohybrids) then have one dominant and one recessive allele for that gene (i.e. they are hybrid at that one locus). Crossing between these offspring yields a characteristic 3:1 (monohybrid) ratio in the following generation of dominant:recessive phenotypes. For example, the allele for green pod color (G) is dominant, and the allele for yellow pod color (g) is recessive. The cross-pollination between a parental generation green pod plant and a parental generation yellow pod plant results in all green offspring (i.e., all genotypes are Gg). A dihybrid cross is a breeding experiment between parental generation organisms that differ in two traits. In a dihybrid cross, there is generally a genetic cross between parents that differ in two characteristics, controlled by genes at different loci. Gregor Mendel performed a dihybrid cross using pea plants and the characteristics of seed color and texture. The parental plants had either smooth yellow seeds (SSYY) (the dominant characteristics) or wrinkled green seeds (ssyy) (the recessive characteristics). All of the offspring had smooth yellow seeds, being heterozygous (SsYy) for the two alleles. Crossing between these offspring produced an $F_2$ generation of plants with smooth yellow, smooth green, wrinkled yellow, and wrinkled green seeds in the ratio 9:3:3:1. Mendel used these results as the basis for his Law of Independent Assortment. A trihybrid cross is a breeding experiment between parental generation organisms that differ in three traits, and so forth.

The term "crop" as is used herein means the periodic, such as annual or seasonal, yield of any plant that is grown in significant quantities to be harvested as food, as livestock fodder, as fuel or for any other economic (or other) purpose. Many types of crops are used for industrial purposes, for example, they are grown and harvested for the sole purpose of making profit and feeding people, and are grown in large quantities in certain areas that are suitable for growing crops.

The term "dominant" as is used herein means an allele or a gene that is expressed in an organism's phenotype, generally masking the effect of the recessive allele or gene, when present. It is a phenotype that is expressed in an organism whose genotype may be either homozygous or heterozygous for the corresponding allele. In genetics, the dominant allele or gene is the one that determines the phenotype of an organism. Its effects are readily recognized in comparison with the effects of the recessive allele or gene. Usually, a dominant allele is symbolized with a capital letter, and a recessive allele is symbolized with a small letter, for example: Hh (where H refers to the dominant allele and h refers to the recessive allele).

The phrase "dry seed stage" as is used herein means the first temporal event in the germination of a plant, such as sweet corn, and in which the seed or kernel contains a moisture content that is generally less than about 12%.

The phrases "DNA probe," "gene probe" and "probe" as are used herein mean a single-stranded DNA molecule used in laboratory experiments to detect the presence of a complimentary sequence among a mixture of various single-stranded DNA molecules.

The phrase "DNA sequencing" as is used herein means a determination of the order of nucleotides in a specific DNA molecule.

The phrases "Duncan's New Multiple Range Test" and "MRT" as are used herein mean a multiple comparison statistical procedure that uses the studentized range statistic $q_r$ to compare sets of means, and is particularly protective against false negative (Type II) error. This test is commonly used in agronomy and in other types of agricultural research, and is well known by those having ordinary skill in the art. Additional information about this test is present in D. B. Duncan, "Multiple Range and Multiple F Tests," Biometrics 11:1-42, 1955. Statistical procedures that are employed herein, and related calculations, may be performed on computers in a manner, and using software, that is known by those having ordinary skill in the art.

The term "embryo" as is used herein means a young plant developed from an ovum sexually or asexually and, in seed plants, contained within the seed.

The term "endosperm" as is used herein means the nutritive tissue that is found in many seeds of plants, and that surrounds the embryo within such seeds. It supplies nutrients to the embryo. The endosperm is generally the site of most starch deposition during kernel development in maize, and endosperm starch content comprises approximately 70% of the dry weight of the kernel or seed.

The term "energy" as is used herein means the ability to do work or produce change. Energy exists in different forms, but is neither created nor destroyed. It simply converts to another form, and can be expressed in joules or ergs. Energy is often stored by cells in biomolecules, such as carbohydrates (sugars) and lipids. The energy is generally released when these molecules have been oxidized during cellular respiration, and is carried and transported by ATP, an energy-carrier molecule.

The term "enzyme" as is used herein means a protein (or protein-based molecule) that generally speeds up a chemical reaction in a living organism, such as a plant. Enzymes generally act as catalysts for specific chemical reactions, converting a specific set of reactants (substrates) into specific products. Enzyme generally have a characteristic sequence of amino acids that fold to produce a specific three-dimensional structure, which gives the molecule unique properties, and are usually classified and named according to the reaction that they catalyze.

The term "epistasis" as is used herein means that a mutation in one gene masks the expression of a different gene. (In contrast, with dominance, one allele of a gene masks the expression of another allele of the same gene.)

The term "exon" as is used herein refers to those portions of a genomic DNA sequence that will be represented in a final, mature mRNA (i.e., a contiguous segment of genomic DNA that codes for a polypeptide in a gene). The term "exon" may also refer to equivalent segments in a final RNA. Exons may include coding sequences, a 5' untranslated region and/or a 3' untranslated region.

The term "express" as is used herein means to manifest the effects of a gene, to cause to produce an effect or a phenotype, or to manifest a genetic trait, depending upon the context. The expression of a gene is the translation of information encoded in the gene into protein or RNA. Expressed genes include genes that are transcribed into messenger RNA (mRNA) and then translated into protein, as well as genes that are transcribed into types of RNA, such as transfer RNA (tRNA) and ribosomal RNA (rRNA) that are not translated into protein. Several steps in the gene expression process may be modulated, including the transcription, RNA splicing, translation and post-translational modification of a protein. Gene regulation gives the cell control over structure and function, and is the basis for cellular differentiation, morphogenesis and the versatility and adaptability of an organism, such as a plant.

The term "fitness" as is used herein refers to a measure of the relative breeding success of an organism, such as a plant, or genotype, in a given population at a given time. Individuals that contribute the most offspring to the next generation are the fittest. Fitness therefore reflects how well an organism is adapted to its environment, which determines its survival.

The term "gene" as is used herein refers to the basic unit of heredity (genetic traits) in a living organism (plant, animal or micro-organism) that holds the information that is required to pass genetic traits to offspring. It is a segment of deoxyribonucleic acid (DNA) that contributes to a phenotype/function. The DNA is a molecule in the shape of a double helix, with each rung of the spiral ladder having two paired bases selected from adenine (A), thymine (T), cytosine (C) or guanine (G). Certain bases always pair together (AT and GC), and different sequences of base pairs form coded messages. Genes are arranged in precise arrays all along the length of chromosomes, which are much larger structures.

The phrase "gene expression" as is used herein means the process in which a cell produces the protein and, thus, the characteristic, that is specified by a gene's nucleotide sequence.

The phrase "genetic map" as is used herein means a diagram that shows the genetic linkage relationships among loci on chromosomes (or linkage groups) within a given species. "Mapping" is the process of defining the linkage relationships of loci through the use of genetic markers, populations that are segregating for such markers, and standard genetic principles of recombination frequency. A "map location" is a specific locus on a genetic map where an allele can be found within a given species.

The phrase "genetic marker" as is used herein means a specific fragment of DNA that can be identified within a whole genome. It is a genetic factor that can be identified and, thus, act to determine the presence of genes or traits linked with them, but not easily identified.

The term "genome" as is used herein means the complete set of genes in an organism, such as a plant, or the total genetic content in one set of chromosomes, depending upon the context. It is the complete set of chromosomes found in each cell nucleus of an individual or organism.

The term "genotype" as is used herein refers to an organism's inherited instructions that it carries within its genetic code. A genotype for a gene is generally the set of alleles that it possesses. A genotype is the specific combination of alleles present at a single locus in the genome.

The term "germination" as is used herein means the process by which a dormant seed emerges from a period of dormancy, and begins to sprout and grow into a seedling under the right growing conditions. The most common example of germination is the sprouting of a seedling from a seed of an angiosperm or gymnosperm. It is the growth of an embryonic plant contained within a seed, and results in the formation of a seedling.

The term "glucose" as is used herein means a simple monosaccharide sugar that serves as the main source of energy, and as an important metabolic substrate for most living things. Its chemical formula is $C_6H_{12}O_6$. Glucose is one of the products of photosynthesis in plants, and the glucose molecules are stored as repeating units of sugar (e.g. starch). Glucose also serves as an important metabolic intermediate of cellular respiration.

The term "glume" as is used herein means a basal, membranous, outer sterile husk or bract in the flowers of grasses, sedges and maize.

The term "harvest" as is used herein means the gathering (collecting and/or assembling) of a crop of any kind, for example, of maize.

The term "heterozygous" as is used herein means having dissimilar alleles that code for the same gene or trait. It is a situation in which the two alleles at a specific genetic locus are not the same. An example is a zygote having one dominant allele and one recessive allele, i.e., Aa, for a particular trait.

The term "heterozygosity" as is used herein means the presence of different alleles at one or more loci on homologous chromosomes.

The term "homologous" as is used herein in connection with chromosomes means those that contain identical linear sequences of genes, and which pair during meiosis. It means stretches of DNA that are very similar in sequence, so similar that they tend to stick together in hybridization experiments. Each homologue is a duplicate of one of the chromosomes contributed by one of the parents, and each pair of homologous chromosomes is normally identical in shape and size. Homologous can also be used to indicate related genes in separate organisms controlling similar phenotypes.

The phrase "homologous chromosomes" as is used herein means a pair of chromosomes containing the same linear gene sequences, each derived from one parent.

The term "homozygous" as is used herein means a situation in which two alleles at a specific genetic locus are identical to one another.

The term "homozygosity" as is used herein means the presence of identical alleles at one or more loci (a specific place on a chromosome where a gene is located.) in homologous chromosomal segments.

The term "hybrid" as is used herein means an offspring or progeny resulting from a cross between parents of two different species, sub-species, races, cultivates or breeding lines (i.e., from crossbreeding). A single cross hybrid is a first generation of offspring resulting from a cross between pure bred parents. A double cross hybrid is offspring resulting from a cross between two hybrids of single cross. A three-way cross hybrid is offspring from a cross between a single cross hybrid and an inbred line. A triple cross hybrid is offspring resulting from the crossing of two different three-way cross hybrids.

The term "hybridization" as is used herein means the process of pollen transfer from the anther of the flower of one plant to the stigma of the flower of a different plant for the purpose of gene transfer to produce an offspring ("hybrid") having a mixed parental genotype. An example of a cross of two parental lines to produce a hybrid that is discussed in U.S. Pat. No. 4,630,393, for example, is the following:

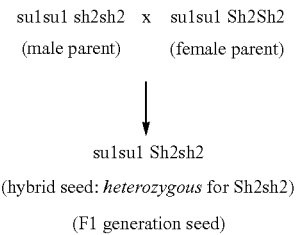

The genetic composition of the triploid (3N) endosperm of F2 corn ears produced from plants grown using the above seed is as follows, and the ears are characterized by a 3:1 segregation of normal kernels to shrunken (sh2sh2) kernels:

| Genotype | Phenotype | Ratio |
|---|---|---|
| su1su1su1 Sh2Sh2Sh2 | Sugary | 1 |
| su1su1su1 Sh2Sh2sh2 | Sugary | 1 |
| su1su1su1 Sh2sh2sh2 | Sugary | 1 |
| su1su1su1 sh2sh2sh2 | Sugary, shrunken | 1 (have a higher sugar content) |

Many other examples of crosses are present in this patent. Depending upon the context, which may readily be determined by those having ordinary skill in the art, the term "hybridization" may alternatively mean bringing complementary single strands of nucleic acid together so that they stick and form a double strand. In this manner, hybridization is used in conjunction with DNA and RNA probes to detect the presence or absence of specific complementary nucleic acid sequences.

The phrase "Independent Assortment" as is used herein refers to a separation of the alleles of one gene into the reproductive cells (gametes) independently of the way in which the alleles of other genes have segregated. By this process, all possible combinations of alleles should occur equally frequently in the gametes. In practice, this does not always happen because alleles that are situated on the same chromosome tend to be inherited together. However, if the allele pairs Aa and Bb are on different chromosomes, the combinations AB, Ab, aB, and ab will normally be equally likely to occur in the gametes.

The term "inbred" as is used herein means offspring produced by inbreeding (succeeding generations of organisms, such as plants, that are all derived by breeding from the same group of closely related organisms). When lines are inbred sufficiently, a homozygous condition of particular alleles can generally be assumed.

The term "inbreeding" as is used herein means the breeding of plants, plant materials or organisms that are related, depending upon the context (i.e., of plants, plant materials or organisms within an isolated or a closed group of plants, plant parts or organisms). It is the continued breeding of closely related plants, plant parts or organisms, so as to preserve desirable traits in a therein.

The term "intron" as is used herein refers to portions of genomic DNA that are not coding sequences. While they are transcribed (and thus present in the primary transcript), they are later spliced out. They, thus, are not present in the corresponding mature mRNA.

The term "isogenic" as is used herein means having the same genotype (i.e., genetically uniform), as all organisms produced by an inbred strain.

The terms "library," "DNA library" and "gene library" as are used herein refer to a plurality or collection of DNA fragments of one or more organisms, each generally carried by a plasmid or virus and cloned into an appropriate host. A DNA probe is generally used to locate a specific DNA sequence in the library. A collection representing the entire genome of an organism is known as a genomic library, and an assortment of DNA copies of messenger RNA produced by a cell is known as a complimentary DNA (cDNA) library.

A "linkage map" as is used herein means a map of the relative positions of genetic loci on a chromosome, determined on the basis of how often the loci are inherited together. Distance may be measured in centimorgans (cM).

The term "locus" as is used herein refers to a specific chromosome location in the genome of a species where a specific type of gene can be found. It is the position on the chromosome where the gene for a particular trait resides. A locus may be occupied by any one of several alleles (variants) for a given gene.

The phrase "Mendel's Laws" as is used herein refers to the two laws that summarize Gregor Mendel's theory of inheritance, which are the foundation of genetics. The Law of Segregation states that each hereditary characteristic is controlled by two 'factors' (alleles), which segregate (separate) and pass into separate germ (reproductive) cells. The Law of Independent Assortment states that pairs of 'factors' (alleles) segregate independently of each other when germ cells are formed.

The phrase "molecular marker" as is used herein means a specific fragment of DNA that can be identified within a whole genome. It is an identifiable physical location on a chromosome (i.e., restriction enzyme cutting site, gene, or the like) whose inheritance can be monitored. Molecular markers are generally found at specific locations of a genome, and are used to 'flag' the position of a particular gene or the inheritance of a particular characteristic. In a genetic cross, the genes producing characteristics of interest will usually stay linked with the molecular markers in relatively close proximity on the chromosome. Thus, varieties can be selected in which the molecular marker is present, since the marker indicates the presence of the desired characteristic. Examples of molecular markers include simple sequence repeats (SSRs), single nucleotide polymorphisms (SNPs), randomly amplified polymorphic DNA (RAPDs), and restriction fragment length polymorphisms (RFLPs). Additional information about the use of molecular markers for use in characterizing and identifying maize inbred lines, validating pedigree and showing associations among inbred lines is present in J. S. Smith et al., "An Evaluation of the Utility of SSR loci as Molecular Markers in Maize (Zea Mays L.): Comparisons with Data from RFLPS and Pedigree," Theor Appl Genet 95:163-173 (1997). Microsatellites, or simple sequence repeats (SSRs) are relatively short nucleotide sequences, usually from 2 to 3 bases in length that are generally repeated in tandem arrays. Amplifiable polymorphisms are revealed because of differences in the number of tandem repeats that lie between sequences that are otherwise conserved for each locus. Microsatellite loci are highly polymorphic and are useful as genetic markers in many plant species, including maize.

The terms "multiple," "number" and "plurality" as are used herein mean more than one, for example, two, three, four, five, six, seven, eight, nine, ten, eleven, twelve, thirteen, fourteen, fifteen, sixteen, seventeen, eighteen, nineteen, twenty, twenty five, thirty, thirty-five, forty, forty-five, fifty, fifty-five, sixty and so forth. The term "number" may also include one.

The term "mutation" as is used herein refers to a permanent, heritable change of genetic material, either in a single gene or in the numbers or structures of the chromosomes. A mutation occurs when a gene is changed in such a way as to alter the genetic message carried by that gene. Once the gene has been changed, the mRNA transcribed from that gene will now carry an altered message, and the polypeptide made by translating the altered mRNA will now contain a different sequence of amino acids. The function of the protein made by folding this polypeptide may also be changed or lost. In subtle or very obvious ways, the phenotype of the organism carrying the mutation may be changed. Mutation may be small scale (affecting the nucleotide sequence of a gene) or large scale (involving a change in the chromosome). It may arise from deletions (the deletion of one or more nucleotides in the genetic material), insertions (an insertion of one or more extra nucleotides into a new place in the genetic material) or substitutions (an exchange of one or more nucleotides for another in the genetic material, for example, switching an A to a G), as may be caused by exposure to ultraviolet or ionizing radiation, chemical mutagens, viruses or the like. For example, a substitution may: (i) change a codon to one that encodes a different amino acid, and cause a small change in the protein produced; (ii) change a codon to one that encodes the same amino acid, and causes no change in the protein produced; or (iii) change an amino-acid-coding codon to a single "stop" codon and cause an incomplete protein. Mutations may result in the creation of a new character or trait. Mutations may increase an organism's fitness, which may spread through the population over successive generations by natural selection. Mutation is the ultimate source of genetic variation, and a particular mutant gene or allele may be compared to its corresponding wild type gene or allele to determine the differences between the two genes or alleles. There are different types of mutations. For example, a point mutation is a single nucleotide substitution within a gene, and there may be several point mutations within a single gene. Point mutations generally do not lead to a shift in reading frames and, thus, at most generally cause only a single amino acid substitution. Because protein-coding DNA is divided into codons that are three bases long, insertions and deletions can alter a gene so that its message is no longer correctly parsed. These changes are known as "frameshifts." In frameshifts, a similar error occurs at the DNA level, causing the codons to be parsed incorrectly. This usually generates truncated proteins that useless. Additional information regarding mutations is present in *Mutation: Science of Everyday Things* (Gale Group, 2002).

The term "NILs" as is used herein means near isogenic lines, which are lines of a plant, such as sweet corn, that are genetically identical, except for one locus or a few loci.

The phrase "organoleptic testing" as is used herein means a testing of the physical and/or chemical changes that are inherent to decomposition. It may be performed on food, such as sweet corn, to measure and evaluate the temperature, taste, smell, texture and/or other properties that are capable of eliciting a response in the sensory organs of human beings or animals. Organoleptic refers to the sensory properties of a substance, such as taste, color, odor and/or feel, and organoleptic testing involves inspection through tasting, feeling, smelling and/or visual examination of a substance.

The term "phenotype" as is used herein means an observable characteristic or trait of an organism, such as sweet corn, such as its morphology, development and/or biochemical or physiological properties. It is a biological trait or characteristic possessed by an organism (including a plant) that results from the expression of a specific gene. Phenotypes generally result from the expression of an organism's genes, as well as the influence of environmental factors, and possible interactions between the two. In natural populations, most phenotypic variation is continuous, and is effected by alleles at one or multiple gene loci.

The term "plant" as is used herein means any organism that that belongs to Kingdom Plantae, and that is often characterized by one or more (or all) of the following features:

- an ability to make its own food by photosynthesis (i.e. capable of capturing energy via the green pigment (chlorophyll) inside of the chloroplast, and of using carbon dioxide and water to produce sugars as food and oxygen sugars as food, and oxygen as byproduct;
- foods are stored in forms of sugars and starch;
- a presence of rigid cell walls apart from the cell membrane;
- has eukaryotic cells (i.e. the presence of a distinct nucleus surrounded by a membrane);
- mostly are multicellular (i.e. made up of many cells that are organized to perform a specific function as a unit);
- unlimited growth at meristems (when present);
- organs are specialized for anchorage, support and photosynthesis (e.g. roots, stems, leaves, etc.);
- response to stimuli is rather slow due to the absence of sensory organs and nervous systems;
- limited movements due to a lack of organs for mobility; and/or
- has a life cycle that involves both sporophytic and gametophytic phases.

Plants are the major producers in an ecosystem, and they include, for example, trees, herbs, bushes, grasses, vines, ferns and mosses. Examples of particular plants include, but are not limited to, lettuce, tobacco, cotton, corn, rice, wheat, carrot, cucumber, leek, pea, melon, potato, tomato, sorghum, rye, oat, sugarcane, peanut, flax, bean, sugar beets, soya and sunflower plants.

The term "plasmid" as is used herein means any of several generally pigmented cytoplasmic organelles that are found in plant cells, having various physiological functions, such as the synthesis and storage of food.

The term "pleotropic" as is used herein means producing multiple effects from a single gene. For example, in humans, the Marfan gene is pleotropic and can cause long fingers and toes, dislocation of the lens of the eye and dissecting aneurysm of the aorta.

The term "pollen" as is used herein means the fine powder-like material consisting of pollen grains that contain the male reproductive cells of most plants. Pollen is generally produced by the anthers of seed plants.

The term "pollination" as is used herein means the process by which plant pollen is transferred, generally from the anther to the stigma (from male reproductive organs to the female reproductive organs) of a plant flower to produce offspring (to form seeds). In flowering plants, pollen is transferred from the anther to the stigma, often by the wind or by insects. In cone-bearing plants, male cones release pollen that is usually borne by the wind to the ovules of female cones. The pollen grain generally contains two cells: a generative cell and a tube cell. The generative nucleus generally divides to form two sperm nuclei. The tube cell generally grows down into the pistil until it reaches one of the ovules contained in the ovary. The two sperm generally travel down the tube and enter the ovule, where one sperm nucleus generally unites with the egg. The other sperm nucleus generally combines with the polar nuclei that exist in the ovule, completing a process known as "double fertilization." These fertilized nuclei then generally develop into the endocarp, the tissue that feeds the embryo. The ovule itself generally develops into a seed that is contained in the flower's ovary (which ripens into a fruit). In gymnosperms, the ovule is exposed (not contained in an ovary), and the pollen produced by the male reproductive structures lands directly on the ovule in the female reproductive structures.

The phrases "polymerase chain reaction" and "PCR" as are used herein refer to a technique that is well known by those having ordinary skill in the art for replicating a specific piece of DNA in vitro, even in the presence of excess non-specific DNA. Primers are added (which initiate the copying of each strand) along with nucleotides and heat stable Taq polymerase. By cycling the temperature, the target DNA is repetitively denatured and copied. Because the newly synthesized DNA strands can subsequently serve as additional templates for the same primer sequences, successive rounds of primer annealing, strand elongation, and dissociation produce rapid and highly specific amplification of the desired sequence. PCR also can be used to detect the existence of the defined sequence in a DNA sample. A single copy of the target DNA, even if mixed in with other undesirable DNA, can be amplified to obtain billions of replicates. PCR can be used to amplify RNA sequences if they are first converted to DNA via reverse transcriptase. PCR buffers, primers, probes, controls, markers, amplification kits, sDNA synthesis kits, general PCR kits, and the like are available from sources that are known by those having ordinary skill in the art, such as Applied Biosystems (Foster City, Calif.), and may readily be used by those having ordinary skill in the art in accordance with the present invention.

The term "primer" as is used herein means a relatively short pre-existing polynucleotide chain to which new deoxyribonucleotides can be added by DNA polymerase.

The phrases "prime eating stage" and "peak eating stage" as are used herein mean the stage when a plant, such as sweet corn, tastes the most favorable or sweetest, which may readily be determined by those having ordinary skill in the art and, for sweet corn, may be when the corn kernels contain approximately 75% moisture. For example, sweet corn tends to mature all at once, and when it is past its prime eating stage, the sweetness generally becomes diminished or absent, and is replaced by a bland, starchy flavor, which is not desirable to consumers.

The term "nucleotide" as is used herein means the basic building block (subunits) of nucleic acids, such as DNA and RNA. It is an organic compound that is generally made up of nitrogenous base, a sugar and a phosphate group. DNA molecule consists of nucleotides in which the sugar component is deoxyribose, whereas the RNA molecule has nucleotides in which the sugar is ribose. The most common nucleotides are divided into purines and pyrimidines based upon the structure of the nitrogenous base. In DNA, the purine bases include adenine and guanine, while the pyrimidine bases are thymine and cytosine. RNA includes adenine, guanine, cytosine and uracil instead of thymine. Aside from serving as precursors of nucleic acids, nucleotides also serve as important cofactors in cellular signaling and metabolism. These cofactors include flavin adenine dinucleotide (FAD), flavin mononucleotide, adenosine triphosphate (ATP) and nicotinamide adenine dinucleotide phosphate (NADP). To form a DNA or RNA molecule, generally thousands of nucleotides are joined together in a long chain. A DNA oligonucleotide is a short piece of DNA composed of relatively few (oligo-) nucleotide bases.

The term "pericarp" as is used herein means the wall of a plant fruit, such as a corn kernel, which generally is developed from an ovary wall, and contains an outer exocarp, a central mesocarp and an inner endocarp.

The term "phytoglycogen" as is used herein means a plant polysaccharide having a structure that is similar to glycogen, and similar properties. For example, the phytoglycogen present in sweet corn is a water soluble glycan having an average unit chain length of 13, reflecting a generally high degree of branching.

The term "polynucleotide" as is used herein means an organic polymer molecule that is composed of nucleotide monomers covalently bonded in a chain. DNA (deoxyribonucleic acid) and RNA (ribonucleic acid) are examples of polynucleotides that have a distinct biological function.

The term "polysaccharide" as is used herein means any of a class of carbohydrates, such as starch and cellulose, consisting of a number of monosaccharides that are joined by glycosidic bonds.

The term "protein" as is used herein refers to a large molecule composed of one or more chains of amino acids in a specific order, which is determined by the base sequence of nucleotides in the gene that is coding for the protein. Proteins are required, for the structure, function, and regulation of cells, and each protein has unique functions.

The term "recessive" as is used herein in connection with a gene means a gene whose phenotypic effect is expressed in the homozygous state, but is masked in the presence of the dominant allele (i.e. when the organism is heterozygous for that gene). It is a phenotype that is expressed in organisms (including plants) only if it is homozygous for the corresponding allele. Usually the dominant gene produces a functional product whereas the recessive allele does not: both 1 dose and 2 doses per nucleus of the dominant allele, therefore, generally lead to an expression of its phenotype, whereas the recessive allele is generally observed only in the complete absence of the dominant allele.

The letter "R" as used herein in connection with a designation of a sweet corn hybrid indicates that such hybrid is resistant to common leaf rust (i.e., that it is rust resistant). Common rust, caused by *Puccinia sorghi*, is known to be a major pathogen to, and can significantly reduce the yields of, *Zea mays*, sweet corn. Epidemics of this disease can cause serious losses in yield and quality of sweet corn. High rust susceptibility of many popular sweet corn hybrids is a major factor contributing to rust epidemics. Another factor is that sweet corn is usually planted over an extended period from May through June for fresh and processing uses. The staggered planting schedules result in high concentrations of fungal spores in the air, originating from early planted fields, at the time when late-planted fields contain young actively growing susceptible plants. Common rust on sweet corn appears in the field as oval to elongate cinnamon brown pustules scattered over upper and lower surfaces of the leaves. The pustules rupture and expose dusty red spores (urediniospores), which are spread by wind and have the ability to infect other corn leaves directly. As the pustules mature, they turn brownish black and release the dark-brown overwintering spores (teliospores). In severe epidemics, pustules may also appear on the ears and tassels, and the leaves may yellow and become easily tattered in strong winds. Partial resistance is expressed as chlorotic or necrotic hypersensitive flecks with little or no sporulation. Rust epidemics on sweet corn have been severe in the past. Three major factors interact to influence the outbreak of rust epidemics on sweet corn: (1) the quantity of urediniospores available to initiate rust epidemics; (2) environmental factors; and (3) the level of rust susceptibility in the sweet corn varieties in use. Urediniospores are unable to overwinter successfully in northern climates. Each spring urediniospores move north from the southwestern United States and Mexico, following the sequential plantings of corn from the south up to Canada. Temperatures of 60° to 75° F. (16-24° C.) and heavy dews or high relative humidity (close to 100%) favor rust development. The current weather conditions influence spore germination and the rate at which rust epidemics develop. Moisture is required for spore germination. Infection will generally occur when leaves are wet for a minimum of about 3 to about 6 hours. Although most of the current popular sweet corn hybrids are susceptible to rust, resistant varieties are becoming available. Two types of resistance are being used by commercial sweet corn breeders: race-specific resistance and partial rust resistance. Modest control of rust on sweet corn can be achieved with applications of fungicides. Trials conducted in western New York have shown that three applications of mancozeb applied by air significantly reduced disease severity on all the leaves of sweet corn plants. Fungicide applications also significantly increased the number of harvestable ears and the weight of the harvested ears. Research conducted in other states has shown that, by controlling rust with fungicides, improvements in moisture content sugar content, and ear-tip fill were observed. However, timing of the first fungicide application is critical because it needs to be applied early enough to reduce the rate of epidemic development. Because rust spores generally arrive from outside the immediate area planted to corn, it is often difficult to predict when this spray should be applied.

The letter "SS" as is used herein in connection with a designation of a sweet corn hybrid indicates that such hybrid includes the mutant sh2-i gene.

The term "seed" as is used herein means a propagating organ formed in the sexual reproductive cycle of gymnosperms and angiosperms (male and female sex cells) that includes a protective coat enclosing an embryo and food reserves. It is a small hard fruit that is generally located in a fertilized ovule of a plant. A seed has two main components, the embryo and the endosperm. The endosperm acts as a food store for the embryo which, over time, will grow from this rich food supply that enables it to do so. Most seeds go through a period of quiescence in which there is no active growth. During this time, the seed can be safely transported to a new location and/or survive adverse climate conditions until it is favorable for growth. The seed contains an embryo and, in most plants, stored food reserves wrapped in a seed coat. Under favorable growth conditions, a seed begins to germinate, and the embryonic tissues resume growth, developing towards a seedling. Additional information about seeds, seedlings, germination and plant growth is present in P. Raven et al., Biology of Plants (7th Edition, New York: W.H. Freeman and Company), 504-508 (2005); and B. Larkins et al., Cellular and Molecular Biology of Plant Seed Development (Kluwer Academic Publishers, 1997).

The term "seedling" as is used herein means a young plant sporophyte developing out of a plant embryo from a seed. Seedling development starts with the germination of the seed. A typical young seedling consists of three main parts: (i) the radicle (embryonic root); (ii) the hypocotyl (embryonic shoot); and (iii) the cotyledons (seed leaves). During germination, the young plant emerges from its protective seed coat generally with its radicle first, followed by the cotyledons. The radicle orients towards gravity, while the hypocotyl orients away from gravity and elongates through cell expansion to push the cotyledons out of the ground. Typically, seedling development starts with skotomorphogenesis while the seedling is growing through the soil and attempting to reach the light as fast as possible. Generally during this phase, the cotyledons are tightly closed and form an apical hook to protect the shoot apical meristem from damage while pushing through the soil. In many plants, the seed coat still covers the cotyledons for extra protection. Upon breaking the surface and reaching the light, the seedling's developmental program is generally switched to photomorphogenesis. The cotyledons generally open upon contact with light (splitting the seed coat open, if still present) and become green, forming the first photosynthetic organs of the young plant. Until this stage, the seedling generally lives off of the energy reserves that are stored in the seed. The opening of the cotyledons generally exposes the shoot apical meristem and the plumule, consisting of the first true leaves of the young plant. Seedlings senselight through the light receptors phytochrome (red and far-red light) and cryptochrome (blue light). Once a seedling starts to photosynthesize, it generally is no longer dependent on the seed's energy reserves. Generally, the apical meristems start growing and give rise to the root (the organ of the plant that typically lies below the surface of the soil) and shoot (new plant growth, such as stems and leaves). The first "true" leaves generally expand, and can often be distinguished from the round cotyledons through their species-dependent distinct shapes. While the plant is growing and developing additional leaves, the cotyledons eventually senesce and fall off.

The phrase "segregation analysis" as is used herein means a method for confirming allelism. This may be performed by crossing two lines that are homozygous but contain different alleles at a locus in question. One may then monitor segregation of the alleles in segregating generations to test for expected Mendelian segregation patterns. Homology of DNA fragments to the same probe and mutual exclusivity among diverse inbred lines is generally a reasonable test of allelism.

The term "selfing" as is used herein means manually pollinating a plant by placing its pollen on its own stigma (self pollination), and it is a breeding strategy that can lead to homozygosity of an allele. If a set of parents are homozygous for the same allele, this allele is simply transmitted and the progeny will generally be homozygous for this same allele. On the other hand, if the parents are homozygous, but for different alleles, A and B, then the progeny is a heterozygote A/B if a single cross is made, but is homozygous A or B, each with an expectation of ½ if the cross is followed by many selfings.

The phrases "sh2-i mutant allele," "sh2-i allele," "sh2-i mutant gene" and "sh2-i gene" as are used herein mean mutant alleles or genes that contain the same intron splice site point mutation that is described and shown herein, and confer the same trait(s) as are described herein, whether designated as sh2-i or by some other designation, such as by sh2-N2340.

The term "soil" as is used herein means any kind of a medium, or mixture of mediums, in which a plant seed, such as a maize seed, will typically reasonably grow into a plant, such as the unconsolidated mineral or organic material that is present on the surface of the Earth, which serves as a natural medium for the growth of land plants. Such mediums are known by those having ordinary skill in the art.

The term "starch" as is used herein means a polysaccharide carbohydrate that generally includes a large number of glucose monosaccharide units that are joined together by glycosidic bonds, and is found in plant seeds, bulbs and tubers. Starch is generally predominantly present as amylase and amylopectin. Plants use starch as a way to store excess glucose, and as food during mitochondrial oxidative phosphorylation.

The term "sucrose" as is used herein means a disaccharide made up of glucose and fructose that is present in many plants, and is widely used as a sweetener or preservative.

The term "sugar" as is used herein means any disaccharides (e.g. sucrose) and monosaccharides (e.g. fructose or glucose). Sugars are essential structural component of living cells, and are a source of energy for many organisms, such as plants. Plants use sugars to store energy. Sugars are classified based on the number of monosaccharide units that are present in the molecule. The monosaccharides join to form more complex sugars, e.g. disaccharides.

The phrase "test cross" as is used herein means the crossing of an organism, such as a plant, with an unknown genotype, to a homozygous recessive organism (tester). It is a cross between an individual of unknown genotype or a heterozygote (or a multiple heterozygote) to a homozygous recessive individual.

The term "trait" as is used herein refers to a distinguishing quality or characteristic, and is generally a distinct variant of a phenotypic character of an organism, such as sweet corn, that may be inherited and/or environmentally determined, for example, the sugar content of sweet corn. The goal of plant breeding in general is to produce progeny that exceed their parents in terms of performance for one or more traits. Such progeny (transgressive segregants) may be identified using techniques that are known by those having ordinary skill in the art, such as segregation analyses. In order to observe transgressive segregation, parents that complement one another in terms of favorable alleles at various loci must generally be selected. Crossing and recombination can then result in progeny that contain more favorable alleles than either parent.

The term "transcription" as is used herein means the synthesis of RNA under the direction of DNA. RNA synthesis, or transcription, is the process of transcribing DNA nucleotide sequence information into RNA sequence information. Both nucleic acid sequences use complementary language, and the information is simply transcribed, or copied, from one molecule to the other. DNA sequence is enzymatically copied by RNA polymerase to produce a complementary nucleotide RNA strand (messenger RNA or mRNA) because it carries a genetic message from the DNA to the protein-synthesizing machinery of the cell. One significant difference between RNA and DNA sequence is the presence of U, or uracil in RNA instead of the T, or thymidine of DNA. In the case of protein-encoding DNA, transcription is the first step that usually leads to the expression of the genes, by the production of the mRNA intermediate, which is a faithful transcript of the gene's protein-building instruction. The stretch of DNA that is transcribed into an RNA molecule is the transcription unit.

A DNA transcription unit that is translated into protein contains sequences that direct and regulate protein synthesis in addition to coding the sequence that is translated into protein. The regulatory sequence that is before (upstream (−), towards the 5' DNA end) the coding sequence is the 5' untranslated region, and regulatory sequence that is found following (downstream (+), towards the 3' DNA end) the coding sequence is the 3' untranslated region. As in DNA replication, the RNA is synthesized in the 5'→3' direction. Only one of the two DNA strands is transcribed. This strand is the template strand because it provides the template for ordering the sequence of nucleotides in an RNA transcript. The other strand is the coding strand because its sequence is the same as the newly created RNA transcript (except for uracil being substituted for thyamine). The DNA template strand is read 3'→5' by RNA polymerase and the new RNA strand is synthesized in the 5'→3' direction. A polymerase binds to the 3' end of a gene (promoter) on the DNA template strand and travels toward the 5' end. Transcription is divided into 5 stages: pre-initiation, initiation, promoter clearance, elongation and termination. Additional information about transcription is present in J. Berg J et al., Biochemistry (6th ed., San Francisco: W.H. Freeman, 2006); and R. J. Brooker, Genetics: Analysis and Principles (2nd ed., New York: McGraw-Hill, 2005).

The term "translation" as is used herein means the process by which polypeptide chains are synthesized, the sequence of amino acids being determined by the sequence of bases in a messenger RNA, which in turn is determined by the sequence of bases in the DNA of the gene from which it was transcribed. Additional information regarding translation is present in D. V. Lim, Microbiology (3rd ed., Kendal/Hunt, 2003).

The term "vigor" as is used herein means an exertion of force or a measure of the increase in plant growth and/or foliage volume through time after planting (i.e., after the proper setting of seeds into the ground for propagation), and/or of some other superior quality related to seed, seedling and/or plant strength and/or growth, such as an enhanced germination and/or seedling emergence out of the ground, depending upon the context. A plant line can be called "vigorous" when the line grows vitally, healthy, is tolerant to various biotic and abiotic stresses and/or has a high yield, possibly even while under sub-optimal conditions. Vigor can be measured, and compared for different plant varieties (or for particular lines within a particular plant variety), by methods that are known by those having ordinary skill in the art, in terms of percents (from 0% to 100%), or otherwise, and the higher the growth and yield of a particular plant variety (or line) (in seeds, fruits, vegetables, plants and/or the like), the more vigor the plant generally has. For example, one sweet corn variety or line may produce approximately 10% fewer kernels when compared with another sweet corn variety or line. One method for determining plant hybrid "yield vigor" (and other vigor) is described in U.S. Pat. No. 7,084,320 B2. Other methods for determining vigor are known by those having ordinary skill in the art.

The term "yield" as is used herein refers to plant, plant material and/or seed productivity, such as the productivity per unit area of a particular plant product of commercial significance. For example, yield of soybean is commonly measured in bushels of seed per acre, or metric tons of seed per hectare, per season.

The term "wildtype" as is used herein refers to a native or predominant genetic constitution before mutations, usually referring to the genetic constitution normally existing in nature.

The letter "Y" as is used herein in connection with a designation of a sweet corn hybrid indicates that such hybrid is yellow in color.

Abbreviations

The table below lists many of the abbreviations that are employed herein along with their meanings.

su1 (sugary-1) allele: a recessive allele on chromosome 4 (a mutant), which produce a moderate increase in overall sugar levels, and resulting sweet taste, to corn, with the sweetness deteriorating rapidly (thus, a short shelf life), and which gives corn kernels a smooth and creamy texture and appearance (desirable);

Su1 (starchy-1) allele: a dominant allele on chromosome 4, which is found in field (dent) corn (not a mutant);

se1 (sugary enhancer-1) allele: a recessive allele on chromosome 2 (a mutant), which increases total sugar, and provides an enhanced sweetness, to conventional su1 variety corn kernels when the genotype is homozygous se1se1);

Se1 allele: a dominant allele on chromosome 2 (not a mutant) that precludes an expression of elevated sweetness and tenderness;

sh2 (shrunken-2) allele: a recessive allele on chromosome 3 (a mutant) which produces about twice the sugar content of su1 corn varieties, and an associated much sweeter taste, when the genotype is homozygous sh2sh2, which has lightweight, easily-damaged seeds having a "shrunken" appearance due to a reduction in endosperm weight and starch levels, and an associated significantly reduced seedling vigor, fitness and/or health during germination, seedling emergence from soil, and plant development and growth in comparison with conventional su1 and se1 sweet corn varieties, and which has a sugar retention at the post prime eating stage that is significantly extended relative to conventional su1 and se1 mutant sweet corns;

Sh2 allele: a dominant allele present in normal sweet corn plants (i.e., not including the sh2 mutant allele) (not a mutant) (See U.S. Pat. No. 4,630,393, col. 3);

sh2-i allele: a recessive form of the sh2 gene (a mutant) that produces enhanced germination and growth characteristics to corn plants in comparison with corn plants expressing the sh2 gene.

Plant Reproduction: Female and Male Plants

The three structures that generally comprise the reproductive system of a female plant, which is known as the pistil, are the stigma, style and ovary. The stigma is typically that part of the female reproductive structure upon which pollen adheres and germinates, and is generally terminal in location. The style is the stalk-like part of the female reproductive structure, and connects the stigma with the ovary, which generally includes one or more ovules.

The two structures that generally comprise the reproductive system of a male plant, which is known as the stamen, are the anther and the filament. The anther is the pollen containing part of the male reproductive system, and typically includes one or more sacs. Pollen becomes formed and matures within this part of the male plant. The filament is a stalk-like portion of this reproductive system, and typically includes the anther at its tip.

During pollination and fertilization, pollen from the male reproductive structure lands on top of the stigma of the female reproductive structure and, if conditions are conducive, the pollen will germinate. Upon germination, the pollen forms a pollen tube and grows downward through the style of the female plant and, when it reaches the female ovary, releases the male nuclei into the ovum, with fertilization occurring.

The pericarp of corn (a monocot seed) is the fruit wall or seed coat, which is developed from the ovary wall. The endosperm is located interior to the pericarp, and functions to provide a source of reserve material and energy for the germination process, during which it will be broken down and used by the developing embryo for growth. The soft endosperm is the soft nutritive tissue formed within the embryo sack of seed plants, and the hard endosperm is the same nutritive tissue formed in the embryo sack, but is of a hard consistency. The embryo is the rudimentary plant located within a seed that will develop into a seedling, and then subsequently into a plant.

Additional information regarding female and male plants, and their reproduction, is described in T. A. Kiesseelbach, *The Structure and Reproduction of Corn* (Cold Spring Harbor Laboratory Press, 1999); and J. E. Bradshaw, *Root and Tuber Crops* (*Handbook of Plant Breeding*).

Information about plant genetics and various plant breeding techniques is described, for example, in Jack Brown et al., *An Introduction to Plant Breeding* (Blackwall Publishing LTD, 2008, ISBN 978-1-4051-3344-9); and George Acquaah, *Principles of Plant Genetics and Breeding* (Blackwall Publishing LTD, 2007, ISBN 13-978-1-4051-3646-4), which includes an extensive glossary of plant genetics and plant breeding terms. Details regarding sweet corn cultivation are provided in the web site sweetcorngrowingtips dot com.

General Description and Utility

The present invention provides unique, cost-effective, reliable, efficient and successful methods for developing and producing plants, plant materials and seeds, such as corn kernels, and corn, that receive, and have, multiple very desirable attributes for consumers of these products, as well as for commercial plant growers, and to improved and/or enhanced plants, plant materials and seeds that are produced in accordance with these methods. These inventive methods very advantageously provide inbred, hybrid and other plants, plant materials and seeds that have multiple very beneficial and desirable characteristics or traits, generally including those that are described below (as well as others), even when subjected to reasonable amounts of environmental or other stresses, such as cooler temperatures, drought conditions, low nutrients and other poor soil conditions, crowding, disease, insects, animals, pollution and/or the like. While these beneficial traits are described below in connection with corn plants, such traits may also be produced in connection with other types of plants.

The corn kernels physically are fuller, and have a higher carbohydrate and water soluble polysaccharides (WSP) content, at the dry seed stage in comparison with conventional shrunken-2 (sh2) and shrunken-2i (sh2-i) mutant gene corn varieties (and other corn varieties, such as wildtype corn varieties), which have greatly reduced carbohydrate and, thus initial and subsequent energy levels, and/or water soluble polysaccharides levels. This very advantageously results in a significantly enhanced initial and subsequent energy level and growth characteristics for the plants, such as a stronger (and maximized) vigor and fitness to the corn during seed germination, seedling emergence from soil, and plant development in comparison with the shrunken-2 (sh2) and shrunken-2i (sh2-i) mutant gene corn varieties (and other corn varieties). The plants get off to a stronger and more uniform emergence because of their higher starch reserves, which correlates with sturdier plants, a larger harvest and more plant yield, all of which is very desirable to plant growers and home gardeners.

Surprisingly, the corn kernels compare favorably in eating quality with conventional sugary-1 (su1), sugary enhancer-1 (se1) and shrunken-2 (sh2) sweet corn varieties, and even with sweet corn varieties including all three of these mutant alleles, and in some cases are better in eating quality than such sweet corn varieties (and other sweet corn varieties, such as wildtype corn varieties). The corn kernels contain elevated total sugar levels (2 to 3 times the sugar levels of many conventional corn varieties), resulting in a very desirable sweet flavor and taste of these kernels, in comparison with conventional sugary-1 (su1) mutant gene corn varieties, and other corn varieties, which is very desirable to consumers when eating the corn kernels. (Corn kernel sugar levels can be quantified using methods that are known by those having ordinary skill in the art, such as gas chromatography.) The sugar retention, and associated sweet taste, of the corn kernels at the post prime eating stage (particularly in days 1-14 immediately following the prime eating stage) is significantly extended in comparison with conventional sugary-1 (su1) and shrunken-2i (sh2-i) mutant gene corn varieties (and other corn varieties), which have a rapid conversion of sugar to starch during this period of time (resulting in a loss of sugar), and an associated reduction in sweet taste of the corn kernels, and a narrow harvest window before sweetness deteriorates very soon after the prime eating stage. This sugar retention very advantageously results in a longer sweet taste of the corn kernels, which is very desirable to consumers, a longer harvest window of the corn, a longer holding ability of the corn, and a longer shelf life of the corn before sweetness deteriorates after the prime eating stage, which very advantageously provides a much greater flexibility of harvest, and handling conditions, of the corn for corn growers. The corn kernels have a reduced starch accumulation at, and to a practical point following, the prime eating stage (peak eating quality), such as from about 1-14 days immediately following the prime eating stage, in comparison with conventional sugary-1 (su1) and shrunken-2i (sh2-i) mutant gene corn varieties (and other corn varieties).

The corn kernels of hybrid maize varieties that are produced in accordance with the methods of the invention are smooth and attractive, sweet, tender, plump and creamy, and have a high eating quality, all of which is very desirable to consumers worldwide.

Corn breeders, corn producers, corn growers, scientists and others have not been able to produce a sweet corn that includes each of the above, and very desirable, production and consumer traits (i.e., these combined traits). Further, the present inventor spent more than four years conducting experiments to attempt to successfully develop and produce hybrid varieties of sweet corn that include these very desirable combined traits, and that include the shrunken-2i (sh2-i) mutant allele along with one or more other mutant alleles, and were finally surprisingly and unexpectedly able to accomplish this goal.

The methods of the present invention combine specific mutant alleles that are present in sweet corn, or other plants, with the shrunken-2i (sh2-i) gene. The mutant alleles, which include, but are not limited to, the sugary-1 (su1), sugary enhancer-1 (se1), and shrunken-2 (sh2) mutant endosperm alleles, when expressed in a sweet corn (or other plant) hybrid in combination with the shrunken-2i (sh2-i) gene, provide enhanced growth characteristics, such as an enhanced seedling germination and seedling vigor, to the sweet corn (or other plants), as well as the other very beneficial characteristics that are described hereinabove. The methods of the present invention preferably provide a unique, sequential layering of the mutant alleles su1su1, Su1Su1 and/or se1 se1, in combination with the sh2-i mutant endosperm allele, that preserves an enhanced seedling germination and vigor along with product holding ability and shelf life.

The methods of the invention involve the use, and identification of, commercial (and other) hybrid, inbred and other plant lines containing the above mutant alleles, either singly or in combination, and exceed conventional expectations relative to seedling and plant growth characteristics. These mutant alleles confer elevated sweetness, and reduced kernel pericarp, differentially in specific combination.

The problem to be solved by the present invention, and its goal, was to manipulate the regulation of carbohydrate accumulation and pericarp tenderness in sweet corns containing the shrunken-2i (sh2-i) gene. The examples that are set forth herein describe experiments that were performed in order to solve this problem and achieve this goal.

Plant seeds, plant materials and plants that may be produced in accordance with the methods of the present invention include those that are capable of having the shrunken-2i (sh2-i) mutant allele, and at least one other beneficial mutant allele, including, but not limited to, the mutant sugary-1 (su1), sugary extender-1 (se1) and/or shrunken-2 (sh2) mutant endosperm alleles, incorporated into their genome, and expressed, in a manner that produces the beneficial combined grower and consumer traits that are described herein, which may be determined by those having ordinary skill in the art.

In a preferred embodiment, the invention involves a unique sequential combination or layering of the shrunken-2i mutant (sh2-i) allele with the mutant sugary (su1), sugary enhancer-1 (se1) and/or shrunken-2 (sh2) alleles in sweet corn. The unique sequential layering of su1su1, Su1Su1 and/or se1se1 in combination with the mutant sh2-i allele functions to preserve enhanced seedling germination and vigor along with product holding ability and shelf life, and provide sweet corn (and other plants) with the other beneficial traits that are described herein.

Nucleotide Sequences of Mutant Genes

The nucleotide sequences of some of the mutant genes that may be employed in the methods of the present invention are set forth herein. The nucleotide sequences of other mutant genes that may be employed in the invention, and related or other nucleotide sequences, may be readily obtained from sources that are known by those having ordinary skill in the art, such as from the Maize Genetics and Genomics and/or GenBank databases.

The Maize Genetics and Genomics database is a community database for biological information about the crop plant *Zea mays*, and is funded by the USDA Agricultural Research Service. The following data types are accessible through this site: genetic, genomic, sequence, gene product, functional characterization, literature reference, and person/organization contact information.

The GenBank sequence database is an open access, annotated collection of all publicly available nucleotide sequences and their protein translations. This database is produced at the National Centers for Biotechnology Information, which is a branch of the National Institutes of Health (Bethesda, Md.), and is available on line via the Entrez search engine. GenBank and its collaborators receive sequences produced in laboratories throughout the world from more than 100,000 distinct organisms, and it continues to grow at an exponential rate, doubling every 18 months. It contains over 65 billion nucleotide bases in more than 61 million sequences.

Plant Molecular Work and Molecular Markers Standard materials and methods for plant molecular work are described by R. D. D. Croy, "Plant Molecular Biology Labfax" (jointly published by BIOS Scientific Publications Ltd (UK) and Blackwell Scientific Publications, UK (1993)) and by D. R. Duncan et al., "Methods in Molecular Biology, Plant Cell and Tissue Culture" (Humana Press, Clifton, N.J. (1990)).

The experiments that led to the methods of the present invention were facilitated by the use of genomic marker assisted selection.

Molecular markers can help plant breeders relatively quickly and accurately select critical traits that enhance plants for the agricultural, horticultural, viticultural, and ornamental industries. They can also help quality assurance personnel make appropriate decisions with respect to hybrid, varietal and inbred purity.

The application of DNA-based markers allows a plant breeder to identify physical characteristics at the molecular level, thus lending a scientific hand in creating and replicating plant varieties. Plant breeding and seed production programs can be enhanced by applying molecular markers for trait selection and mapping, or variety and hybrid genotyping. They provide vehicles for locating and comparing loci regulating quantitative traits requires a segregating population of plants. Each one may be genotyped using molecular markers.

A molecular marker showing polymorphism between the parents of a population which is closely-linked to a gene regulating a particular trait will mainly co-segregate with that gene and the observable trait (i.e., segregate according to the phenotype if the gene has a large effect). Thus, if plants are grouped according to expression of the trait, and extreme groups are tested with that polymorphic marker, the frequency of the two marker alleles present within each of the two bulks should deviate significantly from the ratio of 1:1 expected for most populations. As chromosomal locations of many molecular markers have now been determined in many species, the map location of closely-linked genes can, therefore, be deduced without having to genotype every individual in segregating populations. This can be used with composite populations of maize and other crops and plants to locate quantitative trait loci that are associated with various traits.

Conventional plant breeding, in contrast, is primarily based upon phenotypic selection of desired individuals among segregating progenies resulting from directed hybridization. In some instances, plants from segregating populations can be grouped according to phenotypic expression of a trait, and tested for differences in allele frequency between the population bulks using bulk segregant analysis (BSA) or other methods. The same probes used for making a genetic map, such as isozyme, RFLP, RAPD, and the like, can be used for BSA. However, although strides have been made in crop improvement through phenotypic selections for agronomically desirable traits, considerable difficulties are often encountered during such process. These difficulties may arise from genotype-environmental interactions, epistatic and pleotropic effects, or a host of other factors. Sweet corn mutant allele identification and quantification is particularly encumbered by the lack of phenotypically assisted identification and selection.

Even if an enzymatic basis for a particular mutant gene is not known, and the nucleotide sequence for the gene encoding the enzyme is not known, and is not present in the Maize Genetics and Genomics or GenBank databases, the inheritance of the gene can still be determined by those having ordinary skill in the art by following nearby molecular markers on the chromosome including the gene, as is described in the Examples section herein in detail.

Primers for the molecular markers that were used in the Examples appearing herein are publicly available, and may be found in the Maize Genetics and Genomics database at the Internet site maizegdb dot org. The following are primers for examples of useful molecular markers.

Primers for Molecular Markers for the se1 Allele on Chromosome 2

```
umc1551:
CACCGGAACACCTTCTTACAGTTT

CGAAACCTTCTCGTGATGAGC bnlg1520:
TCCTCTTGCTCTCCATGTCC

ACAGCTGCGTAGCTTCTTCC phi427434:
CAACTGACGCTGATGGATG

TTGCGGTGTTAAGCAATTCTCC umc2077:
CTGGTTCGGATGCAAGTAGTCAG

AAACTCACTGAACATGATCCTGGC
```

Primers for Molecular Markers for the sh2 Allele on Chromosome 3

```
umc2174:
ACATAAATAAAACGTGTGCCGCAG

GTACGTACGCAGCCACTTGTCAG dupssr33:
GTGCTTGGGACAAAAAGG

AGTCCACTCCAGAGGATG bmc1257:
CGGACGATCTTATGCAAACA

ACGGTCTGCGACAGGATATT umc2277:
CTCTTCACGCTCAATAAACCCAGT

TAACTGCAGAAACGGTGGTCAATA
```

Primers for Molecular Markers for the su1 Allele on Chromosome 4

```
phi295450:
CCTTTTCATGTTGCTTTCCC

GCCCAATCCTTCCTTCCT phi308090:
CAGTCTGCCACGAAGCAA

CTGTCGGTTTCGGTCTTCTT phi076:
TTCTTCCGCGGCTTCAATTTGACC

GCATCAGGACCCGCAGAGTC phi079:
TGGTGCTCGTTGCCAAATCTACGA

GCAGTGGTGGTTTCGAACAGACAA
```

Commercially available maize marker libraries, specifically, simple sequence repeats (SSR), may be used for trait identifications, and may be procured from sources that are known by those having ordinary skill in the art. For example, STA Laboratories (Longmont, Colo.) provides commercially available molecular marker and mapping services in connection with seeds and plant breeding, as well as hybrid purity and varietals identification using high resolution Isoelectric Focusing Electrophoresis (IEF). This company provides molecular services for an identification, and incorporation of, specific sweet corn mutant alleles.

In the experiments that led to the methods of the present invention, commercially available maize marker libraries, specifically, simple sequence repeats (SSR), were obtained for trait identifications, and approximately 330 SSR markers were tested, primarily targeting the sugary-1 (su1), sugary enhancer-1 (se1) and shrunken-2 (sh2) mutant endosperm allele published genomic chromosomal sites.

In conjunction with the SSR marker libraries, proprietary sweet corn NILs (near isogenic lines) were utilized to evaluate the marker efficacies, as well as to generate specific desirable mutant alleles for combination with the mutant sh2-i gene. Near isogenic lines of specific interest were:

(i) Su1Su1 se1se1 sh2sh2; and (ii) su1su1 se1se1 sh2sh2.

Additional information about the use of molecular marker libraries for plants and genetic maps is present in, A. Kalinski, "Molecular Markers in Plant Genome Analysis" (Diane Publishing Co., 1995); and H. Lorz et al., "Molecular Marker Systems in Plant Breeding and Crop Improvement," (Springer, 2007).

Conditions for Growing and Harvesting Plants

Those having ordinary skill in the art know how to properly and successfully plant, grow and harvest plants, such as sweet corn. Typically, for example, sweet corn is grown in soil having a pH ranging from about 6 to about 6.5 in full sun, with a planting depth of about 1 inch. Fertilization is typically performed when the sweet corn plants reach about 12" in height for tall varieties, and from about 18" to about 24" in height for other varieties. The sweet corn plants are typically harvested at approximately 64 days after seedlings emerge. As is known by those having ordinary skill in the art, the foregoing conditions may be varied.

Publications that describe how sweet corn and other plants can be planted, grown and harvested include B. R. Lerner et al., "Growing Sweet Corn," Department of Horticulture, Purdue University Cooperative Extension Service, Vegetables HO-98-W, 1-3 (2001); J. R. Schultheis, "Sweet Corn Production," North Carolina Cooperative Extension Service, North Carolina State University, Revised 12/94; D. L. Larson, "Supersweet Sweet Corn: 50 Years in the Making," Inside Illinois Vol. 23, No. 3 (2003), University of Illinois at Urbana-Champaign News Bureau; and "Sweet Corn," Oregon State University, Horticulture 233 webpage.

STA Laboratories (Longmont, Colo.) performs physical purity and vigor analyses using Seedling Vigor Imaging System (SVIS), as well as other seed analyses services. Registered Seed Technologists (RST) ensure uniform testing standards to meet seed labeling regulations in the United Stated and abroad. STA Seed Health Laboratories are USDA accredited through the National Seed Health System (NSHS).

Other Variations

Deletions, additions, and substitutions of the nucleotide sequences encoding portions or all of the mutant alleles that are described herein are contemplated as being within the scope of the present invention, so long as substantially the same phenotype and characteristics observed with the conventional (unaltered) nucleotide sequence is exemplified.

The nucleotide mutations of introns contemplated within the scope of the present invention can also be associated with, or used in conjunction with, other mutations of the genes encoding plant AGP polypeptide or encoding other proteins or enzymes. These other mutations include, but are not limited to, mutations in the wild-type sequence that confer other agronomically desirable traits, such as heat stability, disease resistance, and other desirable characteristics in a plant expressing these mutant alleles.

A mutation of the terminal nucleotide of intron 2 of the Shrunken-2 (sh2) genomic nucleotide sequence is specifically exemplified herein. However, mutations of the terminal nucleotide in other Shrunken-2 (sh2) introns are also within the scope of the invention, as long as these confer substantially the same characteristics to a plant expressing the allele as those associated with the mutation at intron 2, i.e., germination and seedling vigor comparable to or better than plants expressing wild-type Shrunken-2 (sh2) allele, but with enhanced food or taste quality of the vegetable comparable to, or better than, that associated with mutants that provide enhanced sweetness, such as the Sh2-R allele, over wild-type. Those having ordinary skill in the art, and having the benefit of the teachings that are described herein, can readily prepare mutations in other introns of the gene, and determine whether the mutated introns confer the desired characteristics to the plants.

Plants that are contemplated within the scope of the invention include, for example, maize, sweet peas, tomatoes, bananas and any other plant in which a high sucrose content of the vegetable or fruit and germination, seedling and plant growth vigor, are desired characteristics. Other plants that are contemplated within the scope of the invention include those that are described elsewhere herein. Also contemplated within the scope of the invention is plant material, such as plant tissue, cells or seeds, that contain the polynucleotides that are described herein.

Additional References

The following additional references may be of interest or helpful in carrying out the present invention: T. Maniatis et al., "Molecular Cloning: A Laboratory Manual" (2d Edition, Cold Spring Harbor Laboratory, Cold Spring Harbor, N.Y., 1989); D. R. McCarty, "A Simple Method for Extraction of RNA from Maize Tissue," Maize Genet. Coop. Newslett. 60: 61 (1986); A. Gutierrex-Rojas, "Phenotypic Characterization of Quality Protein Maize Endosperm Modification and Amino Acid Contents in a Segregating Recombinant Inbred Population," Crop Sci 48, 1714-1722 (2008); L. Hannah et al., "Characterization of Adenosine Diphosphate Glucose Pyrophosphorylases from Developing Maize Seeds," Plant Physiol. 55:297-302 (1975); L. Hannah et al., "Characterization of ADP-Glucose Pyrophosphorylase from Shrunken-2 and Brittle-2 Mutants of Maize," Biochemical Genetics 14(7, 8):547-560 (1976); M. J. Giroux et al., "ADP-Glucose Pyrophosphorylase in Shrunken-2 and Brittle-2 Mutants of Maize," Molecular & General Genetics 243(4):400-408 (1994); L. Shailesh et al., "The AG Dinucleotide Terminating Introns is Important but not always Required for Pre-mRNA Splicing in the Maize Endosperm," Plant Physiology 120(1): 65-72 (1999); M. Clancy et al., "Maize Shrunken-1 Intron and Exon Regions Increase Gene Expression in Maize Protoplasts," Plant Science 98:151-161 (1994); J. Callis et al., "Introns Increase Gene Expression in Cultured Maize Cells." Genes & Development 1:1183-1200 (1987); K. R. Luehrsen et al., "Intron Creation and Polyadenylation in Maize are Directed by AU-rich RNA," Genes & Development 8:1117-1130 (1994); V. L. Van Santen et al., "Splicing of Plant Pre-mRNAs in Animal Systems and Vice Versa" Gene 56:253-265 (1987); V. Vasil et al., "Increased Gene Expression by the First Intron of Maize Shrunken-1 Locus in Grass Species" Plant Physiol. 91:1575-1579 (1989); J. Anderson et al., "The Encoded Primary Sequence of a Rice Seed ADP-glucose Pyrophosphorylase Subunit and Its Homology to the Bacterial Enzyme," The Journal of Biological Chemistry 264(21): 12238-12242 (1989); J. Anderson et al., "Molecular Characterization of the Gene Encoding a Rice Endosperm-Specific ADP Glucose Pyrophosphorylase Subunit and its Developmental Pattern of Transcription," Gene. 97:199-205 (1991); L. Copeland et al., "Purification of Spinach Leaf ADPglucose Pyrophosphorylase," Plant Physiol. 68:996-1001 (1981); M. Morell et al., "Affinity Labeling of the Allosteric Activator Site(s) of Spinach Leaf ADP-glucose Pyrophosphorylase," The Journal of Biological Chemistry 263(2):633-637 (1988); B. Muller-Rober et al., "One of two Different ADP-Glucose Pyrophosphorylase Genes from Potato Responds Strongly to Elevated Levels of Sucrose," Mol. Gen. Genet., 224:136-146 (1990); P. Nakata et al., "Comparison of the Primary Sequences of Two Potato Tuber ADP-Glucose Pyrophosphorylase Subunits," Plant Molecular Biology 17:1089-1093 (1991); T. Okita et al., "The Subunit Structure of Potato Tuber ADPglucose Pyrophosphorylase," Plant Physiol. 93:785-790 (1990); M. Olive et al., "Isolation and Nucleotide Sequences of cDNA Clones Encoding ADP-Glucose Pyrophosphorylase Polypeptides from Wheat Leaf and Endosperm," Plant Molecular Biology 12:525-538 (1989); B. Keith et al., "Monocot and Dicot Pre-mRNAs are Processed with Different Efficiencies in Transgenic Tobacco," EMBO J. 5(10): 2419-2425 (1986); and Z. Kiss-Laszlo et al., "Splicing of Cauliflower Mosaic Virus 35S RNA is Essential for Viral Infectivity," EMJO J. 14(14):3552-3562 (1995).

Sources of Ingredients, Materials and Equipment

All of the ingredients, materials and equipment that are employed in the examples, and generally employed in the methods of the invention, are commercially available from sources that are known by those having ordinary skill in the art, such as Abbott and Cobb, Inc. (Trevose, Pa.), the Maize Stock Center (Urbana/Champaign, Ill.), STA Laboratories (Longmont, Colo.), GenBank (Bethesda, Md.), The Maize Genetics and Genomics Database, the American Tissue Culture Collection (ATCC) (Rockville, Md.), Applied Biosystems (Foster City, Calif.), Response Genetics, Inc. (Los Angeles, Calif.), Transgenomic (Omaha, Nebr.), DiaPharma Group, Inc. (West Chester, Ohio), Biomol GmbH (Hamburg, Germany), DxS Ltd. (Manchester, UK), Invitrogen (Carlsbad, Calif.), Syngenta Seeds, Inc. (Stanton, Minn.), Rogers (Wilmington, Del.), Monsanto Corporation (St. Louis, Mo.), Garst Seed Company (Slater, Iowa), Holden Foundation Seed (Williamsburg, Iowa), The University of Florida (Gainesville, Fla.), Life Technologies (Gaithersburg, Md.), Alpha Innotech Corporation (San Leandro, Calif.), Amersham International PLC (Arlington Heights, Ill.), and Molecular Dynalics (Sunnyvalle, Calif.). For example, Applied Biosystems sells internationally via its web site (applied biosystems dot corn) and otherwise a wide variety of different products and computer software for conducting DNA sequencing, DNA synthesis (by ligation, Capillary Electrophoresis or the like), DNA and RNA modification and labeling, DNA and RNA purification, gene expression, genotyping, PCR, peptide synthesis, protein sequencing, transcription, translation, various assays, and the like, such as expression vectors, probes, primers, which may be readily employed by those having ordinary skill in the art for carrying out the present invention.

The following examples describe and illustrate the methods of the present invention. These examples are intended to be merely illustrative of the present invention, and not limiting thereof in either scope or spirit. Those of ordinary skill in the art will readily understand that variations of certain of the conditions and/or steps employed in the procedures described in the examples can be employed. While these experiments have been performed using sweet corn kernels and plants, the same procedures that are described therein may be employed with other plant seeds and plants, for example, those that are described elsewhere herein.

The tables below summarizes different sweet corn parent NIL lines and sweet corn hybrid varieties, and their various characteristics (referred to in the Examples as the "Characteristics Tables"), that were prepared in the various examples that are set forth below, and that were assigned particular designations, including various single, double or triple homozygous recessive allelic combinations of the sugary (su), sugary enhancer-1 (se) and shrunken-2 (sh2) mutant genes employed in the male parent lines, with all hybrids including the sh2-i gene in their genomes. In these tables, "in." refers to inches and "No." refers to number.

Seed deposits made with the American Type Culture Collection (ATCC) are described in two separate sections of the "Examples" section of the application, with some (relating to Examples 1-5) being discussed at the end of Example 5 and others (relating to Examples 6-8) being discussed at the end of Example 8.

| Example Number | Parent or Hybrid | Designation | Allelic Combination | Use of Molecular Markers |
|---|---|---|---|---|
| 2 | Hybrid | ACX SS 7501Y | su1su1 se1se1 sh2sh2-i | Yes |
|   | Parent (Female) | AC 199Y | su1su1 se1se1 sh2-i sh2-i | Yes |
|   | Parent (Male) | AC 195Y | su1su1 se1se1 sh2sh2 | Yes |
| 3 | Hybrid | ACX SS 7078Y | su1su1 se1se1 sh2sh2-i | Yes |
|   | Parent (Female) | AC 199Y | su1su1 se1se1 sh2-i sh2-i | Yes |
|   | Parent (Male) | AC 128Y | su1su1 se1se1 sh2sh2 | Yes |
| 3 | Hybrid | ACX SS 7403RY | su1su1 se1se1 sh2sh2-i | Yes |
|   | Parent (Female) | AC 199Y | su1su1 se1se1 sh2-i sh2-i | Yes |
|   | Parent (Male) | AC 215Y | su1su1 se1se1 sh2sh2 | Yes |
| 4 | Hybrid | AC 151Y | Su1su1 Se1se1 sh2sh2-i | No |
|   | Parent (Female) | AC 103Y | Su1Su1 Se1Se1 sh2-i sh2-i | No |
|   | Parent (Male) | AC 107Y | su1su1 se1se1 sh2sh2 | No |
| 4 | Hybrid | AC 188W | Su1su1 Se1Se1 sh2sh2-i | No |
|   | Parent (Female) | AC 106 W | Su1Su1 Se1Se1 sh2-i sh2-i | No |
|   | Parent (Male) | AC 163W | su1su1 Se1Se1 sh2sh2 | No |
| 7 | Hybrid | ACX SS 1082Y sh2-i | Su1Su1 Se1Se1 sh2sh2-i | No |
|   | Parent (Female) | AC 157Y-i | Su1Su1 Se1Se1 sh2-i sh2-i | No |
|   | Parent (Male) | AC 144Y | Su1Su1 Se1Se1 sh2sh2 | No |
| 8 | Hybrid | ACR SS 4500Y | Su1su1 Se1Se1 sh2sh2-i | No |
|   | Parent (Female) | AC 098Y-i | Su1Su1 Se1Se1 sh2-i sh2-i | No |
|   | Parent (Male) | AC 233Y | su1su1 se1se1 sh2sh2 | No |
| 8 | Hybrid | ACR SS 4501Y | Su1su1 Se1Se1 sh2sh2-i | No |
|   | Parent (Female) | AC 157Y-i | Su1Su1 Se1Se1 sh2-i sh2-i | No |
|   | Parent (Male) | AC 241Y | su1su1 Se1Se1 sh2sh2 | No |

Characteristics Table
(Parental Sweet Corn Lines)

|  | AC 199Y | AC 128Y | AC 215Y | AC 098Y-i | AC 233Y | AC 157Y-i | AC 241Y | AC 195Y | AC 144Y |
|---|---|---|---|---|---|---|---|---|---|
| Maturity | 75 Day | 72 Day | 72 Day | 79 Day | 79 Day | 80 Day | 76 Day | 74 Day | 72 Day |
| Height | 66 in. | 70 in. | 72 in. | 60 in. | 73 in. | 66 in. | 63 in. | 72 in. | 68 in. |
| No. Tillers | 1.5 | 1.8 | 2.0 | 0.3 | 1.6 | 0.5 | 1.4 | 1.8 | 1.2 |
| Glume Color | Green | Green | Green | Green | Green | Green | Green | Green | Green |
| Tassel Laterals | 14 | 10 | 10 | 18 | 20 | 18 | 16 | 16 | 16 |
| Ear Length | 6.8 in. | 6.0 in. | 6.2 in. | 5.8 in. | 7.3 in. | 5.8 in. | 6.5 in. | 6.8 in. | 6.0 in. |
| Ear Diameter | 1.8 in. | 1.5 in. | 1.5 in. | 1.8 in. | 1.9 in. | 1.8 in. | 2.0 in. | 1.8 | 1.5 in. |
| Ear Shape | Cylindrical | Cylindrical | Cylindrical | Cylindrical | Cylindrical | Cylindrical | Cylindrical | Cylindrical | Cylindrical |
| Kernel Depth | 10 mm | 6 mm | 6 mm | 8 mm | 12 mm | 8 mm | 14 mm | 10 mm | 8 mm |
| No. Kernel Rows | 14-16-18 | 14-16 | 14-16-18 | 14-16-18 | 16-18 | 14-16-18 | 16-18-20 | 16-18-20 | 14-16 |
| Kernel Color | Yellow | Yellow | Yellow | Yellow | Yellow | Yellow | Yellow | Yellow | Yellow |

| Characteristics Table (Hybrid Sweet Corn Lines) | | | | | | |
|---|---|---|---|---|---|---|
| | ACX SS 7501Y | ACX SS 7078Y | ACX SS 7403RY | ACR SS 4500Y | ACR SS 4501Y | ACX SS 1082Y |
| Maturity | 76 Days | 78 Days | 75 Days | 77 Days | 78 Days | 79 Days |
| Height | 72 in. | 80 in. | 84 in. | 77 in. | 73 in. | 84 in. |
| No. Tillers | 1.5 | 0.8 | 1.5 | 1.5 | 1.0 | 1.0 |
| Glume Color | Green | Green | Green | Green | Green | Green |
| Tassel Laterals | 18 | 14 | 12 | 24 | 28 | 22 |
| Ear Length | 8.0 in. | 8.25 in. | 8.25 in. | 8.25 in. | 8.5 in. | 8.5 in. |
| Ear Diameter | 1.8 in. | 2.0 in | 1.9 in. | 1.8 in. | 2.1 in. | 1.78 in. |
| Ear Shape | Cylindrical | Cylindrical | Cylindrical | Cylindrical | Cylindrical | Cylindrical |
| Kernel Depth | 9 mm | 12 mm | 10 mm | 9 mm | 11 mm | 10 mm |
| No. Kernel Rows | 16 | 16-18 | 16-18 | 16-18 | 16-18-20 | 16-18 |
| Kernel Color | Yellow | Yellow | Yellow | Yellow | Yellow | Yellow |

Example 1

Construction of Parental Inbred Near Isogenic Lines (NILs)

Triple Allelic Combinations of the Sugary (su), Sugary Enhancer-1 (se1) and Shrunken-2 (sh2) Endosperm Mutant Genes In the experiments that are described in this example, in order to attempt to solve the problem of manipulating the regulation of carbohydrate accumulation, and pericarp tenderness, in sweet corn varieties containing the mutant sh2-i gene, appropriate parental near isogenic lines (NILs) were constructed and tested, using methods that are described below and/or known by those having ordinary skill in the art, of the following triple allelic genotype combinations:
(1) Su1Su1Se1Se1 sh2sh2=conventional commercial "supersweet" type with standard eating quality
    (including one homozygous recessive endosperm mutant allele)
(2) Su1Su1 se1se1 sh2sh2=conventional commercial "supersweet" type with very good eating quality
    (including a double homozygous recessive endosperm mutant allelic combination)
(3) su1su1 se1se1 sh2sh2=exotic limited commercial type with exceptional eating quality
    (including a triple homozygous recessive endosperm mutant allelic combination)
Construction of Parental NILs STA Laboratories (Longmont, Colo.) assisted in providing the molecular services involved in the identification, and incorporation, of specific sweet corn mutant alleles into the genomes of maize plants. Commercially-available appropriate maize marker libraries, specifically, simple sequence repeats (SSR), were obtained for trait identifications from STA Laboratories, and originated from libraries published by Pioneer Hi-Bred International, Inc. (Johnston, Iowa), a developer and supplier of advanced plant genetics to farmers worldwide. The markers were all publically available from the maize genetics and genomics website maizegdb dot org. The markers that start with the designation "phi" were developed and released to the public by Pioneer Hi-Bred International, Inc. Approximately 330 SSR markers were tested, primarily targeting the su1, se1 and sh2 published genomic chromosomal sites.

The above NILs were backcrossed and self pollinated a sufficient number of times in a manner known by those of ordinary skill in the art to effect an adequate reconstitution of the recurrent parents.

Molecular markers were utilized in a manner known by those of ordinary skill in the art to assist in the identification of su1 and se1 mutant alleles, in particular. These molecular markers were helpful in mutant genotypic identification in that the incorporation of the sh2-i mutant gene provides a dominant phenotype that masks the expression of the su1, se1 or sh2 mutant genes.

Specifically contemplated for use initially was the su1su1 se1se1 sh2sh2 NIL triple recessive allelic combination. This specific combination was chosen to combine starch defective genes that could possibly offset the rapid build up of starch that is associated with the incorporation of the mutant sh2-i gene into the maize genome. Backcrossing of the su1su1 se1se1 sh2sh2 triple recessive NILs as recurrent parents was then initiated using a donor sh2-i gene source provided by Dr. C. L. Hanna of the University of Florida (Gainesville, Fla.). (The mutant sh2-i gene, and its sequence, is shown and described in detail in U.S. Pat. No. 6,184,438 B1). This donor source was test crossed to appropriate genetic lines to determine the status of the su1 and se1 genes. Test crossing results confirmed that the donor sh2-i gene source had a genotype of Su1Su1 Se1Se1 relative to the sugary-1 (su1) and sugary enhancer-1 (se1) genes.

Ears of corn from BC1-S1 populations were phenotypically examined. (BC1-S1 is an A&C breeding population, and the term "BC1-S1" is a genetic or plant breeder's word for point in time relating to the progress of the final product. The final product in this example is a reconstruction of the recurrent parent in which the sh2-i mutant allele is to be added.) Only those BC1-S1 ears segregating su 1, sh2 and sh2-i kernel types were selected for continued backcrossing. The mutant sh2sh2 morphological sweet corn kernel appearance is distinct from other varieties of sweet corn in that dry seeds (kernels) appear to be translucent, highly collapsed, and wrinkled. The mutant sh2-i sweet corn kernel phenotypes, in contrast, are smooth, heavier, well filled and nearly like that of flint field corn in appearance (having round kernels with smooth coats). Kernel phenotypes were confirmed with molecular markers, as is discussed elsewhere herein, and as is shown in FIG. 10. The limitation of but two phenotypes on BC2-S1 selected ears resulted in the verification that the kernels expressing the sh2-i gene were layered over an su1su1 sh2sh2 genetic background.

Kernels from the above BC1-S1 selected sh2-i phenotypes (su1su1 se1se1 sh2sh2 NIL inbred sh2-i conversion kernels) were then planted and test crossed to se1se1 genetically confirmed inbreds. Molecular marker genetic confirmations were conducted concomitantly. Only plants exhibiting homozygous se1 test cross positives and se1 molecular confirmations were kept for continued backcrossing, selfing and test crossing. The backcrossing, selfing and test crossing, and molecular confirmations, were continued through six cycles. At this point, it was considered that the original triple allelic su1su1 se1se1 sh2sh2 NILs were adequately converted with the inclusion of the mutant sh2-i gene in their genomes. These phenotypically and molecularly confirmed maize ears resulted in sh2-i kernels being layered over su1su1 se1se1 genetic backgrounds. The resultant kernel phenotype was predominantly similar to that of kernels expressing the sh2-i gene in appearance, with the kernels being smooth, full, and relatively heavy in appearance.

Laboratory Warm and Cold Germination Testing and Organoleptic Taste Testing

Laboratory warm towel and cold soil germinations were conducted using methods known by those having ordinary skill in the art on the su1su1 se1se1 sh2sh2 NIL inbred sh2-i conversion kernels to verify enhanced seedling performances that are associated with the mutant sh2-i gene (and the donor sh2-i). Actual cold field soil testing was conducted, as well, for further verification of enhanced germination and seedling vigor. The laboratory warm towel and cold soil germinations were conducted at 45° F. (7.22° C.) and 80° F. (26.67° C.), respectively. Moisture levels were measured according to published recommendations for germination testing protocols of the Association of Official Seed Analysts, Inc. (AOSA) (Ithaca, N.Y.). The sweet corn kernels were planted in a conventional manner known by those having ordinary skill in the art using accredited plastic germination trays sanctioned by the AOSA. In some of these tests, in particular, a sweet corn female parent line designated as AC 199Y (discussed in Examples 2 and 3), having the mutant sh2-i gene incorporated into its genome, was tested against its isogenic counterpart, which did not include the sh2-i gene in its genome.

Organoleptic taste testing of the su1su1 se1se1 sh2sh2 NIL kernels in comparison with kernels of its sh2-i counterpart (su1su1 se1se1 sh2sh2 NIL inbred sh2-i conversion kernels) was conducted using methods known by those having ordinary skill in the art, and very advantageously resulted in only slight elevations in starch synthesis, which were not considered to be significant. Organoleptic testing was conducted by a taste panel of experienced staff of personnel (5-8 individuals) employed by Abbott & Cobb, Inc. (Trevose, Pa.). Generally, six corn ears per item were selected from three replications each for any particular planting site. Test corn ears were maintained at ambient temperatures (ranging from about 80-88° F. or 26.66-31.11° C.). Pedigrees of test materials were withheld from taste panel participant to reduce any varietal taste bias or pre-disposition.

Germination and seed viability can be determined by means of selected well-known university or commercial laboratory enterprises that comply with Association of Official Seed Analysis (AOSA) rules for germination testing protocols, such as STA Laboratories (Longmont, Colo.), Midwest Laboratories (Omaha, Nebr.), Biogenetic Services Inc. (Brookings, S. Dak.) and others.

Association of Official Seed Analysts, Inc. (AOSA): Seed Testing Protocols

As is well known by those having ordinary skill in the art, the seed testing protocols of the Association of Official Seed Analysts, Inc. (AOSA) (Ithaca, N.Y.), an organization of member laboratories, serve universally as the standard for seed germination, seedling vigor, kernel organoleptic taste and pericarp tenderness and other seed and plant testing. Members of this organization include official state, federal, university and other seed laboratories across the United States and Canada. To assure a high standard of quality, many members of the AOSA member laboratories have acquired AOSA Certified Seed Analyst status through extensive training followed by a mandatory certification testing process.

The primary functions of the AOSA are to: (i) establish the AOSA Rules for Testing Seeds which are generally adopted by most states in the United States as the rules for testing seeds in their respective states; (ii) contribute to the refinement and modification of the rules and procedures for seed testing; (iii) ensure that seed testing procedures are standardized between analysts and between laboratories; and (iv) influence and assist in enforcement of appropriate seed legislation at state and federal levels.

The official AOSA Internet web site (aosaseed dot corn) provides direct Internet links to several other official Internet web sites relating to seeds and/or plants, including those for the United States Department of Agriculture (USDA) Seed Regulatory and Testing Programs, the Association of American Seed Control Officials (AASCO), the Association of Official Seed Certifying Agencies (AOSCA), the American Seed Trade Association (ASTA), the Canadian Food Inspection Agency (CFIA), the Commercial Seed Analysts Association of Canada (CSAAC), the National Association of State Departments of Agriculture (NASDA), the Front Range Seed Analysis, the International Seed Testing Association (ISTA), Seed Quest SeedImages dot corn and the Society of Commercial Seed Technologists (SCST). The official AOSA Internet web site also includes an extensive product and vendor web site, which includes products directed towards seed analysis computer software, DNA products, markers, reagents, sequencing, Western blots and the like.

The AOSA handbooks and rules regarding a variety of different topics, including its 2009 rules for testing seeds, a seed vigor handbook, a seed moisture handbook, and a seed technology journal, are publicly available for computer downloading and/or reading from its official Internet web site at aosaseed dot com. For example, the AOSA *Seed Vigor Testing Handbook* is a comprehensive revision of the 1983 and 2002 versions thereof that set the industry standard for seed vigor testing. Further, the Seed Technology Journal, which is also available at the Internet web site seedtechnology dot net is an international journal containing scientific and technological papers in all areas of seed science and technology. The emphasis in this journal is on applied and basic research in seed physiology, pathology and biology that may relate to seed development, maturation, germination, dormancy and deterioration. Studies on seed production, sampling, testing, conditioning, distribution and storage are also included. Short communications from seed analysts and technologists are encouraged and published as Seed Tech Notes. These notes include new techniques, standardization of laboratory tests and documentation of anatomical and pathological observations of seed and seedling development. The journal also includes timely review articles in all areas of seed technology that may relate directly to the seed industry.

Molecular Map of Samples of Inbred Parental NILs having Various Triple Mutant Endosperm Allelic Combinations (FIG. 10)

FIG. 10 provides a molecular map for samples of individual inbred parental NILs having the triple mutant endosperm allelic combinations shown below. In this molecular map:

- Samples 1-2 (017 and 044, respectively) are genetically: Su1Su1Se1Se1 sh2sh2 (including a single homozygous recessive mutant endosperm allele).
- Samples 3-7 (006, 007, 009, 047 and 637, respectively) are genetically: Su1Su1se1se1 sh2sh2 (including a double homozygous recessive mutant endosperm allelic combination).
- Samples 8-13 (001, 046, 048, 049, 109 and 354, respectively) are genetically: su1su1 se1se1 sh2sh2 (including a triple homozygous recessive mutant endosperm allelic combination).
- Sample 14 is the donor source for the mutant sh2-i gene (received from The University of Florida, Gainesville, Fla.).

Highlighted in FIG. 10 are the purported chromosomal regions characterized as the Se1, Su1 and Sh2 sites. Numerous molecular markers were useful in genotypic identification. In particular, the molecular marker designated as "umc 1551" was efficacious in se1se1 characterizations, and the molecular marker designated as "phi 079" was similarly useful in making su1su1 identifications. Numerous other molecular markers that are shown in FIG. 10 were helpful singly, or in combination, in making marker assisted assignments.

Example 2

Production using Molecular Markers, and an se1se1/su1su1 Genetic Background, and Testing of Sweet Corn Hybrid ACX SS 7501Y sh2-i Female Parents in Combination with Male Parents having Triple Recessive Allelic Combinations In the experiments that are described in this example, the sweet corn hybrid NIL designated as ACX SS 7501Y having a desired triple allelic combination was developed utilizing the sh2-i gene, the parental sweet corn NILs having the designations shown below and molecular markers, and then tested in the manner described below.

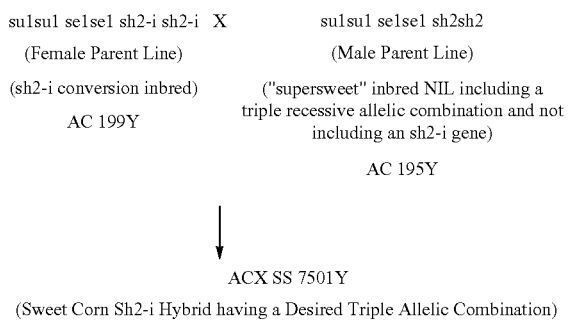

su1su1 se1se1 sh2-i sh2-i    X    su1su1 se1se1 sh2sh2
(Female Parent Line)              (Male Parent Line)
(sh2-i conversion inbred)         ("supersweet" inbred NIL including a
                                  triple recessive allelic combination and not
AC 199Y                           including an sh2-i gene)
                                  AC 195Y ACX SS 7501Y
(Sweet Corn Sh2-i Hybrid having a Desired Triple Allelic Combination)

Construction of Hybrid ACX SS 7501Y

The mutant sh2-i gene was incorporated into a series of selected inbred parental NIL sweet corn lines in the manner that is discussed in Example 1. These inbred parental NIL sweet corn lines were chosen on the basis of desirable horticultural and seed production criteria, as is discussed in Example 1 and elsewhere herein.

It was discovered through a significant amount of experimentation and organoleptic taste and pericarp tenderness testing of various different sweet corn hybrids produced using a female parent line and a male parent line that both included the sh2-i gene in their genomes that unacceptable starch synthesis and buildup following the peak eating stage of resulting hybrids developed from these lines (producing a starchy taste and sweet corn kernels that were not tender) disallowed the process of assembling hybrids based upon the use of two sh2-i parental corn lines. The best alternative was determined by this experimentation and testing to be the generation of hybrids comprised of: (i) an sh2-i conversion inbred female sweet corn line; and (ii) a high-quality conventional male parental sweet corn line.

In view of the results of the above-described experimentation and organoleptic taste and pericarp tenderness testing, the inventor decided to use the mutant sh2-i allele only in female sweet corn parent lines (i.e., that the sh2-i conversion inbred sweet corn lines would be used only as the female parent lines, and not as the male parent lines, in commercial maize production. This decision was based upon a number of factors, including those discussed above. One such factor for using the sh2-i conversion parents as females was based upon the fact that kernel pericarp and resulting seed coat is 2N and maternally inherited. Utilization of the sh2-i conversion parents as female parents, thus, preserves the very advantageous enhanced germination and seedling vigor characteristic provided by the sh2-i gene, and expressed as a function of the female parental line. In addition, commercial seed production yields appear to be greatly enhanced as an artifact of the superior germination and seedling vigor traits provided to sweet corn hybrids by the sh2-i female seed parental lines. Sh2-i conversion inbred female parent sweet corn lines were determined to provide hybrids developed therewith the multiple beneficial traits of having an enhanced germination, an enhanced seedling vigor and an enhanced commercial seed production yield.

In view of the above, the genotypes of the male parental lines selected for use in hybrid combinations with the sh2-i conversion female lines were chosen based upon their ability to provide desirable horticultural qualities to sweet corn hybrids produced using such lines, but primarily by its contribution to producing sweet corn hybrids having a high eating quality, such as a sweet taste and a tender kernel pericarp. Thus, male parental genotypes were utilized that contained su1su1 se1 se1 sh2sh2 triple honiozygous recessive mutant endosperm allelic combination. The triple homozygous recessive lines su1su1 se1se1 sh2sh2 generally tend to be proportionately higher in sucrose as compared to similar double homozygous recessive mutant endosperm lines, such as su1su1 Se1 Se1 sh2sh2 or su1su1 sh2sh2, and thus were determined to be more desirable for use as the male parent lines for producing hybrids in the manners that are described herein. (W. F. Tracy, A. R. Hellaurer (ED) *Specialty Corns*, 147-187 (CRS Press, Boca Raton, Fla. (1994).) (The double homozygous recessive su1su1 sh2sh2 genotypes, however, including su1su1 Se1Se1 sh2sh2, as well as the triple homozygous recessive su1su1 se1se1 sh2sh2 genotypes, which are characteristic of male sweet corn parent lines that are described herein, are also desirable for use in the production of sweet corn hybrids in that they are exceptionally high in sugar with very tender kernel pericarps. The su1su1 sh2sh2 homozygous recessive genotypic components (i.e., the double homozygous recessive su1su1 and sh2sh2 mutant endosperm alleles present in both the above double and triple homozygous recessive endosperm mutant allelic combination) of all of these male sweet corn parent lines provide significant holding abilities (retention of higher sugars and tender kernel pericarps) in hybrid combination with the female sh2-i conversion sweet corn lines that are described herein (i.e., resulting hybrids include these traits).)

One resulting sweet corn hybrid containing the sh2-i gene of particular interest was designated as hybrid ACX SS 7501Y. This hybrid line differed in a beneficial manner from other hybrids prepared in this example in performance relative to geographical growing regions and/or market requirements, and its characteristics are described in detail in the Characteristics Table (Hybrid Sweet Corn lines) that is set forth hereinabove prior to Example 1. The Characteristics Table (Parental Sweet Corn lines) describes the characteristics in detail of the parent sweet corn lines that were employed to develop this hybrid line.

Laboratory Warm and Cold Germination Testing and Organoleptic Taste and Pericarp Tenderness Testing Organoleptic evaluation of sweet corn hybrids that were assembled in the above fashion, including hybrid ACX SS 7501Y, were determined using methods that are known by those of ordinary skill in the art, as is discussed in great detail in Example 1. Such hybrids were shown to provide significant benefits to corn growers in that germination, seedling vigor, and overall crop productivity was elevated in comparison to the same or similar sweet corn varieties not including the sh2-i gene in their genomes. Additionally, consumers of these sweet corn hybrid products receive valuable benefits relating to product eating quality (sweet taste and kernel pericarp tenderness) and extended shelf life.

Figure 7:
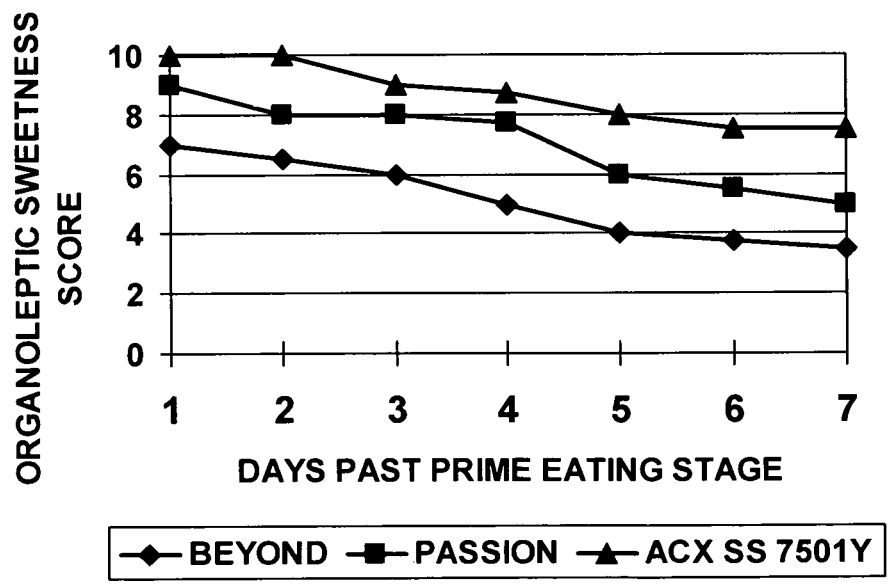
FIG. 7 is a line graph that shows organoleptic average sugar (sweetness) scores for the sweet corn varieties Beyond (not including the sh2-i gene), Passion (not including the sh2-i gene) and ACX SS 7501Y (including the sh2-i gene) in the seven day period immediately following the prime eating stage (at a level of approximately 75% moisture). It illustrates the comparative organoleptic sugar levels among these three sweet corn varieties over this seven-day period of time.

FIG. 7 illustrates the comparative organoleptic sweetness (sugar) scores among three sweet corn varieties over a period of seven days directly following the peak eating stage. The commercial variety Passion is sold and distributed through Monsanto (St. Louis, Mo.). The commercial variety Beyond is sold and distributed by Abbott and Cobb, Inc. (Trevose, Pa.), and has served as a standard, primarily in the Southeast commercial shipping markets. The variety designated as ACX SS 7501Y is a hybrid variety that was produced in accordance with Examples 1 and 2 using a female parent line designated as AC 199Y and a male parent line designated as AC 195Y. The organoleptic sweetness (sugar) scores range from 1 (very little sweetness with a considerable starch taste) to 10 (sweet with little or no starch taste). FIG. 7 shows that the ACX SS 7501Y hybrid corn variety very advantageously maintained an organoleptic sweetness score above both the Passion and Beyond corn varieties at all times during this 7-day period and, in contrast with the Passion and Beyond corn varieties, maintained a score of 10 on days 1 and 2 past prime eating stage. FIG. 7 also shows that the ACX SS 7501Y hybrid corn variety had an organoleptic sweetness score of almost 8 on day 7 (in comparison with a score of about 5 for Passion, and a score of about 3 for Beyond). Over the seven day testing period, the ACX SS 7501Y hybrid corn variety held, and maintained, very high sweetness levels compared to the comparison varieties of Passion and Beyond.

Figure 8:
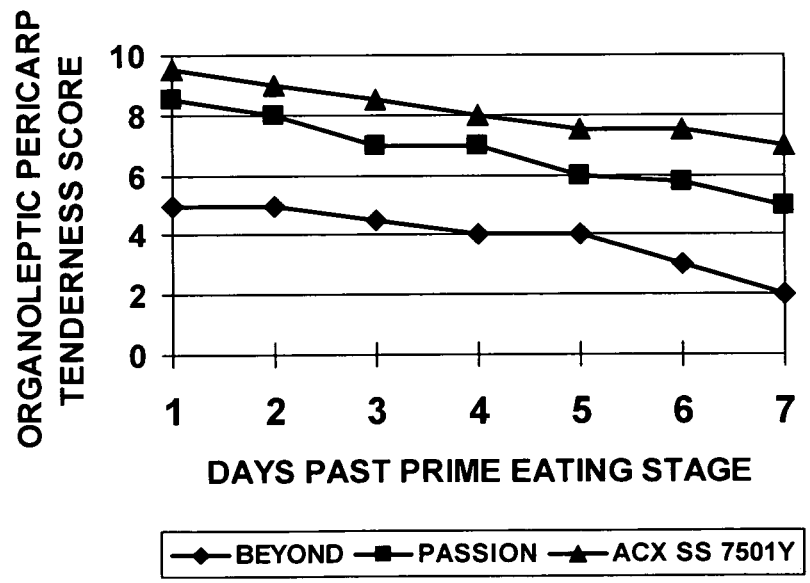
FIG. 8 is a line graph that shows organoleptic average pericarp tenderness scores for the sweet corn varieties Beyond (not including the sh2-i gene), Passion (not including the sh2-i gene) and ACX SS 7501Y (including the sh2-i gene) in the seven day period immediately following the prime eating stage (at a level of approximately 75% moisture). It illustrates the comparative organoleptic pericarp tenderness levels among these three sweet corn varieties over this seven-day period.
Figure 9:
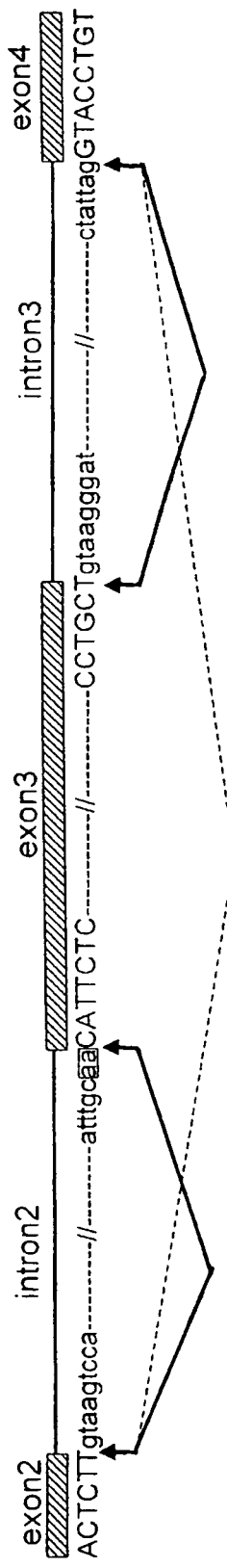
FIG. 9 shows a schematic representation of the genomic sequence bearing the splice site alterations of the mutant shrunken-2i (sh2-i) allele (exon 1-4). The point mutation that altered the 3' splice site AG to AA of intron 2 in mutant sh2-i is boxed. Arrows joined by lines mark the donor and acceptor sites used during RNA splicing to generate the mutant transcripts.

FIG. 8 shows the comparative organoleptic pericarp and tenderness scores among the same three sweet corn varieties that are shown in FIG. 7 over a period of seven days directly following the peak eating stage. The organoleptic pericarp and tenderness scores range from 1 (very tough pericarp) to 10 (very tender pericarp). FIG. 8 shows that the ACX SS 7501Y hybrid corn variety very advantageously maintained an organoleptic pericarp and tenderness score above both the Passion and Beyond corn varieties at all times during this 7-day period. It also shows that the ACX SS 7501Y hybrid corn variety had an organoleptic pericarp and tenderness score of about 7 on day 7 (in comparison with a score of about 5 for Passion, and a score of about 2 for Beyond). Over the seven day testing period, the ACX SS 7501Y hybrid corn variety held, and maintained, very high pericarp tenderness levels compared to the comparison varieties of Passion and Beyond. The ACX SS 7501Y hybrid corn variety was observed to be very tender, and to have an excellent holding ability. This hybrid line differed in a beneficial manner from other hybrids prepared in this example in performance relative to geographical growing regions and/or market requirements, and its characteristics are described in detail in the Characteristics Table (Hybrid Sweet Corn lines) that is set forth hereinabove prior to Example 1.

Example 3

Production using Molecular Markers, and a se1se1/su1su1 Genetic Background, and Testing of Sweet Corn Hybrids ACX SS 7078Y and ACX SS 7403RY sh2-i Female Parents in Combination with Male Parents having Triple Recessive Allelic Combinations In the experiments that are described in this example, additional sweet corn hybrid NILs having desired triple allelic combinations were developed utilizing the sh2-i gene and molecular markers, and then tested in the manner described below.

Construction of Hybrids ACX SS 7078Y and ACX SS 7403RY

The additional sweet corn hybrids were assembled according to the same breeding procedures that are described in Examples 1 and 2 for sweet corn hybrid ACX SS 7501Y. These sweet corn varieties were assembled by layering the sh2-i gene over se1se1 and su1su1 genetic backgrounds utilizing molecular markers, as has been described previously herein.

Two resulting sh2-i sweet corn hybrids of particular interest were designated as ACX SS 7078Y and ACX SS 7403RY, and were developed using the parental sweet corn NILs having the designations shown below. These hybrid lines differed in a beneficial manner from other hybrids prepared in this example in performance relative to geographical growing regions and/or market requirements, and their characteristics are described in detail in the Characteristics Table (Hybrid Sweet Corn lines) that is set forth hereinabove prior to Example 1. The Characteristics Table (Parental Sweet Corn lines) describes the characteristics in detail of the parent sweet corn lines that were employed to develop these hybrid lines.

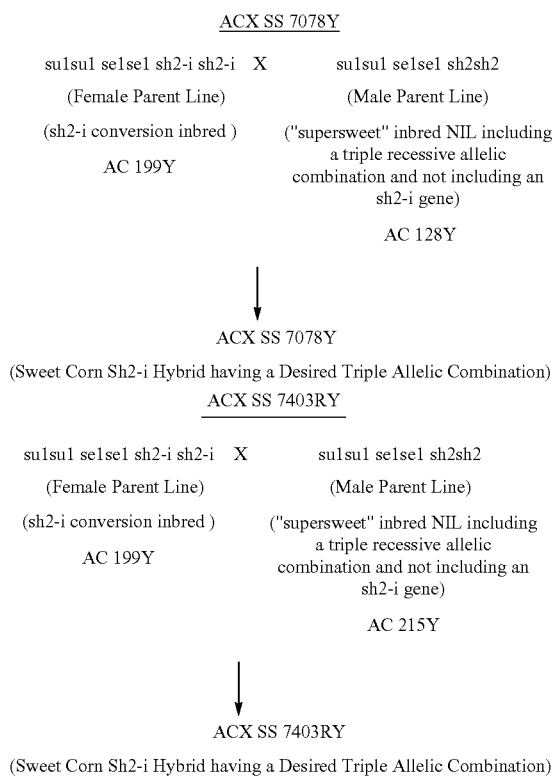

Sweet corn hybrid ACX SS 7078Y, which has the sh2-i mutant allele incorporated into its genome, is an isogenic conversion of the Abbott and Cobb, Inc. commercially-available hybrid designated ACX 1073Y, which does not have the sh2-i mutant allele incorporated into its genome. Similarly, sweet corn hybrid ACX SS 7403RY, which has the sh2-i mutant allele incorporated into its genome, is an isogenic conversion of the Abbott and Cobb, Inc. commercially-available variety designated ACX 7473RY, which also does not have the sh2-i mutant allele incorporated into its genome. In both sh2-i gene containing hybrid developments, these two isogenic sweet corn hybrids were found to be nearly identical for all horticultural and morphological characteristics, when identified using methods that are described herein and/or are known by those having ordinary skill in the art. The identification methods and differential characterization of isogenic comparisons and nomenclature are well known by those having ordinary skill in the plant breeding and similar arts, as well as in scientific communities generally.

Laboratory Warm and Cold Germination Testing and Organoleptic Taste and Pericarp Tenderness Testing Table 3 below provides data resulting from actual comparisons of laboratory warm and cold germination data, as well as organoleptic taste and pericarp tenderness tests, for the sweet corn varieties ACX 1073Y, ACX SS 7078Y, ACX 7473RY and ACX SS 7403RY. Germination data reflect the mean of three replications of 100 kernels each, and germination scores not followed by the same letter are significantly different at the 0.05 probability level via the Duncan's New Multiple Range Test. In Table 3 (and in other tables that are set forth herein), the "a" and "b" designations indicate that the mean values are significantly different at the 0.05 probability level. (The same is true of a "c" designation appearing in other tables set forth herein.) The organoleptic tests regarding sweetness and pericarp tenderness are described previously herein.

Table 3 shows that, in both cases in which the sh2-i mutant gene was added to the sweet corn genomes (hybrids ACX SS 7078Y and ACX SS 7403RY), the isogenic hybrid comparison warm and cold laboratory scores very advantageously were elevated in comparison with the scores of the commercially-available sweet corn varieties which do not include the sh2-i mutant gene in their genomes (ACX 1073 and ACX 7473RY), which is indicative of enhanced field emergence and vigor. Table 3 also shows that the two sweet corn varieties including the mutant sh2-i gene in their genomes (hybrids ACX SS 7078Y and ACX SS 7403RY) very advantageously retained their sweetness (sugar levels) significantly longer (having scores of 8 on Day 7 in the seven day period immediately following the prime eating stage) than the two sweet corn varieties that did not include this sh2-i gene in their genomes (having scores of 6 or 5 on Day 7), and had pericarps that retained their tenderness significantly longer (having scores of 7 on Day 7 in the seven day period immediately following the prime eating stage) than the two sweet corn varieties that did not include this sh2-i gene in their genomes (having scores of 6 or 5 on Day 7). The organoleptic sweetness and pericarp tenderness scores that are present in Table 3 very advantageously demonstrate acceptable eating quality levels along with concomitantly desirable shelf life and holding abilities for hybrids ACX SS 7078Y and ACX SS 7403RY.

TABLE 3

Isogenic Comparisons of Sweet Corn Varieties Including, or not Including, the sh2-i Gene

| Variety | Warm Germination | Cold Germination | Organoleptic Sweetness Score | | | Organoleptic Pericarp Tenderness Score | | |
|---|---|---|---|---|---|---|---|---|
| | | | Day 1 | Day 4 | Day 7 | Day 1 | Day 4 | Day 7 |
| ACX 1073Y (Does not Contain sh2-i Gene) | 92a | 59b | 9 | 8 | 6 | 9 | 8 | 6 |
| ACX SS 7078Y (Contains sh2-i Gene) | 98a | 91a | 9 | 8 | 8 | 9 | 8 | 7 |
| ACX 7473RY (Does not Contain sh2-i Gene) | 91a | 62b | 9 | 7 | 5 | 8 | 6 | 5 |

TABLE 3-continued

Isogenic Comparisons of Sweet Corn Varieties Including, or not Including, the sh2-i Gene

| Variety | Warm Germination | Cold Germination | Organoleptic Sweetness Score | | | Organoleptic Pericarp Tenderness Score | | |
|---|---|---|---|---|---|---|---|---|
| | | | Day 1 | Day 4 | Day 7 | Day 1 | Day 4 | Day 7 |
| ACX SS 7403RY (Contains sh2-i Gene) | 97a | 94a | 10 | 8 | 8 | 9 | 7 | 7 |

Example 4

Production without using Molecular Markers, and a se1se1/su1su1 Genetic Background, and Testing of Sweet Corn Hybrids AC 151Y and AC 188W sh2-i Female Parents in Combination with Male Parents having Double or Triple Recessive Allelic Combinations In the experiments that are described in this example, additional sweet corn hybrid NILs having double and triple allelic combinations were developed utilizing the sh2-i gene, but without the use of molecular markers, and then tested in the manner described below.

Construction of Hybrids AC 151Y and AC 188W

These additional sweet corn hybrids were assembled according to the same breeding procedures that are described in Examples 1, 2 and 3, with the exceptions that the hybrid lines containing the mutant sh2-i gene in their genomes were not assembled utilizing molecular markers, as previously described herein (Examples 1, 2 and 3), and did not incorporate se1se1/su1su1 alleles.

Two resulting sweet corn sh2-i hybrids of particular interest were designated AC 151Y and AC 188W, and were developed using the parental sweet corn NILs having the designations shown below. These hybrids were developed from sh2-i female conversion parent lines not containing the su1 and se1 genes to test eating quality in comparison with sh2-i female parental inbreds constructed utilizing the incorporation of the su1 and se1 genes. It was also considered important to test the effect of using double and triple homozygous recessive male lines with the sh2-i conversion females lines that were not constructed utilizing sequential layering over the su1 and se1 genes.

AC 151Y

Su1Su1 Se1Se1 sh2-i sh2-i    X    su1su1 se1se1 sh2sh2

(Female Parent Line)      (Male Parent Line)

(sh2-i conversion inbred without sequential layering and utility of the su1 and se1 genes)      ("supersweet" inbred line utilizing a triple recessive allelic combination and not including an sh2-i gene)

AC 103Y      AC107Y

↓

AC 151Y (Sweet Corn Sh2-i Hybrid Constructed with Non-sequential Layering of the Female Parent Line, and in Combination with a Triple Recessive Male Parent Line)

AC 188W

Su1Su1 Se1Se1 sh2-i sh2-i    X    su1su1 Se1Se1 sh2sh2

(Female Parent Line)      (Male Parent Line)

(sh2-i conversion inbred without sequential layering and utility of the su1 and se1 genes)      ("supersweet" inbred line utilizing a double recessive allelic combination and not including an sh2-i gene)

AC 106W      AC163W

AC 188W (Sweet Corn Sh2-i Hybrid Constructed with Non-sequential Layering of the Female Parent Line, and in Combination with a Double Recessive Male Parent Line)

These hybrid lines differed in a beneficial manner from other hybrids prepared in this example in performance relative to geographical growing regions and/or market requirements.

With both hybrid lines AC 151Y and AC 188W, female parent lines were constructed using the mutant sh2-i gene not in combination with the su1 and/or se1 genes. The hybrid AC 151Y line, however, was developed using a triple recessive male parent line, whereas the hybrid AC 188W line was developed using a double recessive male parent line.

The hybrid line AC 151Y (an sh2-i conversion inbred including the mutant sh2-i gene in its genome) is an sh2-i gene isogenic conversion of, and comparison to, an Abbott and Cobb, Inc. hybrid designated as ACR 5132Y (not including the mutant sh2-i gene in its genome). The only significant genetic difference between these two hybrid lines in this example is the presence of the mutant sh2-i gene in hybrid line AC 151Y and the absence of the sh2-i gene in hybrid line ACR 5132Y.

The hybrid line AC 188W (including the mutant sh2-i gene in its genome) is an sh2-i gene isogenic conversion of, and comparison to, an Abbott and Cobb, Inc. hybrid designated as ACR 5147W (not including the mutant sh2-i gene in its genome). Again, the only significant genetic difference between these two hybrid lines in this example is the presence of the mutant sh2-i gene in hybrid line AC 188W and the absence of the sh2-i gene in hybrid line ACR 5147W.

Laboratory Warm and Cold Germination Testing and Organoleptic Taste and Pericarp Tenderness Testing Table 4 below provides data resulting from actual comparisons of laboratory warm and cold germination data, as well as organoleptic taste and pericarp tenderness tests, for the sweet corns AC 151Y, ACR 5132Y, AC 188W and ACR 5147W. Germination scores are means of three replications of 100 kernels each. Laboratory scores not followed by the same number are significantly different at the 0.05 probability level via the Duncan's New Multiple Range Test. The organoleptic tests regarding sweetness (sugar content) and pericarp tenderness are described previously herein.

Table 4 shows that, in both cases in which the sh2-i mutant gene was added to the sweet corn genomes (hybrids AC 151Y and AC 188W), the isogenic hybrid comparison warm and cold laboratory scores were elevated, which is indicative of enhanced field emergence and vigor. However, Table 4 also shows that these two sweet corn varieties including the mutant sh2-i gene did not retain their sweetness longer (having scores of 2 and 3 on Day 7 in the seven day period immediately following the prime eating stage) in comparison with the two sweet corn varieties that did not include this gene (hybrids ACR 5132Y and ACR 5147W) (having scores of 5 and 7 on Day 7), and had pericarps that did not retain their tenderness longer (having scores of 1 and 2 on Day 7 in the seven day period immediately following the prime eating stage) in comparison with the two sweet corn varieties that did not include this gene (having scores of 3 and 2 on Day 7). The sweetness and pericarp tenderness scores that are present in Table 4 suggest that an insertion into inbred lines of the mutant sh2-i gene without a sequential layering against a genetic background of se1se1 and su1su1, as has been described previously herein, results in less efficacious and some detrimental effects in connection with overall eating quality (sweetness and pericarp tenderness).

In view of the above, it is considered to be very desirable (or, in some cases, as may readily be determined by those having ordinary skill in the art, even necessary) to assemble and direct the construction of mutant sh2-i gene materials in the manner that has been described previously herein in order to obtain maximum benefits desired by plant growers and consumers (i.e., using molecular markers and an se1se1 and su1su1 genetic background).

Example 5

Comparison of Various Physical Characteristics of Sweet Corn Hybrids ACX SS 7501Y, ACX SS 7078Y and ACX SS 7403RY sh2-i Female Parents in Combination with Male Parents having Triple Recessive Allelic Combinations In the experiments that are described in this example, the physical characteristics of sweet corn hybrids ACX SS 7501Y, ACX SS 7078Y and ACX SS 7403RY, all of which include the mutant sh2-i gene in their genomes, and very advantageously have the numerous and varied beneficial benefits that are described herein, were examined and compared using methods that are well known by those having ordinary skill in the art. Most of the examinations and comparisons were conducted using conventional maize visual observation, counting and measurement techniques, all of which are known by those having ordinary skill in the art. The results of these examinations and comparisons are set forth in Table 5 below. In each column in Table 5, the data for sweet corn hybrid ACX SS 7501Y is followed by the data for sweet corn hybrid ACX SS 7078Y, which is followed by the data for sweet corn hybrid ACX SS 7403RY. In Table 5, the term "Maturity" refers to the number of days that elapsed from the time that the hybrid was planted until it matured. The disease resistance ratings were performed by Dr. Jerald Pataky at the University of Illinois (Urbana-Champaign, Ill.) using well-known methods in an independently and controlled plant pathological environment.

TABLE 4

Isogenic Comparisons of Sweet Corn Varieties Including, or not Including, the sh2-i Gene

| Hybrid | Warm Germination | Cold Germination | Organoleptic Sweetness Score | | | Organoleptic Pericarp Tenderness Score | | |
|---|---|---|---|---|---|---|---|---|
| | | | Day 1 | Day 4 | Day 7 | Day 1 | Day 4 | Day 7 |
| AC 151Y (Contains sh2-i Gene) | 99a | 90a | 8 | 5 | 2 | 7 | 3 | 1 |
| ACR 5132Y (Does not Contain sh2-i Gene) | 98a | 82b | 8 | 6 | 5 | 8 | 5 | 3 |
| AC 188W (Contains sh2-i Gene) | 96a | 88b | 9 | 4 | 3 | 6 | 4 | 2 |
| ACR 5147W (Does not Contain sh2-i Gene) | 88b | 47c | 10 | 8 | 7 | 9 | 4 | 2 |

TABLE 5

Comparative Data for Three Sweet Corn Hybrids Including the Mutant Sh2-i Gene

| HYBRID | MATURITY | ROW COUNT | EAR LENGTH | EAR SHAPE |
|---|---|---|---|---|
| ACX SS 7501Y | 76 days | 16 | 8.0" | Cylindrical |
| ACX SS 7078Y | 78 days | 16-18 | 8.25" | Cylindrical |
| ACX SS 7403RY | 75 days | 16-18 | 8.25" | Cylindrical |

| EAR PACKAGE | KERNEL COLOR | PLANT SIZE | DISEASE RESISTANCE |
|---|---|---|---|
| Excellent flags, husk color | Yellow | Medium | Intermediate resistance to northern corn leaf blight and common rust |
| Very good husk color and length | Yellow | Medium/Tall | None claimed |
| Dark green husk and flags | Yellow | Medium | Intermediate resistance to northern corn leaf blight, resistance to multiple races of common rust |

Deposits

Deposits made with the American Type Culture Collection (ATCC) in Connection with Examples 1-5

The seed deposits discussed below, which relate to Examples 1-5, have been made with the American Type Culture Collection (ATCC) (Manassas, Va., USA) by Applicant Bryant J. Long on behalf of assignee Abbott & Cobb, Inc. (Wellington, Fla.) for the *Zea mays*, sweet corn hybrids identified below having desired triple allelic combinations, which each include the sh2-i gene in their genomes, and the corresponding *Zea mays*, sweet corn parent lines that were employed to develop these sweet corn hybrids. In the tables shown below, in connection with the sugary (su1), sugary enhancer-1 (se1) and shrunken-2 (sh2) genes, the designation "D" indicates that the male parent line included a double recessive allelic combination of these three genes, and the designation "T" indicates that the male parent line included a triple recessive allelic combination of these three genes.

| Hybrid | Parent Lines | Example No. | Deposit Made | Allelic Combination |
|---|---|---|---|---|
| ACX SS 7501Y | AC 199Y (Female) × AC 195Y (Male) | 2 | Yes* | T |
| ACX SS 7078Y | AC 199Y (Female) × AC 128Y (Male) | 3 | Yes* | T |
| ACX SS 7403RY | AC 199Y (Female) × AC 215Y (Male) | 3 | Yes* | T |
| AC 151Y | AC 103Y (Female) × AC 107Y (Male) | 4 | No | T |
| AC 188W | AC 106W (Female) × AC 163W (Male) | 4 | No | D |

*All three lines (the two parents and the hybrid identified) have been deposited.

| Identification Reference Used by Depositor/Inventor | ATCC Patent Deposit Designation | Quantity Received |
|---|---|---|
| (1) Sweet Corn, *Zea mays*: ACX SS 7501Y | PTA-10507 | 100 packets/25 seeds in each packet |
| (2) Sweet Corn, *Zea mays*: ACX SS 7078Y | PTA-10506 | 100 packets/25 seeds in each packet |
| (3) Sweet Corn, *Zea mays*: ACX SS 7403RY | PTA-10508 | 100 packets/25 seeds in each packet |
| (4) Sweet Corn, *Zea mays*: AC 128Y | PTA-10981 | 100 packets/25 seeds in each packet |
| (5) Sweet Corn, *Zea mays*: AC 195Y | PTA-10982 | 100 packets/25 seeds in each packet |
| (6) Sweet Corn, *Zea mays*: AC 199Y | PTA-10983 | 100 packets/25 seeds in each packet |
| (7) Sweet Corn, *Zea mays*: AC 215Y | PTA-10984 | 100 packets/25 seeds in each packet |

Hybrid Lines

Seeds of sweet corn, *Zea mays*, hybrids ACX SS 7501Y, ACX SS 7078Y and ACX SS 7403RY (100 packets for each of these three hybrids, with 25 seeds in each packet) were deposited on behalf of Abbott & Cobb, Inc. with the American Type Culture Collection (ATCC) (10801 University Boulevard, Manassas, Va., 20110-2209, United States of America) under The Budapest Treaty on the International Recognition of the Deposit of Microorganisms on Nov. 30, 2009, and were given ATCC Patent Deposit Designations PTA-10507, PTA-10506 and PTA-10508, respectively, by the ATCC. The deposited seeds were tested on Dec. 14, 2009 by the ATCC and, on that date, they were viable. The depositor was Abbott & Cobb, Inc., 11460 Fortune Circle, Wellington, Fla., 33414, United States of America.

Parent Lines

Seeds of the sweet corn, Zea mays, female and male parent lines that were employed to develop sweet corn, Zea mays, hybrid ACX SS 7501Y (100 packets, with 25 seeds in each packet), designated AC 199Y (female) and AC 195Y (male), were deposited on behalf of Abbott & Cobb, Inc. with the American Type Culture Collection (ATCC) (10801 University Boulevard, Manassas, Va., 20110-2209, USA) under The Budapest Treaty on the International Recognition of the Deposit of Microorganisms on May 19, 2010, and were given ATCC Patent Deposit Designations PTA-10983 and PTA-10982 by the ATCC, respectively. The deposited seeds were tested on Jun. 1, 2010 by the ATCC and, on that date, they were viable.

Seeds of the sweet corn, Zea mays, female and male parent lines that were employed to develop sweet corn, Zea mays, hybrid ACX SS 7078Y (100 packets, with 25 seeds in each packet), designated AC 199Y (female) and AC 128Y (male), were deposited on behalf of Abbott & Cobb, Inc. with the American Type Culture Collection (ATCC) (10801 University Boulevard, Manassas, Va., 20110-2209, USA) under The Budapest Treaty on the International Recognition of the Deposit of Microorganisms on May 19, 2010, and were given ATCC Patent Deposit Designations PTA-10983 and PTA-10981, respectively, by the ATCC. The deposited seeds were tested on Jun. 1, 2010 by the ATCC and, on that date, they were viable.

Seeds of the sweet corn, Zea mays, female and male parent lines that were employed to develop sweet corn, Zea mays, hybrid ACX SS 7403RY (100 packets, with 25 seeds in each packet), designated AC 199Y (female) and AC 215Y (male), were deposited on behalf of Abbott & Cobb, Inc. with the American Type Culture Collection (ATCC) (10801 University Boulevard, Manassas, Va., 20110-2209, USA) under The Budapest Treaty on the International Recognition of the Deposit of Microorganisms on May 19, 2010, and were given ATCC Patent Deposit Designations PTA-10983 and PTA-10984, respectively, by the ATCC. The deposited seeds were tested on Jun. 1, 2010 by the ATCC and, on that date, they were viable.

Certificates of Deposit have been received from the American Type Culture Collection (ATCC) for each of the deposits that are described above.

Example 6

Construction and Testing of Sweet Corn Parental Inbred Line AC 157Y and Parental Near Isogenic Line (NIL) AC 157Y-i sh2-i Female Parents in Combination with Male Parents not having Double or Triple Recessive Allelic Combinations In the experiments that are described in this example, in order to attempt to solve the problem of manipulating the regulation of carbohydrate accumulation, and pericarp tenderness, in sweet corn varieties containing the mutant sh2-i gene, appropriate parental near isogenic lines (NILs) were constructed and tested, using methods that have previously been described herein or that are described below and/or are known by those having ordinary skill in the art, of the following genotypic combinations:

Female Parent Lines (NILs)

AC 157Y: Su1Su1Se1Se1 sh2sh2
AC 157Y-i: Su1Su1 Se1Se1 sh2-i sh2-i

Construction of Parental NILs

The mutant sh2-i gene was incorporated into selected inbred parent lines having the above gene combinations. Such parent inbreds were also selected on the basis of desirable horticultural and seed production criteria, including those that are discussed herein. It was discovered through a significant amount of organoleptic experimentation and testing that unacceptable starch synthesis and starch buildup occurred immediately following the peak eating stage with some sweet corn hybrids produced using the sh2-i conversion inbreds described above, particularly those hybrids produced using two sh2-i conversion inbred parent lines (i.e., two parental lines that both include a mutant sh2-i gene in their genomes), thus disallowing an assembly of hybrids using two sh2-i parent lines. Through this organoleptic experimentation and testing, it was eventually determined that a potentially desirable genotype to use for female sweet corn parent lines was Su1Su1Se1Se1 sh2-i sh2-i, and that the utilization of male parent lines having one set of homozygous recessive mutant alleles (Su1Su1 Se1Se1 sh2sh2) could prove beneficial. The corresponding hybrid genotype is of the following composition:

| Su1Su1 Se1Se1 sh2-i sh2-i | X | Su1Su1Se1Se1sh2sh2 |
|---|---|---|
| (Female Parent Line) | | (Male Parent Line) |
| (sh2-i conversion inbred) | | (inbred not including an sh2-i gene) |

Female Parent Line

In view of the above and below, the inventor decided to use the sh2-i conversion inbred sweet corn lines only as the female parents (i.e., not as the male parents) in commercial maize production. This decision was based upon a number of factors, including those discussed above and previously herein. One such factor for using the sh2-i conversion inbred parents as females was based upon the fact that kernel pericarp and resulting seed coat is 2N and maternally inherited. Utilization of the sh2-i conversion inbreds as female parents, thus, preserves the very advantageous enhanced germination and seedling vigor characteristic provided by the sh2-i gene, and expressed as a function of the female parental line. In addition, commercial seed production yields appear to be greatly enhanced as an artifact of the superior germination and seedling vigor traits provided to sweet corn hybrids by the sh2-i female seed parental lines. Sh2-i conversion inbred female parent sweet corn lines were determined to provide hybrids developed therewith the multiple beneficial traits of having an enhanced germination, an enhanced seedling vigor and an enhanced commercial seed production yield.

Backcrossing of various commercial inbred lines was initiated using the donor sh2-i gene source provided by Dr. C. L. Hanna of the University of Florida (Gainesville, Fla.). This donor source was test crossed to appropriate genetic lines to determine the status of the su1 and se1 genes. Test crossing results confirmed that the donor sh2-i gene source had a genotype of Su1Su1Se1Se1 relative to the sugary-1 (su1) and sugary enhancer-1 (se1) genes.

Ears of corn from BC1-S1 populations were phenotypically examined. (BC1-S1 is an Abbott and Cobb, Inc. breeding population, and the term "BC1-S1" is a genetic or plant breeder's word for point in time relating to the progress of the final product. The final product in this example is a reconstruction of the recurrent parent in which the sh2-i mutant allele is to be added.) Only kernels expressing a hard seed coat characteristic of flint or dent corns were saved and utilized in further backcrossing cycles. A minimum of five backcross cycles involving recurrent parents were performed to insure adequate reconstitution of commercial sweet corn lines incorporating the mutant sh2-i gene therein. The resultant kernel phenotype was predominantly similar to that of the sh2-i appearance, being smooth, full and relatively heavy. (The mutant sh2sh2 morphological sweet corn kernel appearance is distinct from other varieties of sweet corn in that dry seeds (kernels) appear to be translucent, highly collapsed, and wrinkled. The mutant sh2-i sweet corn kernel phenotypes, in contrast, are smooth, heavier, well filled and nearly like that of flint field corn in appearance (having round kernels with smooth coats)). Kernel phenotypes were confirmed with molecular markers, as is discussed elsewhere herein, and as is shown in FIG. 10.

Laboratory warm and cold soil germination testings were conducted on the sh2-i conversion lines to verify enhanced seedling performances associated with the donor sh2-i source. Actual cold field soil testing was conducted for further verification of enhanced germination and seedling vigor. Organoleptic taste testing of the resulting Su1Su1 sh2-i sh2-i conversion lines and the recurrent comparison Su1Su1 sh2sh2 lines were conducted for verification of sugar, pericarp and holding ability.

One sh2-i conversion female parent line of particular interest was designated as AC 157Y-i. The Characteristics Table (Parental Sweet Corn lines) set forth hereinabove prior to Example 1 describes the characteristics in detail of this particular parent sweet corn line.

Germination and Seedling Vigor Testing of Female Parent Lines

Table 6 and Table 7 below show comparative laboratory warm and cold germination values, and field soil germination and seedling vigor data, respectively for: (i) a commercial "supersweet" (Su1Su1 sh2sh2) inbred parent line designated AC 157Y (not including the sh2-i gene in its genome); and (ii) the NIL female (Su1Su1 sh2-i sh2-i) inbred parent line (an sh2-i conversion inbred) designated AC 157Y-i (including the sh2-i gene in its genome). These parent lines are the same, with the exception that one does not include the sh2-i gene in its genome, and the other includes the sh2-i gene in its genome. These tests were performed in the same manner as is previously described elsewhere. Means not followed by the same letter are significantly different at the 0.05 probability level via the Duncan's Multiple Range Statistical Test.

Both the very significant advantage of the laboratory cold germination data (Table 6), as well as the very desirable phenotypic seed morphological distinctiveness, of female sh2-i conversion inbred parent line AC 157Y-i in comparison with inbred parent line AC 157Y is clearly apparent from this data. Further, the AC 157Y-i conversion inbred parent line very desirably exhibits a smooth hard seed coat as compared with the very undesirable shrunken, collapsed appearance of the seed of the conventional inbred parent line AC 157Y. Moreover, the data for field soil germination and seedling vigor performance (Table 7) show a significantly enhanced, and much more desirable, field soil germination and seedling vigor for the AC 157Y-i parent sh2-i conversion inbred line in comparison with the AC 157Y parent inbred line.

TABLE 6

| Inbred Parent Line | Warm Germination (Percentage)* | Cold Germination (Percentage)* |
|---|---|---|
| AC 157Y (not including an sh2-i gene) | 94a | 71a |
| AC 157Y-i (including an sh2-i gene) (Female Parent Line) | 98a | 94b |

*The scores represent the mean of three replications of 100 kernels each.

TABLE 7

| Inbred Parent Line | Field Soil Germination Percentage* | Seedling Vigor** |
|---|---|---|
| AC 157Y (not including an sh2-i gene) | 86a | 3a |
| AC 157Y-i (including an sh2-i gene) (Female Parent Line) | 97b | 5b |

*The scores represent the mean of three replications of 100 kernels each. Soil temperatures averaged approximately 50° F.
**Seedling vigor was rated on a scale of 1-5, with 5 representing excellent seedling vigor and 1 representing poor seedling vigor.

Male Parent Line

In view of the above, the genotype of the male parental lines selected for use in hybrid combinations with the sh2-i conversion female lines was chosen based upon its ability to provide desirable horticultural qualities to sweet corn hybrids produced using such lines. Thus, male parental line genotypes were utilized that included more conventional "supersweet" genetics of the composition Su1Su1Se1Se1 sh2sh2. The male sweet corn lines of this class that are set forth in this example are typically inbred materials that are commercially available from Abbott and Cobb, Inc. (see Example 7). These male parental genotypes have but one set of homozygous recessive mutant alleles. The sweetness and tenderness of kernels of such male parental lines are generally significantly less in comparison with the sweetness and tenderness of male parental sweet corn lines including a genetic composition containing two or three homozygous recessive mutant genes, such as Su1Su1 se1 se1 sh2sh2 or su1su1se1se1 sh2sh2, respectively. With respect to possible different desirable sweet corn traits, such as an enhanced vigor, this male parent line genotype was chosen as a result of its ability to provide hybrids developed therefrom with: (i) desirable horticultural plant and ear characteristics; and (ii) high yielding capabilities.

Organoleptic Testing of Female Parent Lines (Sweetness and Pericarp Tenderness)

Figure 11:
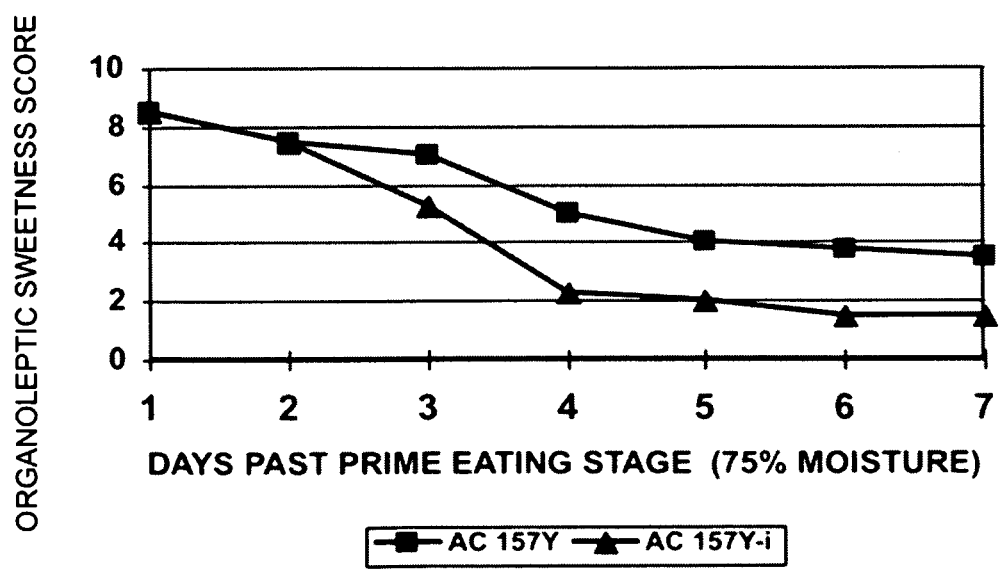
FIG. 11 is a line graph that shows organoleptic average sugar (sweetness) scores for the sweet corn inbred parent lines AC 157Y (not including an sh2-i gene) and AC 157Y-i (an sh2-i conversion inbred including an sh2-i gene) in the seven day period immediately following the prime eating stage (at a level of approximately 75% moisture). It illustrates the comparative organoleptic sugar levels among these two sweet corn inbred parent lines over this seven-day period of time.

FIG. 11 is a line graph that illustrates comparative organoleptic average sugar (sweetness) scores for the sweet corn inbred parent line AC 157Y (not including the sh2-i gene in its genome) and the NIL female inbred parent line (sh2-i conversion inbred) designated AC 157Y-i (including the sh2-i gene in its genome) in the seven day period immediately following the prime eating stage (at a level of approximately 75% moisture). FIG. 11 illustrates the comparative organoleptic sugar levels among these two sweet corn inbred parent lines over this seven day period of time. The organoleptic sweetness scores ranged from 1 (very little sweetness with a considerable starch taste) to 10 (sweet with little or no starch taste). FIG. 11 shows that, on days 1 and 2 past the prime eating stage, female parent line AC 157Y sh2-i had comparatively high organoleptic sweetness scores (about 8.5 on day 1 and about 7.5 on day 2), which were the same scores shown by parent line AC 157Y. The organoleptic sweetness score for female parent line AC 157Y-i on day 3 was somewhat higher than 5, and on days 4 and 5 was about 2, and on days 6 and 7 was about 1.5. The organoleptic sweetness score for parent line AC 157Y on day 3 was about 7, on day 4 was about 5, on days 5 and 6 was about 4, and on day 7 was somewhat higher than 3.

Figure 12:
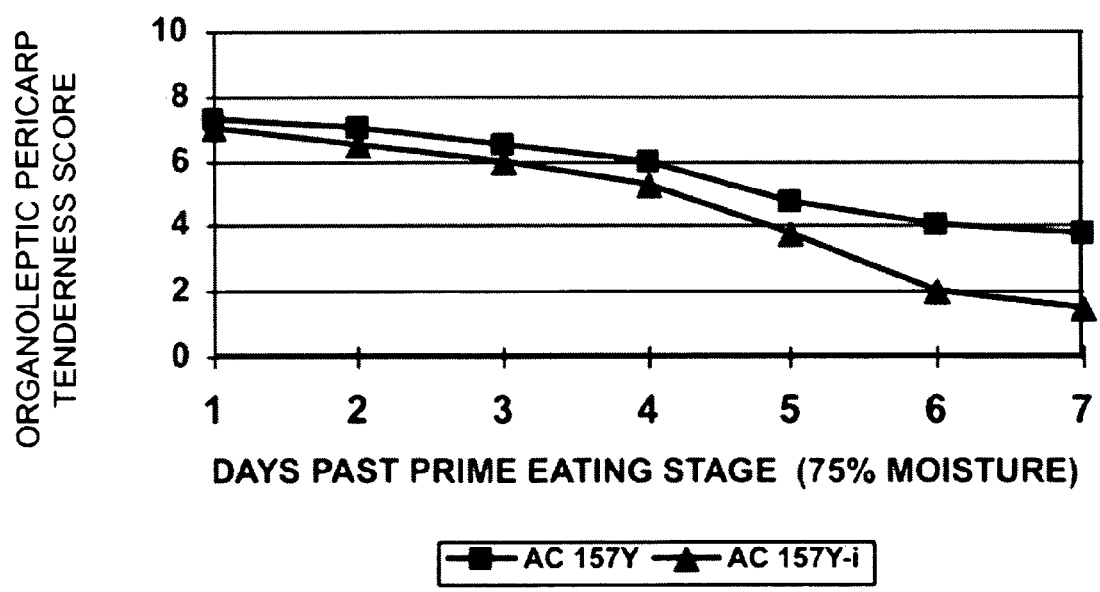
FIG. 12 is a line graph that shows organoleptic average pericarp tenderness scores for the sweet corn inbred parent lines AC 157Y (not including an sh2-i gene) and AC 157Y-i (an sh2-i conversion inbred including an sh2-i gene) in the seven day period immediately following the prime eating stage (at a level of approximately 75% moisture). It illustrates the comparative organoleptic pericarp tenderness levels among these two sweet corn inbred parent lines over this seven-day period of time.

FIG. 12 is a line graph that shows the comparative organoleptic pericarp tenderness scores for the same sweet corn inbred parent lines in the seven day period immediately following the prime eating stage (at a level of approximately 75% moisture). The organoleptic tenderness scores ranged from 1 (very tough pericarp) to 10 (very tender pericarp). FIG. 12 shows that the AC 157Y-i female parent sweet corn line maintained an organoleptic pericarp tenderness score from about 6 to about 7 in days 1, 2 and 3 past the prime eating stage, and scores of about 5 on day 4, about 4 on day 5, about 2 on day 6, and about 1.5 on day 7. Similar scores were shown for parent line AC 157Y on days 1, 2 and 3 past the prime eating stage. The AC 157Y-i parent sweet corn line was of comparative initial tenderness to the AC 157Y sweet corn parent line, but with a noticeable decline over time.

Example 7

Production using Molecular Markers and Testing of Sweet Corn Near Isogenic Line (NIL) Hybrid ACX SS 1082Y and Hybrid ACX SS 1082Y sh2-i Specific Allelic Combinations In the experiments that are described in this example, sweet corn hybrid NILs having specific allelic combinations were developed utilizing the sh2-i gene and molecular markers, and then tested in the manner described below.

Construction of Hybrid ACX SS 1082Y sh2-i

Sweet corn hybrids having specific allelic combinations were assembled according to the same breeding procedures that are previously described herein. One resulting sh2-i sweet corn hybrid NIL (an sh2-i conversion inbred) of particular interest was designated as ACX SS 1082Y sh2-i., and was developed using the AC 157Y-i female parental sweet corn NIL line that is discussed in Example 6 along with the male parental line AC 144Y (an inbred line that is commercially available from Abbott and Cobb, Inc.), both of which are also identified below.

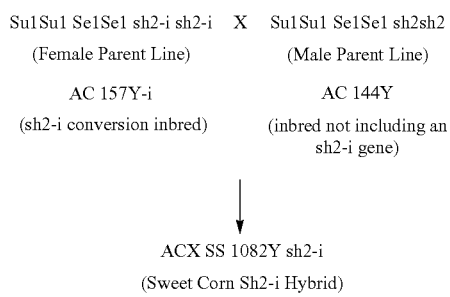

Germination and Seedling Vigor Testing

Table 8 and Table 9 below show comparative laboratory warm and cold germination values, and field soil germination and seedling vigor data, respectively for: (i) a sweet corn hybrid NIL designated ACX 1082Y (not including the sh2-i gene in its genome); and (ii) the sweet corn hybrid NIL designated ACX SS 1082Y sh2-i (an sh2-i conversion inbred including the sh2-i gene in its genome). These hybrids are the same, with the exception that one does not include the sh2-i gene in its genome, and the other includes the sh2-i gene in its genome. These tests were performed in the same manner as has previously been described herein. Means not followed by the same letter are significantly different at the 0.05 probability level via the Duncan's Multiple Range Statistical Test.

Both the very significant advantage of the laboratory cold germination data (Table 8), as well as the very desirable phenotypic seed morphological distinctiveness, of sweet corn hybrid ACX SS 1082Y sh2-i (including the sh2-i gene in its genome) in comparison with sweet corn hybrid ACX 1082Y (not including the sh2-i gene in its genome) is clearly apparent from this data. Further, sweet corn hybrid ACX SS 1082Y sh2-i very desirably exhibits a smooth hard seed coat as compared with the very undesirable shrunken, collapsed appearance of the seed of sweet corn hybrid ACX 1082Y. Moreover, the data for field soil germination and seedling vigor performance (Table 9) show a significantly enhanced, and much more desirable, field soil germination and seedling vigor for sweet corn hybrid ACX SS 1082Y sh2-i in comparison with sweet corn hybrid ACX 1082Y.

TABLE 8

| Hybrid | Warm Germination (Percentage)* | Cold Germination (Percentage)* |
|---|---|---|
| ACX 1082Y (NIL not including an sh2-i gene) | 93a | 77a |
| ACX SS 1082Y sh2-i (NIL including an sh2-i gene) | 99a | 96b |

*The scores represent the mean of three replications of 100 kernels each.

TABLE 9

| Hybrid | Field Soil Germination (Percentage)* | Seedling Vigor |
|---|---|---|
| ACX 1082Y (NIL not including an sh2-i gene) | 90a | 3a |
| ACX SS 1082Y sh2-i (NIL including an sh2-i gene) | 97b | 5b |

*The scores represent the mean of three replications of 100 kernels each. Soil temperatures averaged approximately 50° F.
**Seedling vigor was rated on a scale of 1-5, with 5 representing excellent seedling vigor and 1 representing poor seedling vigor.

Organoleptic Testing (Sweetness and Pericarp Tenderness)

Figure 13:
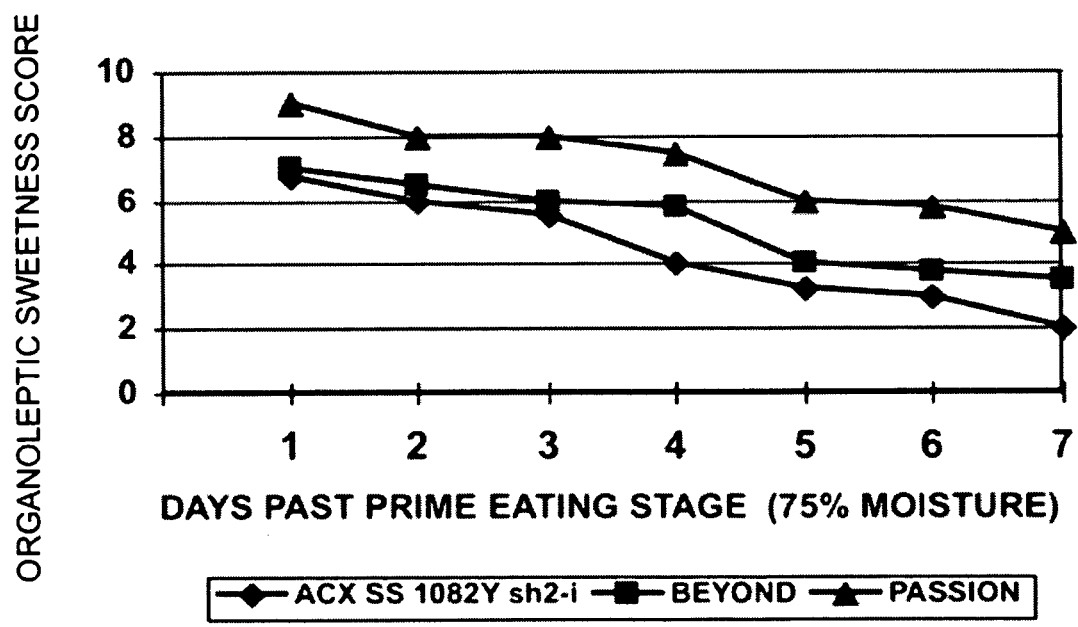
FIG. 13 is a line graph that shows organoleptic average sugar (sweetness) scores for the sweet corn varieties Beyond (not including the sh2-i gene), Passion (not including the sh2-i gene) and hybrid ACX SS 1082Y sh2-i (an sh2-i conversion inbred including the sh2-i gene) in the seven day period immediately following the prime eating stage (at a level of approximately 75% moisture). It illustrates the comparative organoleptic sugar levels among these three sweet corn varieties over this seven-day period of time.

FIG. 13 is a line graph that shows organoleptic average sugar (sweetness) scores for the sweet corn varieties Beyond (not including the sh2-i gene), Passion (not including the sh2-i gene) and hybrid ACX SS 1082Y sh2-i (an sh2-i conversion inbred including the sh2-i gene) in the seven day period immediately following the prime eating stage (at a level of approximately 75% moisture). It illustrates the comparative organoleptic sugar levels among these three sweet corn varieties over this seven-day period of time. The organoleptic sweetness scores ranged from 1 (very little sweetness with a considerable starch taste) to 10 (sweet with little or no starch taste). The commercial variety Passion is sold and distributed through Monsanto (St. Louis, Mo.), and the commercial variety Beyond is sold and distributed by Abbott and Cobb, Inc. (Trevose, Pa.), and has served as a standard, primarily in the Southeast commercial shipping markets. FIG. 13 shows that, in this comparison, the variety Passion remained very sweet through the first four days following the prime eating stage, and then tapered off in days 5, 6 and 7. The variety Beyond was not considered as sweet initially as the variety Passion, but followed a general pattern of sugar retention through the first four days after the prime eating stage, and then also tapered off through days 5, 6 and 7. Sweet corn hybrid ACX SS 1082Y sh2-i was similar in sweetness to the Beyond variety in days 1, 2 and 3 following the prime eating stage (having a score of about 7, 6 and 5.5 on these days, respectively), and then tapered off in days 4, 5, 6 and 7 (to scores of about 4, 3, 2 and 2, respectively). The initiation of a somewhat starchy taste was detected in sweet corn hybrid ACX SS 1082Y sh2-i starting on day 3.

Figure 14:
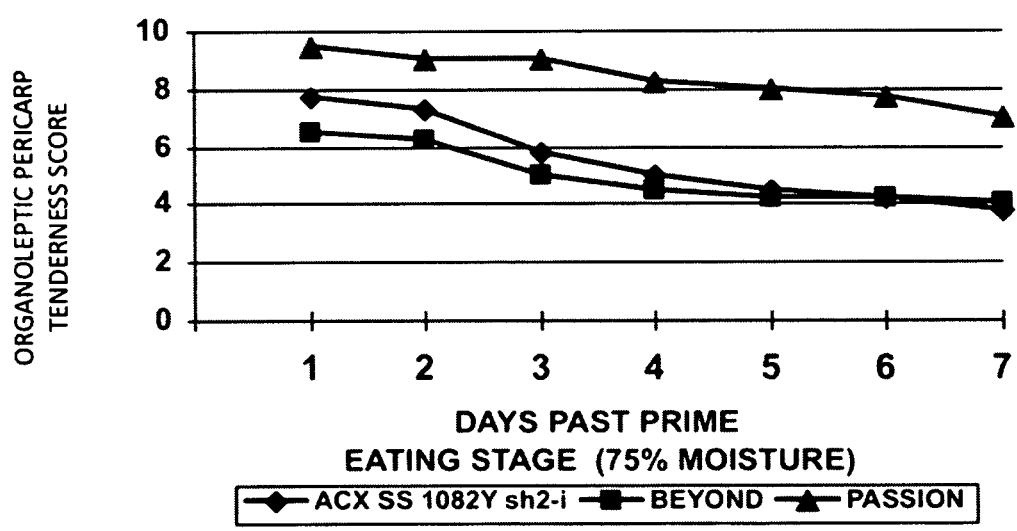
FIG. 14 is a line graph that shows organoleptic average pericarp tenderness scores for the sweet corn varieties Beyond (not including the sh2-i gene), Passion (not including the sh2-i gene) and hybrid ACX SS 1082Y sh2-i (an sh2-i conversion inbred including the sh2-i gene) in the seven day period immediately following the prime eating stage (at a level of approximately 75% moisture). It illustrates the comparative organoleptic pericarp tenderness levels among these three sweet corn varieties over this seven-day period.

FIG. 14 is a line graph that shows organoleptic average pericarp tenderness scores for the same sweet corn varieties in the seven day period immediately following the prime eating stage (at a level of approximately 75% moisture). It illustrates the comparative organoleptic pericarp tenderness levels among these three sweet corn varieties over this seven day period. The organoleptic tenderness scores ranged from 1 (very tough pericarp) to 10 (very tender pericarp). FIG. 14 shows that the tenderness level of the Passion variety went from a score of about 9.5 on day 1 past the prime eating stage to a score of about 7 on day 7, with the tenderness level holding through the first four days, and then dropping moderately on days 5, 6 and 7. This variety was considered to be the most tender of the three comparison varieties. The variety Beyond had a tenderness score of about 6.5 on day 1 past the prime eating stage, and a score of about 6 on day 2, and then tapered off with scores of about 5 on day 3, about 4.5 on day 4, and about 4 on days 5, 6 and 7. Thus, this variety was moderately tender in days 1 and 2, and then became substantially less tender starting on day 3 and ending on day 7. The sweet corn hybrid ACX SS 1082Y sh2-i had tenderness scores of about 8 on day 1 following the prime eating stage, about 7 on day 2, about 6 on day 3, about 5 on day 4, and about 4 (or a little higher) on days 5, 6 and 7. Thus, this variety was quite tender on days 1 and 2, slightly less tender on days 3 and 4, and then moderately tender on days 5, 6 and 7.

These data indicate a very beneficial field emergence and vigor benefit to hybrids such as ACX SS 1082Y sh2-i. However, the construction of such hybrids as described in Examples 6 and 7 indicate that male parent lines containing but one set of mutant homozygous recessive alleles, for example Su1Su1Se1Se1 sh2sh2, results in a reduced level of overall sweetness and tenderness in the hybrid combination. The sweetness and pericarp tenderness scores that are presented also suggest that an insertion into female inbred lines of the mutant sh2-i gene without a sequential layering against a genetic background of se1se1 and su1su1, as has been described previously herein, results in less efficacious and some detrimental effects in connection with overall eating quality (sweetness and pericarp tenderness).

Example 8

Production without using Molecular Markers, and a se1se1/su1su1 Genetic Background, and Testing of Sweet Corn Hybrids ACR SS 4500Y and ACR SS 4501Y sh2-i Female Parents in Combination with Male Parents having Double or Triple Recessive Allelic Combinations In the experiments that are described in this example, additional sweet corn sh2-i hybrids were developed using double and triple recessive male parental genotypes.

Construction of Hybrids ACR SS 4500Y and ACR SS 4501Y

These additional sweet corn hybrids were assembled according to the same breeding procedures that are described in Examples 1, 2 and 3, with the exceptions that the hybrid lines containing the mutant sh2-i gene in their genomes were not assembled utilizing molecular markers, as previously described herein (Examples 1, 2 and 3), and did not incorporate se1se1/su1su1 alleles.

Two resulting sweet corn sh2-i hybrids of particular interest were designated ACR SS 4500Y and ACR SS 4501Y, and were developed using parental sweet corn inbreds not constructed with su1 and se1 backgrounds. These hybrids were developed from sh2-i female conversion parent lines not containing the su1 and se1 genes to test eating quality in comparison with sh2-i female parental inbreds constructed utilizing the incorporation of the su1 and se1 genes. It was also considered important to test the effect of using double and triple homozygous recessive male lines with the sh2-i conversion females lines that were not constructed utilizing sequential layering over the su1 and se1 genes.

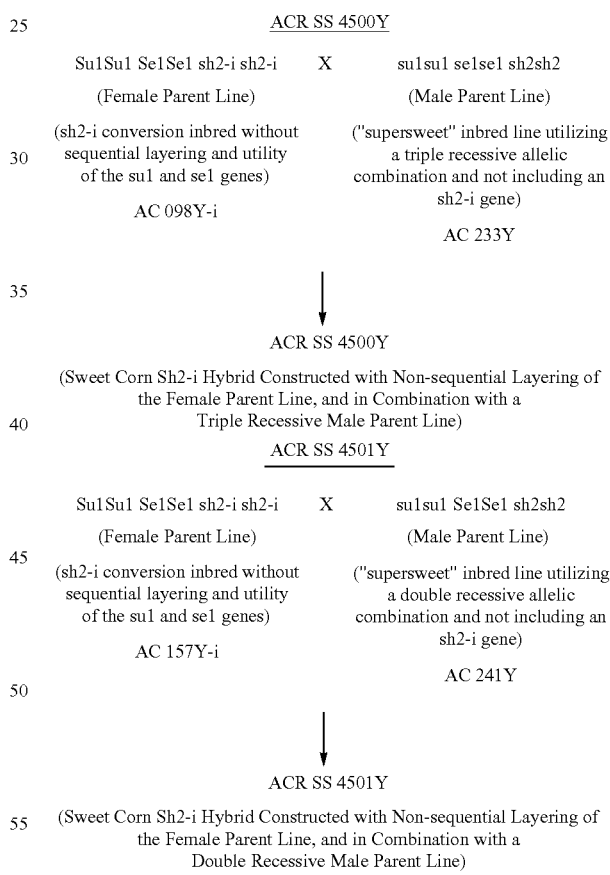

These hybrid lines differed in a beneficial manner from other hybrids prepared in this example in performance relative to geographical growing regions and/or market requirements, and their characteristics are described in detail in the Characteristics Table (Hybrid Sweet Corn lines) that is set forth hereinabove prior to Example 1. The Characteristics Table (Parental Sweet Corn lines) describes the characteristics in detail of the parent sweet corn lines that were employed to develop these hybrid lines.

With both hybrid lines ACR SS 4500Y and ACR SS 4501Y, female parent lines were constructed using the mutant sh2-i gene not in combination with the su1 and/or se1 genes. The hybrid ACR SS 4500Y line, however, was developed using a triple recessive male parent line, whereas the hybrid ACR SS 4501Y line was developed using a double recessive male parent line.

Parent female line AC 098Y-i (an sh2-i conversion inbred including the mutant sh2-i gene in its genome) is an sh2-i gene isogenic conversion of, and comparison to, a commercially available (from Abbott and Cobb, Inc.) parent female inbred line designated as AC 098Y (not including the mutant sh2-i gene in its genome). The only significant genetic difference between these two inbred female parent lines in this example is the presence of the mutant sh2-i gene in inbred female parent line AC 098Y-i and the absence of the sh2-i gene in inbred female parent line AC 098Y.

Parent female line AC 157Y-i (an sh2-i conversion inbred including the mutant sh2-i gene in its genome) is an sh2-i gene isogenic conversion of, and comparison to, an Abbott and Cobb, Inc. parent female line designated as AC 157Y (not including the mutant sh2-i gene in its genome). The only significant genetic difference between these two inbred female parent lines in this example is the presence of the mutant sh2-i gene in inbred female parent line AC 157Y-i and the absence of the sh2-i gene in inbred female parent line AC 157Y.

Laboratory Warm and Cold Germination Testing and Organoleptic Taste and Pericarp Tenderness Testing Table 10 below provides data resulting from actual comparisons of laboratory warm and cold germination data, as well as organoleptic taste and pericarp tenderness tests, for the sweet corn inbred female parent lines AC 098Y-i, AC 098Y, AC 157Y-i, and AC 157Y. Germination scores are means of three replications of 100 kernels each. Laboratory scores not followed by the same number are significantly different at the 0.05 probability level via the Duncan's New Multiple Range Test. The organoleptic tests regarding sweetness (sugar content) and pericarp tenderness are described previously herein.

Table 10 shows that, in both cases in which the sh2-i mutant gene was added to the sweet corn genomes (inbred female parent lines AC 098Y-i and AC 157Y-i), the isogenic inbred comparison warm and cold laboratory scores were significantly elevated in comparison with the inbred female parent lines not including the sh2-i mutant gene in their genomes (AC 098Y and AC 157Y), which is indicative of an enhanced field emergence and vigor. Table 10 also shows that these two sweet corn inbreds lines including the mutant sh2-i gene did not retain their sweetness quite as long (having scores of 2 and 2, respectively, on Day 7 in the seven day period immediately following the prime eating stage) as the two sweet corn inbred lines that did not include this gene in their genomes (inbred AC 098Y and AC 157Y) (having scores of 5 and 4 on Day 7), and had pericarps that did not retain their tenderness quite as long (having scores of 1 and 2, respectively, on Day 7 in the seven day period immediately following the prime eating stage) as the two sweet corn inbreds that did not include this gene in their genomes (having scores of 3 and 4, respectively, on Day 7). The sweetness and pericarp tenderness scores that are present in Table 10 suggest that an insertion into inbred lines of the mutant sh2-i gene without a sequential layering against a genetic background of se1se1 and su1su1, as has been described previously herein, results in less efficacious and some detrimental effects in connection with overall eating quality (sweetness and pericarp tenderness) in comparison with an insertion into the same inbred lines of the mutant sh2-i gene with a sequential layering against a genetic background of se1se1 and su1su1. They all, however, very advantageously exhibit an enhanced field emergence and vigor.

In view of the above, it is considered to be very desirable to assemble and direct the construction of mutant sh2-i gene materials in the manner that has been described previously herein in order to obtain maximum benefits desired by plant growers and consumers (i.e., using molecular markers and an se1se1 and su1su1 genetic background).

TABLE 10

Isogenic Comparisons of Sweet Corn Inbreds Including, or not Including, the sh2-i Gene

| Inbreds | Warm Germination | Cold Germination | Organoleptic Sweetness Score | | | Organoleptic Pericarp Tenderness Score | | |
|---|---|---|---|---|---|---|---|---|
| | | | Day 1 | Day 4 | Day 7 | Day 1 | Day 4 | Day 7 |
| AC 098Y-i (Contains sh2-i Gene) | 99a | 90a | 8 | 5 | 2 | 7 | 3 | 1 |
| AC 098Y (Does not Contain sh2-i Gene) | 98a | 82b | 8 | 6 | 5 | 8 | 5 | 3 |
| AC 157Y-i (Contains sh2-i Gene) | 98a | 94a | 8 | 2 | 2 | 7 | 5 | 2 |
| AC 157Y (Does not Contain sh2-i Gene) | 94a | 71c | 8 | 5 | 4 | 7 | 6 | 4 |

Additional Deposits

Deposits made with the American Type Culture Collection (ATCC) in Connection with Examples 6-8

The seed deposits discussed below, which relate to Examples 6-8, have been made with the American Type Culture Collection (ATCC) (Manassas, Va., USA) by Applicant Bryant J. Long on behalf of assignee Abbott & Cobb, Inc. (Wellington, Fla.) for the *Zea mays*, sweet corn hybrids identified below having desired specific allelic combinations, which each include the sh2-i gene in their genomes, and the corresponding *Zea mays*, sweet corn parent lines that were employed to develop these sweet corn hybrids. In the tables shown below, in connection with the sugary (su1), sugary enhancer-1 (se1) and shrunken-2 (sh2) genes, the designation "S" indicates that the male parent line included a single recessive allelic combination of these three genes, the designation "D" indicates that the male parent line included a double recessive allelic combination of these three genes, and the designation "T" indicates that the male parent line included a triple recessive allelic combination of these three genes.

| Hybrid | Parent Lines | Example No. | Deposit Made | Allelic Combination |
|---|---|---|---|---|
| ACX SS 1082Y sh2-i | AC 157Y-i (Female) × AC 144Y (Male) | 7 | Yes* | S |
| ACR SS 4500Y | AC 098Y-i (Female) × AC 233Y (Male) | 8 | Yes* | T |
| ACR SS 4501Y | AC 157Y-i (Female) × AC 241Y (Male) | 8 | Yes* | D |

*All three lines (two parents and hybrid) have been deposited.

| Identification Reference Used by Depositor/Inventor | ATCC Patent Deposit Designation | Quantity Received |
|---|---|---|
| (1) Sweet Corn, Zea mays: ACX SS 1082Y sh2-i | PTA-11467 | 100 packets/25 seeds in each packet |
| (2) Sweet Corn, Zea mays: AC 157Y-i | PTA-11470 | 100 packets/25 seeds in each packet |
| (3) Sweet Corn, Zea mays: AC 144Y | PTA-11469 | 100 packets/25 seeds in each packet |
| (4) Sweet Corn, Zea mays: ACR SS 4500Y | PTA-11472 | 100 packets/25 seeds in each packet |
| (5) Sweet Corn, Zea mays: AC 098Y-i | PTA-11471 | 100 packets/25 seeds in each packet |
| (6) Sweet Corn, Zea mays: AC 233Y | PTA-11465 | 100 packets/25 seeds in each packet |
| (7) Sweet Corn, Zea mays: ACR SS 4501Y | PTA-11468 | 100 packets/25 seeds in each packet |
| (8) Sweet Corn, Zea mays: AC 241Y | PTA-11466 | 100 packets/25 seeds in each packet |

Hybrid Lines

Seeds of sweet corn, Zea mays, hybrids ACX SS 1082Y sh2-i, ACR SS 4500Y and ACR SS 4501Y (100 packets for each of these three hybrids, with 25 seeds in each packet) were deposited on behalf of Abbott & Cobb; Inc. with the American Type Culture Collection (ATCC) (10801 University Boulevard, Manassas, Va., 20110-2209, United States of America) under The Budapest Treaty on the International Recognition of the Deposit of Microorganisms on Nov. 11, 2010, and were given ATCC Patent Deposit Designations PTA-11467, PTA-11472 and PTA-11468, respectively, by the ATCC. The deposited seeds were tested on Nov. 22, 2010 by the ATCC and, on that date, they were viable. The depositor waste Abbott & Cobb, Inc., 11460 Fortune Circle, Wellington, Fla., 33414, United States of America.

Parent Lines

Seeds of the sweet corn, Zea mays, female and male parent lines that were employed to develop sweet corn, Zea mays, hybrid ACX SS 1082Y sh2-i (100 packets, with 25 seeds in each packet), designated AC 157Y-i (female) and AC 144Y (male), were deposited on behalf of Abbott & Cobb, Inc. with the American Type Culture Collection (ATCC) (10801 University Boulevard, Manassas, Va., 20110-2209, USA) under The Budapest Treaty on the International Recognition of the Deposit of Microorganisms on Nov. 11, 2010, and were given ATCC Patent Deposit Designations PTA-11470 and PTA-11469 by the ATCC, respectively. The deposited seeds were tested on Nov. 22, 2010 by the ATCC and, on that date, they were viable.

Seeds of the sweet corn, Zea mays, female and male parent lines that were employed to develop sweet corn, Zea mays, hybrid ACR SS 4500Y (100 packets, with 25 seeds in each packet), designated AC 098Y-i (female) and AC 233Y (male), were deposited on behalf of Abbott & Cobb, Inc. with the American Type Culture Collection (ATCC) (10801 University. Boulevard, Manassas, Va., 20110-2209, USA) under The Budapest Treaty on the International Recognition of the Deposit of Microorganisms on Nov. 11, 2010, and were given ATCC Patent Deposit Designations PTA-11471 and PTA-11465 by the ATCC, respectively. The deposited seeds were tested on Nov. 22, 2010 by the ATCC and, on that date, they were/are viable.

Seeds of the sweet corn, Zea mays, female and male parent lines that were employed to develop sweet corn, Zea mays, hybrid ACR SS 4501Y (100 packets, with 25 seeds in each packet), designated AC 157Y-i (female) and AC 241Y (male), were deposited on behalf of Abbott & Cobb, Inc. with the American Type Culture Collection (ATCC) (10801 University Boulevard, Manassas, Va., 20110-2209, USA) under The Budapest Treaty on the International Recognition of the Deposit of Microorganisms on Nov. 11, 2010, and were given ATCC Patent Deposit Designations PTA-11470 and PTA-11466 by the ATCC, respectively. The deposited seeds were tested on Nov. 22, 2010 by the ATCC and, on that date, they were viable.

Certificates of Deposit have been received from the American Type Culture Collection (ATCC) for each of the deposits that are described above.

Beneficial Traits and Characteristics of Hybrids including the sh2-i Gene

The data that are present in Tables 6 and 7 (Examples 7 and 8—inbred parent sweet corn lines) and Tables 8 and 9 (Example 7—hybrid sweet corn lines), and in the other tables and figures described and illustrated herein, clearly demonstrate the greatly enhanced warm and cold laboratory and field soil germination, seedling vigor and plant strength of individual inbred parent and hybrid sweet corn seeds and varieties containing the sh2-i gene in both various double and triple allelic combinations in comparison with the same or similar inbred parent and hybrid sweet corn seeds and varieties (in both double and triple allelic combinations) that do not contain the sh2-i gene. These multiple very important and very significant advantageous sweet corn seed and plant traits and growing benefits are extremely beneficial and helpful for sweet corn growers and producers worldwide, and in many different types and climates of various geographical areas and regions employed for growing sweet corn worldwide, for example, in Northern areas or regions of various countries and/or states, such as the United States, where sweet corn growing temperatures and/or climates are often significantly cooler in comparison with Southern regions, where growing temperatures and climates are often significantly hotter, and where maintaining a uniform, consistent sweet corn stand establishment is often difficult for sweet corn producers. Sweetness and pericarp tenderness expectations of these sweet corn varieties are considered to be excellent, particularly in situations in which sweet corn products can be delivered to consumer markets within an approximately 48 hour timeframe.

In conclusion, the sweet corn seeds and varieties that are discussed and illustrated herein (including an sh2-i gene) very advantageously have numerous very advantageous and very beneficial traits in comparison with other known or other sweet corn seeds and varieties (not including the sh2-i gene):

(i) an enhanced laboratory warm germination from soil; (ii) an enhanced laboratory cold germination from soil; (iii) an enhanced germination from soil generally in the field; (iv) an enhanced seedling vigor; (v) an enhanced commercial seed production yield; (vi) an enhanced plant strength; (vii) an extended shelf life; (viii) a sweet taste while also maintaining beneficial traits (i)-(vii) and (ix); and (ix) a tender pericarp while also maintaining beneficial traits (i)-(viii). Many of these sweet corn seeds and varieties additionally and very advantageously exhibit disease resistance, for example, to northern corn leaf blight and/or to multiple races of common rust.

Further, the hybrid seeds produced according to the methods of the invention generally have a markedly different appearance from other types of corn seed. From a visual observation of the seeds, one can see the difference in their appearance from other corn seed. They do not appear to have a shrunken appearance, store starches, are generally triangular in shape.

Strategy Employed and Failure of Others

Although the shrunken-2i (sh2-i) and sugary (su1) genes are known, no one to date has been able to successfully combine these genes to produce sweet corn hybrids expressing enhanced seedling germination and vigor along with the retention of desirable consumer and/or grower traits. There has been a long-felt, but unresolved industry need for cost effective, reliable hybrids expressing an enhanced seedling germination, vigor, and plant development (like conventional sh2-i sweet corn), but with an enhanced holding ability of high sugar and tender pericarp levels both on and off the plant. Improved growth and taste characteristics of sweet corn would confer a significant advancement in the commercial production of these plants.

Various commercial plant breeders and companies, such as Syngenta Seeds Inc., which have at least "ordinary skill in the art," have attempted and failed to successfully combine traits to achieve sweet corn varieties utilizing sh2-i that is pleasing to both growers and consumers. While Syngenta has one commercial variety (named "Brighton") that includes the sh2-i allele in its genome, this product has not been commercially successful because the eating quality and, specifically, its holding ability are not desirable to consumers.

At least one other company employing plant breeders that have at least "ordinary skill in the art" also procured the sh2-i gene in a donor source from The University of Florida (as the inventor did). However, in contrast with the present inventor, this company was unable to successfully use the sh2-i gene to produce desirable sweet corn parental and hybrid lines. In contrast, the present inventor was able to incorporate the sh2-i gene very successfully into plant genomes in a manner to produce parental and hybrid line sweet corn seeds, plant materials and plants having multiple enhanced traits, such as those that are discussed hereinabove, including an enhanced growth and vigor of seeds and plants (a trait provided by the homozygous recessive sh2-i allele). The present inventor was able to accomplish this after a significant amount of experimentation and testing and a formulation and institution of a strategy to use: (i) the homozygous recessive sh2-i allele in a female parent line, and only in a female parent line (i.e., not in a male parent line), as is discussed in the "Examples" section herein (providing an enhanced growth and vigor to the seeds and plants); and (ii) homozygous recessive forms of different sweet corn alleles providing different traits to hybrids developed therefrom, such as having a sweet taste, a tender pericarp and a long shelf life (characteristics provided by other sweet corn alleles, which the present inventor used in hybrids in homozygous recessive forms along with the sh2-i gene).

Further, when the University of Florida provided a "donor source" of the sh2-i allele to its various licensees (including the present inventor and at least one unrelated company employing plant breeders), it provided the sh2-i allele in a form that is homozygous recessive for the sh2-i allele, but that was homozygous dominant (Su1Su1 Se1Se1) relative to the sugary-1 (su1) and sugary enhancer-1 (se1) mutant endosperm alleles (i.e., it had homozygous dominant forms of these two alleles). Because the sh2-i allele was homozygous recessive (sh2-i sh2-i), it provided enhanced seedling performances that are associated with the mutant sh2-i gene (which is recessive and, thus, must be homozygous recessive in order to have this trait expressed). Thus, the donor source of the sh2-i allele had the genotype Su1Su1 Se1Se1 sh2-i sh2-i. To date, none of the companies that have licensed the sh2-i allele from the University of Florida apart from the assignee of the present invention have been able to develop a commercially acceptable sweet corn hybrid variety containing the sh2-i gene for the marketplace.

Using molecular markers, the present inventor was able to determine the genotype of the donor source of the sh2-i allele. As is described in the Examples section hereof, the inventor was able to figure out that the homozygous recessive sh2-i sh2-i allele (producing the desirable seedling vigor trait, since both alleles are recessive) should be present against a genetic background of: (i) su1su1 se1se1 (a double recessive homozygous allelic combination) in a female parent line to produce a genotype of su1su1 se1se1 sh2-i sh2-i. (a triple homozygous recessive allelic combination, so that the individual beneficial traits of each of the three types of alleles were each expressed, and not masked by an inclusion of any dominant alleles); or (ii) su1su1 (single recessive homozygous alleles) in a female parent line to produce a genotype of su1su1 sh2-i sh2-i. (a double homozygous recessive allelic combination, so that the individual beneficial traits of both of the two types of alleles were each expressed, and not masked by an inclusion of any dominant alleles).

The inventor also performed various organoleptic taste and pericarp tenderness testing and discovered that unacceptable starch synthesis and buildup following the peak eating stage disallowed the process of assembling hybrids based upon the use of two sh2-i parental corn lines (i.e., with both the male and female parent lines including sh2-i alleles). The inventor subsequently determined that the best alternative was to be a generation of sweet corn hybrids comprised of an sh2-i female sweet corn line by a high-quality conventional male parental corn line.

Thus, although the University of Florida had possession of the sweet corn sh2-i allele, it did not have it (or use it) in a genotype that was homozygous recessive for all of the alleles affecting traits of sweet corn, which was determined by the present inventor to be one of the most significant aspects of making it work when used in a parent line to produce hybrid seeds, plants and plant materials having an enhanced seedling vigor and growth when crossing with another parent line having one or more different beneficial traits, such as enhanced sweetness, pericarp tenderness and/or shelf life. The inventor determined that another very important aspect was to include the sh2-i allele (in a recessive homozygous form) only in the female parent line. A further important aspect was determined to cross such a female parent line with another parent line including one or more alleles, or allelic combinations, that were all in a homozygous recessive form (i.e. triple homozygous recessive, double homozygous recessive, single homozygous recessive, or the like). In such a combination of parent lines, no dominant traits could result and mask any of the desirable recessive traits, and the recessive genotype would result in a phenotype including desired beneficial traits provided by recessive alleles. (In contrast, when either or both of the parent lines that are crossed to produce hybrids include alleles in a heterozygous form (i.e., including one dominant allele for one or more types of allele), or in a homozygous dominant form (i.e., including two dominant alleles for one or more types of alleles), the resulting phenotype of some or all of the resulting hybrid sweet corn seeds would result from the dominant alleles (i.e., not providing a beneficial trait to sweet corn hybrids developed therefrom), not from the recessive alleles (providing a beneficial trait when present in a homozygous recessive form). The dominant alleles have an effect of masking the traits of the recessive alleles, which provide the beneficial phenotypic traits.

Others who licensed the sh2-i gene from the University of Florida had the same problem that the present inventor initially had with the donor source of sh2-i allele, but were not able to figure out how to solve this problem, or to produce hybrid sweet corn seeds, plant materials or plants having the beneficial trait of an enhanced seedling vigor when using the licensed sh2-i allele. In contrast, the present inventor solved this very difficult problem using molecular markers and a variety of different tests (organoleptic taste and pericarp tenderness testing, laboratory warm and cold germination testing, field testing, seedling vigor testing and the like), as is described in the "Examples" section herein. The present inventor was able to use the sh2-i allele in a parent line in a homozygous recessive form and cross it with another parent line to produce seeds, plant materials and plants having: (i) a sweet taste (due to one or more different alleles in a homozygous recessive form); (ii) a long shelf life (due to one or more different alleles in a homozygous recessive form); and (iii) an enhanced seedling vigor (due to the sh2-i allele in a homozygous recessive form used in a female parent line), as well as the other beneficial traits that are described herein.

Further, all of the entities that licensed the sh2-i allele from The University of Florida would not expect for a licensed allele to have the problems discussed above.

While the present invention has been described herein with specificity, and with reference to certain preferred embodiments thereof, those of ordinary skill in the art will recognize numerous variations, modifications and substitutions of that which has been described which can be made, and which are within the scope and spirit of the invention. It is intended that all of these modifications and variations be within the scope of the present invention as it is described and claimed herein, and that the invention be limited only by the scope of the claims which follow, and that such claims be interpreted as broadly as is reasonable.

Throughout this document, various books, patents, journal articles, web sites and other publications have been cited. The entireties of each of these books, patents, journal articles, web sites and other publications are hereby incorporated by reference herein.

What is claimed is:

1. A method for producing a hybrid maize plant, plant material or seed that has enhanced vigor in comparison with a conventional mutant shrunken-2 hybrid maize plant, plant material or seed and one or more additional desirable traits, including an enhanced ability to retain sugar over a period of time following a prime eating stage thereof, in comparison with a conventional mutant sugary-1 or shrunken-2i hybrid maize plant, plant material or seed, comprising the following steps:
- (a) identifying an inbred maize plant line that includes one or more desired mutant endosperm alleles in its genome, singly or in combination, optionally using one or more molecular markers, wherein the mutant endosperm alleles are sugary-1 (su1), sugary enhancer-1 (se1) or shrunken-2 (sh2), or any combinations thereof;
- (b) constructing one or more female near isogenic maize plant lines having a desired genotype for use as a genetic background in a combination with a female parental maize plant line that includes a shrunken-2i (sh2-i) mutant endosperm allele in its genome;
- (c) incorporating a shrunken-2i mutant endosperm allele into the genome of the female near isogenic maize plant line having the desired genetic background of step (b), optionally using one or more molecular markers, wherein the desired genetic background is Su1Su1 se1se1, Su1Su1 se1se1 sh2sh2, Se1Se1 su1su1, Se1Se1 su1su1 sh2sh2, su1su1 se1se1, su1su1 sh2sh2, se1se1 sh2sh2, su1su1 se1se1 sh2sh2, or another desired genetic background including in homozygous recessive condition the sugary-1 and/or sugary enhancer-1 mutant endosperm alleles;
- (d) selecting a female converted near isogenic maize plant line of step (c) having a shrunken-2i mutant endosperm allele incorporated into the genetic background of step (c), wherein the female converted near isogenic maize plant line includes an endosperm allelic combination of Su1Su1 se1se1 sh2-i sh2-i, Se1Se1 su1su1 sh2-i sh2-i, su1su1 se1se1 sh2-i sh2-i, su1su1 sh2-i sh2-i, se1se1 sh2-i sh2-i, or another desirable endosperm allelic combination of the shrunken-2i mutant endosperm allele in homozygous condition together with either or both of the sugary-1 or sugary enhancer-1 mutant endosperm alleles each in homozygous condition, in its genome;

(e) crossing the selected female maize converted near isogenic plant line of step (d) with a male maize plant line that does not include a shrunken-2i mutant endosperm allele in its genome, and that includes a double homozygous recessive endosperm allelic construction in its genome, wherein such double homozygous recessive endosperm allelic construction is Su1Su1 se1se1 sh2sh2, su1su1 Se1Se1 sh2sh2, su1su1 sh2sh2, se1se1 sh2sh2, or another double homozygous recessive endosperm allelic combination including either the sugary-1 or sugary enhancer-1 mutant endosperm alleles together with the shrunken-2 mutant endosperm allele, that can provide a hybrid maize plant with a high or enhanced eating quality; to produce a hybrid maize plant comprising the allelic construction sh2 sh2-i at the shrunken-2 locus and homozygous recessive alleles at either or both of the su1 and se1 loci, said hybrid maize plant having one or more desired grower traits, consumer traits, or both traits;

(f) optionally, examining a physical appearance of seeds or kernels produced by the maize plants of step (d), step (e), or both step (d) and step (e), for characteristics including smoothness, fullness or relative weight, or a combination thereof;

(g) optionally, conducting one or more warm, cold, or both warm and cold, laboratory, field, or laboratory and field, germinations of seeds or kernels produced by the maize plants of step (d), step (e), or both step (d) and step (e), to verify that such seeds or kernels have one or more desired consumer or grower traits, or a combination thereof; and (h) optionally, conducting one or more organoleptic taste, pericarp tenderness or other tests on maize plants, or plant parts, or a combination thereof, that are grown from seeds or kernels produced by the maize plants of step (d), step (e), or both step (d) and step (e), to determine their taste, pericarp tenderness or other organoleptic characteristics, or a combination thereof;

wherein the hybrid maize plant, plant material or seed has an enhanced vigor in comparison with a conventional mutant shrunken-2 hybrid maize plant, plant material or seed; and wherein the hybrid maize plant, plant material or seed has an enhanced ability to retain sugar over a period of time following a prime eating stage thereof in comparison with a conventional mutant sugary-1 or shrunken-2i hybrid maize plant, plant material or seed.

2. A method of claim 1, wherein the selected female maize converted near isogenic plant line of step (d) includes the allelic combination su1su1 se1se1 sh2-i sh2-i, and the male maize plant line of step (e) includes the allelic combination se1se1 sh2sh2, su1su1 sh2sh2 or su1su1 Se1Se1 sh2sh2.

3. A method of claim 2, wherein one or more molecular markers are employed to incorporate the shrunken-2i mutant endosperm allele into the genome of the female maize near isogenic plant line of step (c).

4. A method of claim 1, wherein molecular markers are employed in step (a) to identify the inbred maize plant line that includes one or more desired mutant endosperm alleles in its genome.

5. A method of claim 1, wherein the female near isogenic maize plant lines of step (b) include one of the following allelic combinations:
(i) su1su1 Se1Se1 sh2sh2;
(ii) Su1Su1 se1se1 sh2sh2;
(iii) su1su1 se1se1 sh2sh2;
(iv) su1su1 se1se1; or
(v) su1su1 sh2sh2.

6. A method of claim 5, wherein the allelic combination is su1su1 se1se1 sh2sh2 or su1su1 se1se1.

7. A method of claim 5, wherein one or more molecular markers are employed in step (c) to incorporate the shrunken-2i mutant endosperm allele into the genome of the female maize near isogenic plant line having a desired genetic background.

8. A method of claim 6, wherein one or more molecular markers are employed in step (c) to incorporate the shrunken-2i mutant endosperm allele into the genome of the female maize near isogenic plant line having a desired genetic background.

9. A method of claim 7, wherein the desired genetic background of step (c) is su1su1 se1se1 sh2sh2, su1su1 se1se1, Su1Su1 se1se1 sh2sh2, or Su1Su1 se1se1.

10. A method of claim 8, wherein the desired genetic background of step (c) is su1su1 se1se1 sh2sh2, su1su1 se1se1, Su1Su1 se1se1 sh2sh2, or Su1Su1 se1se1.

11. A method of claim 5, wherein the female maize converted near isogenic plant line of step (d) is crossed with a male maize plant line including a double homozygous recessive endosperm allelic combination of su1 su1 sh2sh2, se1se1 sh2sh2 or su1su1 Se1Se1 sh2sh2 in its genome.

12. A method of claim 6, wherein the female maize converted near isogenic plant line of step (d) is crossed with a male maize plant line including a double homozygous recessive endosperm allelic combination of su1su1 sh2sh2, se1se1 sh2sh2 or su1su1 Se1Se1 sh2sh2 in its genome.

13. A method of claim 7, wherein the female maize converted near isogenic plant line of step (d) is crossed with a male maize plant line including a double homozygous recessive endosperm allelic combination of su1su1 sh2sh2, se1se1 sh2sh2 or su1su1 Se1Se1 sh2sh2 in its genome.

14. A method of claim 8, wherein the female maize converted near isogenic plant line of step (d) is crossed with a male maize plant line including a double homozygous recessive endosperm allelic combination of su1su1 sh2sh2, se1se1 sh2sh2 or su1su1 Se1Se1 sh2sh2 in its genome.

15. A method of claim 9, wherein the female maize converted near isogenic plant line of step (d) is crossed with a male maize plant line including a double homozygous recessive endosperm allelic combination of su1su1 sh2sh2, se1se1 sh2sh2 or su1su1 Se1Se1 sh2sh2 in its genome.

16. A method of claim 10, wherein the female maize converted near isogenic plant line of step (d) is crossed with a male maize plant line including a double homozygous recessive endosperm allelic combination of su1su1 sh2sh2, se1se1 sh2sh2 or su1su1 Se1Se1 sh2sh2 in its genome.

17. A method of claim 11, wherein the double homozygous recessive endosperm allelic combination in the male plant is su1su1 sh2sh2 or su1su1 Se1Se1 sh2sh2.

18. A method of claim 12, wherein the double homozygous recessive endosperm allelic combination in the male plant is su1su1 sh2sh2 or su1su1 Se1Se1 sh2sh2.

19. A method of claim 13, wherein the double homozygous recessive endosperm allelic combination in the male plant is su1su1 sh2sh2 or su1su1 Se1Se1 sh2sh2.

20. A method of claim 14, wherein the double homozygous recessive endosperm allelic combination in the male plant is su1su1 sh2sh2 or su1su1 Se1Se1 sh2sh2.

21. A method of claim 15, wherein the double homozygous recessive endosperm allelic combination in the male plant is su1su1 sh2sh2 or su1su1 Se1Se1 sh2sh2.

22. A method of claim 16, wherein the double homozygous recessive endosperm allelic combination in the male plant is su1su1 sh2sh2 or su1su1 Se1Se1 sh2sh2.

23. A method of claim 17, wherein the double homozygous recessive endosperm allelic combination in the male plant is su1su1 sh2sh2.

24. A method of claim 18, wherein the double homozygous recessive endosperm allelic combination in the male plant is su1su1 sh2sh2.

25. A method of claim 19, wherein the double homozygous recessive endosperm allelic combination in the male plant is su1su1 sh2sh2.

26. A method of claim 20, wherein the double homozygous recessive endosperm allelic combination in the male plant is su1su1 sh2sh2.

27. A method of claim 21, wherein the double homozygous recessive endosperm allelic combination in the male plant is su1su1 sh2sh2.

28. A method of claim 22, wherein the double homozygous recessive endosperm allelic combination in the male plant is su1su1 sh2sh2.

29. A method of claim 5, wherein a physical appearance of seeds or kernels produced by the plants of step (d), step (e), or both step (d) and step (e), is examined for characteristics including smoothness, fullness or relative weight, or a combination thereof.

30. A method of claim 6, wherein a physical appearance of seeds or kernels produced by the plants of step (d), step (e), or both step (d) and step (e), is examined for characteristics including smoothness, fullness or relative weight, or a combination thereof.

31. A method of claim 5, wherein warm, cold, or both warm and cold, laboratory, field, or both laboratory and field, germinations of seeds or kernels produced by the plants of step (d), step (e), or both step (d) and step (e), are conducted to verify that such seeds or kernels have an enhanced seedling germination, an enhanced seedling emergence, or an enhanced plant growth, or a combination thereof, each in comparison with a conventional mutant shrunken-2 maize plant, plant material or seed; or an enhanced ability to retain sugar over a period of time following a prime eating stage thereof, in comparison with a conventional mutant sugary-1 or shrunken-2i maize plant, plant material, or seed; or both.

32. A method of claim 6, wherein warm, cold, or both warm and cold, laboratory, field, or both laboratory and field, germinations of seeds or kernels produced by the plants of step (d), step (e), or both step (d) and step (e), are conducted to verify that such seeds or kernels have an enhanced seedling germination, an enhanced seedling emergence, or an enhanced plant growth, or a combination thereof, each in comparison with a conventional mutant shrunken-2 maize plant, plant material or seed; or an enhanced ability to retain sugar over a period of time following a prime eating stage thereof, in comparison with a conventional mutant sugary-1 or shrunken-2i maize plant, plant material, or seed; or both.

33. A method of claim 5, wherein one or more organoleptic taste, pericarp tenderness, or other tests on plants, or plant parts, that are grown from seeds or kernels produced by the plants of step (d), step (e), or both step (d) and step (e), or any combination thereof, are conducted to determine their taste, pericarp tenderness or other organoleptic characteristics, or any combination thereof.

34. A method of claim 6, wherein one or more organoleptic taste, pericarp tenderness, or other tests on plants, or plant parts, that are grown from seeds or kernels produced by the plants of step (d), step (e), or both step (d) and step (e), or any combination thereof, are conducted to determine their taste, pericarp tenderness or other organoleptic characteristics, or any combination thereof.

35. A method of claim 1, wherein the method produces an edible maize plant, plant material, seed or kernel.

36. A method of claim 35, wherein the method produces a sweet corn plant, plant material, seed or kernel.

37. A method of claim 1, wherein the hybrid maize plant, plant material or seed has an enhanced ability to retain sugar in days 1-7, days 1-14 or days 7-14 immediately following a prime eating stage thereof in comparison with a conventional mutant sugary-1 or shrunken-2i hybrid plant, plant material or seed.

38. A method of claim 35, wherein the maize plant, plant material, seed or kernel is classified as *Zea mays* var. *rugosa*.

39. A method of claim 3, wherein the hybrid maize plant, plant material or seed is classified as *Zea mays* var. *rugosa*, and has an enhanced ability to retain sugar in days 1-7, days 1-14 or days 7-14 immediately following a prime eating stage thereof in comparison with a conventional mutant sugary-1 or shrunken-2i hybrid plant, plant material or seed.

40. A method of claim 1, wherein the hybrid maize plant, plant material or seed has an enhanced ability to retain sugar in days 7-14 immediately following a prime eating stage thereof in comparison with a conventional mutant sugary-1 or shrunken-2i hybrid plant, plant material or seed.

41. A method of claim 37, wherein the hybrid maize plant, plant material or seed has an enhanced ability to retain sugar in days 7-14 immediately following a prime eating stage thereof in comparison with a conventional mutant sugary-1 or shrunken-2i hybrid plant, plant material or seed.

42. A method for producing a hybrid maize plant, plant material, or seed comprising:
   crossing an inbred maize plant line that is homozygous recessive for the shrunken-2i mutant endosperm allele and also homozygous recessive for one or both of the su1 or se1 mutant endosperm alleles as the female maize parent plant line;
   with a male maize parent plant line that does not include a shrunken-2i allele in its genome, and that is homozygous recessive for the sh2 mutant endosperm allele and one or both of the su1 or se1 mutant endosperm alleles;
   to provide a hybrid maize plant, plant material or seed with a high or an enhanced eating quality;
   wherein the hybrid maize plant, plant material or seed has an enhanced ability to retain sugar over a period of time following a prime eating stage thereof in comparison with a conventional mutant sugary-1 or shrunken-2i hybrid maize plant, plant material or seed.

43. A method of claim 42, wherein the method produces Sweet Corn Hybrid ACX SS 7501Y, representative seeds of which were deposited as ATCC Accession No. PTA-10507; Sweet Corn Hybrid ACX SS 7078Y, representative seeds of which were deposited as ATCC Accession No. PTA-10506; or Sweet Corn Hybrid ACX SS 7403RY, representative seeds of which were deposited as ATCC Accession No. PTA-10508.

44. A method for producing a hybrid maize plant, plant material or seed that has enhanced vigor in comparison with a conventional mutant shrunken-2 hybrid maize plant, plant material or seed and one or more additional desirable traits, including an enhanced ability to retain sugar over a period of time following a prime eating stage thereof, in comparison with a conventional mutant sugary-1 or shrunken-2i hybrid maize plant, plant material or seed, consisting of the following steps:
- (a) identifying an inbred maize plant line that includes one or more desired mutant endosperm alleles in its genome, singly or in combination, optionally using one or more molecular markers, wherein the mutant endosperm alleles are sugary-1 (su1), sugary enhancer-1 (se 1) or shrunken-2 (sh2), or any combinations thereof;
- (b) constructing one or more female near isogenic maize plant lines having a desired genotype for use as a genetic background in a combination with a female parental maize plant line that includes a shrunken-2i (sh2-i) mutant endosperm allele in its genome;
- (c) incorporating a shrunken-2i mutant endosperm allele into the genome of the female near isogenic maize plant line having the desired genetic background of step (b), optionally using one or more molecular markers, wherein the desired genetic background is Su1Su1 se1se1, Su1Su1 se1se1 sh2sh2, Se1Se1 su1su1, Se1Se1 su1su1 sh2sh2, su1su1 se1se1, su1su1 sh2sh2, se1se1 sh2sh2, su1su1 se1se1 sh2sh2, or another desired genetic background including in homozygous recessive condition the sugary-1 and/or sugary enhancer-1 mutant endosperm alleles;
- (d) selecting a female converted near isogenic maize plant line of step (c) having a shrunken-2i mutant endosperm allele incorporated into the genetic background of step (c), wherein the female converted near isogenic maize plant line includes an endosperm allelic combination of Su1Su1 se1se1 sh2-i sh2-i, Se1Se1 su1su1 sh2-i sh2-i, su1su1 se1se1 sh2-i sh2-i, su1su1 sh2-i sh2-i, se1se1 sh2-i sh2-i, or another desirable endosperm allelic combination of the shrunken-2i mutant endosperm allele in homozygous condition together with either or both of the sugary-1 or sugary enhancer-1 mutant endosperm alleles each in homozygous condition, in its genome;
- (e) crossing the selected female maize converted near isogenic plant line of step (d) with a male maize plant line that does not include a shrunken-2i mutant endosperm allele in its genome, and that includes a double homozygous recessive endosperm allelic construction in its genome, wherein such double homozygous recessive endosperm allelic construction is Su1Su1 se1se1 sh2sh2, su1su1 Se1Se1 sh2sh2, su1su1 sh2sh2, se1se1 sh2sh2, or another double homozygous recessive endosperm allelic combination including either the sugary-1 or sugary enhancer-1 mutant endosperm alleles together with the shrunken-2 mutant endosperm allele, that can provide a hybrid maize plant with a high or enhanced eating quality; to produce a hybrid maize plant comprising the allelic construction sh2 sh2-i at the shrunken-2 locus and homozygous recessive alleles at either or both of the su 1 and se 1 loci, said hybrid maize plant having one or more desired grower traits, consumer traits, or both traits;
- (f) optionally, examining a physical appearance of seeds or kernels produced by the maize plants of step (d), step (e), or both step (d) and step (e), for characteristics including smoothness, fullness or relative weight, or a combination thereof;
- (g) optionally, conducting one or more warm, cold, or both warm and cold, laboratory, field, or laboratory and field, germinations of seeds or kernels produced by the maize plants of step (d), step (e), or both step (d) and step (e), to verify that such seeds or kernels have one or more desired consumer or grower traits, or a combination thereof; and
- (h) optionally, conducting one or more organoleptic taste, pericarp tenderness or other tests on maize plants, or plant parts, or a combination thereof, that are grown from seeds or kernels produced by the maize plants of step (d), step (e), or both step (d) and step (e), to determine their taste, pericarp tenderness or other organoleptic characteristics, or a combination thereof;

wherein the hybrid maize plant, plant material or seed has an enhanced vigor in comparison with a conventional mutant shrunken-2 hybrid maize plant, plant material or seed; and wherein the hybrid maize plant, plant material or seed has an enhanced ability to retain sugar over a period of time following a prime eating stage thereof in comparison with a conventional mutant sugary-1 or shrunken-2i hybrid maize plant, plant material or seed.

45. A method of claim 42, wherein the female maize parent plant line includes the allelic combination su1su1 se1se1 sh2-i sh2-i, and the male maize parent plant line includes the allelic combination se1se1 sh2sh2, su1su1 sh2sh2 or su1su1 Se1Se1 sh2sh2.

46. A method of claim 45, wherein one or more molecular markers are employed to incorporate the shrunken-2i mutant endosperm allele into the genome of the female maize parent plant line.

47. A method of claim 42, wherein the female maize parent plant line includes homozygous recessive sugary-1 mutant endosperm alleles.

48. A method of claim 42, wherein the female maize parent plant line includes homozygous recessive sugary enhancer-1 mutant endosperm alleles.

49. A method of claim 42, wherein the female maize parent plant line includes a genetic background of su1su1 se1se1 in its genome.

50. A method of claim 49, wherein the female maize parent plant line includes an endosperm allelic construction of su1su1 se1se1 sh2-i sh2-i.

51. A method of claim 42, wherein the female maize parent plant line includes an endosperm allelic construction of Su1Su1 se1se1 sh2-i sh2-i or su1su1 Se1Se1 sh2-i sh2-i.

52. A method of claim 51, wherein the female maize parent line includes an endosperm allelic construction of Su1Su1 se1se1 sh2-i sh2-i.

53. A method of claim 42, wherein the male maize parent plant line includes an allelic construction including both of the sugary-1 and sugary enhancer-1 mutant endosperm alleles in homozygous condition.

54. A method of claim 42, wherein the male maize parent line includes an allelic construction of se1se1 sh2sh2, su1su1 sh2sh2 or su1su1 Se1Se1 sh2sh2.

55. A method of claim 54, wherein the male maize parent plant line includes su1su1 Se1Se1 sh2sh2 in its genome.

56. A method of claim 45 or 46, wherein the male maize parent line includes se1se1 sh2sh2, su1su1 sh2sh2 or su1su1 Se1Se1 sh2sh2 in its genome.

57. A method of claim 49, wherein the male maize parent line includes se1se1 sh2sh2, su1su1 sh2sh2 or su1su1 Se1Se1 sh2sh2 in its genome.

58. A method of claim 50, wherein the male maize parent line includes se1se1 sh2sh2, su1su1 sh2sh2 or su1su1 Se1Se1 sh2sh2 in its genome.

59. A method of claim 52, wherein the male maize parent line includes se1se1 sh2sh2, su1su1 sh2sh2 or su1su1 Se1Se1 sh2sh2 in its genome.

60. A method of claim 42, wherein the male parent line includes an allelic construction including both of the sugary-1 and sugary enhancer-1 mutant endosperm alleles in homozygous condition.

61. A method of claim 56 wherein the male maize parent plant line includes su1su1 sh2sh2 or su1su1 Se1Se1 sh2sh2 in its genome.

62. A method of claim 42, wherein the method includes the use of molecular markers to identify a maize plant that includes any of said mutant endosperm alleles in its genome.

63. A method of claim 42, wherein molecular markers are not used.

64. A method of claim 42, wherein the hybrid maize plant, plant material or seed is a sweet corn plant, plant material or seed.

65. A method of claim 56, wherein the hybrid maize plant, plant material or seed is a sweet corn plant, plant material or seed.

66. A method of claim 64, wherein the sweet corn plant, plant material or seed is classified as *Zea mays* var. *rugosa*.

67. A method of claim 65, wherein the sweet corn plant, plant material or seed is classified as *Zea mays* var. *rugosa*.

68. A method of claim 42, wherein the maize plant, plant material or seed has an enhanced ability to retain sugar in days 1-7, days 1-14 or days 7-14 immediately following a prime eating stage thereof in comparison with a conventional mutant sugary-1 or shrunken-2i maize plant, plant material or seed.

69. A method of claim 42, wherein the maize plant, plant material or seed has an enhanced vigor in comparison with a conventional mutant shrunken-2 maize plant, plant material or seed and one or more other desirable traits.

70. A maize plant produced by the method of any one of claims 1-37, 38-41, 44, 42, 46-48, 49, 50-55, 57, 58-60, 62-64, 66 and 68-69.

71. A maize plant part produced by the method of any one of claims 1-37, 38-41, 44, 42, 46-48, 49, 50-55, 57, 58-60, 62-64, 66 and 68-69.

72. A maize seed produced by the method of any one of claims 1-37, 38-41, 44, 42, 46-48, 49, 50-55, 57, 58-60, 62-64, 66 and 68-69.

73. A maize plant produced by the method of claim 45.

74. A maize plant part produced by the method of claim 45.

75. A maize seed produced by the method of claim 45.

76. A maize plant produced by the method of claim 43.

77. A maize plant part produced by the method of claim 43.

78. A maize seed produced by the method of claim 43.

79. A maize plant produced by the method of claim 61.

80. A maize plant part produced by the method of claim 61.

81. A maize seed produced by the method of claim 61.

* * * * *

SEQUENCE LISTING

```
<160> NUMBER OF SEQ ID NOS: 29

<210> SEQ ID NO 1
<211> LENGTH: 7739
<212> TYPE: DNA
<213> ORGANISM: Zea mays
<220> FEATURE:
<221> NAME/KEY: misc_feature
<223> OTHER INFORMATION: Genomic DNA
<300> PUBLICATION INFORMATION:
<302> TITLE: Mutant Genes Encoding Plant ADP-Glucose Pyrophosphorylase
      and Methods of Use
<310> PATENT DOCUMENT NUMBER: U.S. Patent No. 6,184,438 (FIG. 1)
<311> PATENT FILING DATE: 1998-11-19
<312> PUBLICATION DATE: 2001-02-06

<400> SEQUENCE: 1
taagaggggt gcacctagca tagattttt  gggctccctg gcctctcctt tcttccgcct      60
gaaaacaacc tacatggata catctgcaac cagagggagt atctgatgct tttcctggg     120 cagggagagc tatgagacgt atgtcctcaa agccactttg cattgtgtga aaccaatatc    180
gatctttgtt acttcatcat gcatgaacat ttgtggaaac tactagctta caagcattag    240
tgacagctca gaaaaagtt atctctgaaa ggtttcatgt gtaccgtggg aaatgagaaa     300
tgttgccaac tcaaacacct tcaatatgtt gtttgcaggc aaactcttct ggaagaaagg    360
tgtctaaaac tatgaacggg ttacagaaag gtataaacca cggctgtgca ttttggaagt    420
atcatctata gatgtctgtt gaggggaaag ccgtacgcca acgttattta ctcagaaaca    480
gcttcaacac acagttgtct gctttatgat ggcatctcca cccaggcacc caccatcacc    540
tattcaccta tctctcgtgc ctgtttattt tcttgccctt tctgatcata aaaaatcatt    600
aagagtttgc aaacatgcat aggcatatca atatgctcat ttattaattt gctagcagat    660
catcttccta ctctttactt tatttattgt ttgaaaaata tgtcctgcac ctagggagct    720
```

```
cgtatacagt accaatgcat cttcattaaa tgtgaatttc agaaaggaag taggaaccta    780
tgagagtatt tttcaaaatt aattagcggc ttctattatg tttatagcaa aggccaaggg    840
caaaatcgga acactaatga tggttggttg catgagtctg tcgattactt gcaagaaatg    900
tgaacctttg tttctgtgcg tgggcataaa acaaacagct tctagcctct tttacggtac    960
ttgcacttgc aagaaatgtg aactcctttt catttctgta tgtggacata atgccaaagc   1020
atccaggctt tttcatggtt gttgatgtct ttacacagtt catctccacc agtatgccct   1080
cctcatactc tatataaaca catcaacagc atcgcaatta gccacaagat cacttcggga   1140
ggcaagtgtg atttcgacct tgcagccacc ttttttttgtt ctgttgtaag tatactttcc   1200
cttaccatct ttatctgtta gtttaatttg taattgggaa gtattagtgg aaagaggatg   1260
agatgctatc atctatgtac tctgcaaatg catctgacgt tatatgggct gcttcatata   1320
atttgaattg ctccattctt gccgacaata tattgcaagg tatatgccta gttccatcaa   1380
aagttctgtt ttttcattct aaaagcattt tagtggcacg caattttgtc catgagggaa   1440
aggaaatctg ttttggttac tttgcttgag gtgcattctt catatgtcca gttttatgga   1500
agtaataaac ttcagtttgg tcataagatg tcatattaaa gggcaaacat atattcaatg   1560
ttcaattcat cgtaaatgtt ccctttttgt aaaagattgc atactcattt atttgagttg   1620
caggtgtatc tagtagttgg aggagatatg cagtttgcac ttgcattgga cacgaactca   1680
ggtcctcacc agataagatc ttgtgagggt gatgggattg acaggttgga aaaattaagt   1740
attggggggca gaaagcagga gaaagctttg agaataggt gctttggtgg tagagttgct   1800
gcaactacac aatgtattct tacctcagat gcttgtcctg aaactcttgt aagtatccac   1860
ctcaattatt actcttacat gttggtttac tttacgtttg tcttttcaag ggaaatttac   1920
tgtattttt gtgttttgtg ggagttctat acttctgttg gactggttat tgtaaagatt   1980
tgttcaaata gggtcatcta ataattgttt gaaatctggg aactgtggtt tcactgcgtt   2040
caggaaaaag tgaattattg gttactgcat gaataactta tggaaataga ccttagagtt   2100
gctgcatgat tatcacaaat cattgctacg atatcttata atagttcttt cgacctcgca   2160
ttacatatat aactgcaact cctagttgcg ttcaaaaaaa aaaatgcaac tcttagaacg   2220
ctcaccagtg taatctttcc tgaattgtta tttaatggca tgtatgcact acttgtatac   2280
ttatctagga ttaagtaatc taactctagg ccccatattt gcagcattct caaacacagt   2340
cctctaggaa aaattatgct gatgcaaacc gtgtatctgc tatcattttg ggcggaggca   2400
ctggatctca gctctttcct ctgacaagca caagagctac gcctgctgta agggataaca   2460
ctgaacatcc aacgttgatt actctattat agtattatac agactgtact tttcgaattt   2520
atcttagttt tctacaatat ttagtggatt cttctcattt tcaagataca caattgatcc   2580
ataatcgaag tggtatgtaa gacagtgagt taaaagatta tattttttgg gagacttcca   2640
gtcaaatttt cttagaagtt tttttggtcc agatgttcat aaagtcgccg ctttcatact   2700
tttttttaatt ttttaattgg tgcactatta ggtacctgtt ggaggatgtt acaggcttat   2760
tgatatccct atgagtaact gcttcaacag tggtataaat aagatatttg tgatgagtca   2820
gttcaattct acttcgctta accgccatat tcatcgtaca taccttgaag gcgggatcaa   2880
ctttgctgat ggatctgtac aggtgattta cctcatcttg ttgatgtgta atactgtaat   2940
taggagtaga tttgtgtgga gagaataata aacagatgcc gagattcttt tctaaaagtc   3000
tagatccaaa ggcattgtgg ttcaaaacac tatggacttc taccatttat gtcattactt   3060
tgccttaatg ttccattgaa tggggcaaat tattgattct acaagtgttt aattaaaaac   3120
```

```
taattgttca tcctgcaggt attagcggct acacaaatgc ctgaagagcc agctggatgg    3180
ttccagggta cagcagactc tatcagaaaa tttatctggg tactcgaggt agttgatatt    3240
ttctcgttta tgaatgtcca ttcactcatt cctgtagcat tgtttctttg taattttgag    3300
ttctcctgta tttctttagg attattacag tcacaaatcc attgacaaca ttgtaatctt    3360
gagtggcgat cagctttatc ggatgaatta catggaactt gtgcaggtat ggtgttctct    3420
tgttcctcat gtttcacgta atgtcctgat tttggattaa ccaactactt ttggcatgca    3480
ttatttccag aaacatgtcg aggacgatgc tgatatcact atatcatgtg ctcctgttga    3540
tgagaggtaa tcagttgttt atatcatcct aatatgaata tgtcatcttg ttatccaaca    3600
caggatgcat atggtctaat ctgctttcct tttttttccc ttcggaagcc gagcttctaa    3660
aaatgggcta gtgaagattg atcatactgg acgtgtactt caattctttg aaaaaccaaa    3720
gggtgctgat ttgaattcta tggttagaaa ttccttgtgt aatccaattc ttttgttttc    3780
ctttctttct tgagatgaac ccctctttta gttattccca tggataacct gtacttgact    3840
tattcagaaa tgattttcta ttttgctgta gaatctgaca ctaaagctaa tagcactgat    3900
gttgcagaga gttgagacca acttcctgag ctatgctata tgatgatgcac agaaatatcc    3960
ataccttgca tcaatgggca tttatgtctt caagaaagat gcacttttag accttctcaa    4020
gtaatcactt tcctgtgact tatttctatc caactcctag tttaccttct aacagtgtca    4080
attcttaggt caaaatatac tcaattacat gactttggat ctgaaatcct cccaagagct    4140
gtactagatc atagtgtgca ggtaagtctg atctgtctgg agtatgtgtt ctgtaaactg    4200
taaattcttc atgtcaaaaa gttgtttttg tttccagttt ccactaccaa tgcacgattt    4260
atgtattttc gcttccatgc atcatacata ctaacaatac attttacgta ttgtgttagg    4320
catgcatttt tacgggctat tgggaggatg ttggaacaat caaatcattc tttgatgcaa    4380
acttggccct cactgagcag gtactctgtc atgtattctg tactgcatat atattacctg    4440
gaattcaatg catagaatgt gttagaccat cttagttcca tcctgttttc ttcaattagc    4500
ttatcattta atagttgttg gctagaattt aaacacaaat ttacctaata tgtttctctc    4560
ttcagccttc caagtttgat ttttacgatc caaaaacacc tttcttcact gcaccccgat    4620
gcttgcctcc gacgcaattg gacaagtgca aggtatatgt cttactgagc acaattgtta    4680
cctgagcaag attttgtgta cttgacttgt tctcctccac agatgaaata tgcatttatc    4740
tcagatggtt gcttactgag agaatgcaac atcgagcatt ctgtgattgg agtctgctca    4800
cgtgtcagct ctggatgtga actcaaggta catactctgc aatgtatct actcttgagt    4860
ataccatttc aacaccaagc atcaccaaat cacacagaac aatagcaaca aagccttta    4920
gttccaagca atttagggta gcctagagtt gaaatctaac aaaacaaaag tcaaagctct    4980
atcacgtgga tagttgtttt ccatgcactc ttatttaagc taattttttg ggtatactac    5040
atccatttaa ttattgtttt attgcttctt cccctttgcct ttcccccatt actatcgcgt    5100
cttaagatca tactacgcac tagtgtcttt agaggtctct ggtggacatg ttcaaaccat    5160
ctcaatcggt gttggacaag ttttctctga atttgtgcta cacctaacct atcacgtatg    5220
tcatcgtttc aaactcgatc cttcctgtat catcataaat ccaatgcaac atcgcattt     5280
atgcaacatt tatctgttga acatgtcatc tttttgtagg ttaacattat gcaccataca    5340
atgtagcatg tctaatcatc atcctataaa atttacattt tagcttatgt ggtatcctct    5400
tgccacttag aacaccatat gcttgatgcc atttcatcca ccctgctttg attctatggc    5460
```

```
taacatcttc attaatatcc tcgcctctct gtatcattgg tcctaaatat ggaaatacat    5520
tctttctggg cactacttga ccttccaaac taacgtctcc tttgctcctt tcttgtgtgt    5580
agtagtaccg aagtcacatc tcatatattc ggttttagtt ctactaagtc ccggggttcga   5640
tcccctcag  gggtgaattt cgggcttggt aaaaaaaatc ccctcgctgt gtcccgcccg    5700
ctctcggga  tcgatatcct gcgcgccacc ctccggctgg gcattgcaga gtgagcagtt    5760
gatcggctcg ttagtgatgg ggagcggggt tcaagggttt tctcggccgg gaccatgttt    5820
cggtctctta atataatgcc gggagggcag tctttccctc cccggtcgag ttttagttct    5880
accgagtcta aaacctttgg actctagagt cccctgtcac aactcacaac tctagttttc    5940
tatttacttc tacctagcgt ttattaatga tcactatatc gtctgtaaaa agcatacacc    6000
aatgtaatcc ccttgtatgt cccttgtaat attatccatc acaagaaaaa aaggtaaggc    6060
tcaaagttga cttttgatat agtcctattc taatcgagaa gtcatctgta tcttcgtctc    6120
ttgttcgaac actagtcaca aaattttttg tacatgttct taatgagtcc aacgtaaatat   6180
tccttgatat tttgtcataa gccctcatca agtcaatgaa aatcacgtgt aggtccttca    6240
tttgttcctt atactgctcc atcacttgtc tcattaagaa aatctctctc atagttaacc    6300
ttttggcatg aaacaaaatc acacagaagt tgtttccttt ttttaagatc ccacacaaaa    6360
gaggtttgat ctaaggaatc tggatccctg acaggtttat caaaatcctt tgtgtttttc    6420
ttaaaactga atattcctcc agcttctagt attgatgtaa tattcaatct gtttagcaag    6480
tgaacacctt ggttcttgtt gttactgtac ccccccccc  cccccccccc cgaggcccag    6540
attaccacga catgaataca agaatattga acccagatct agagtttgtt tgtactgttg    6600
aaaatcggtg acaattcatt ttgttattgc gctttctgat aacgacagga ctccgtgatg    6660
atgggagcga cacctatga  aactgaagaa gaagcttcaa agctactgtt agctgggaag    6720
gtcccagttg aataggaag  gaacacaaag ataaggtgag tatggatgtg gaaccaccgg    6780
ttagttccca aaaatatcac tcactgatac ctgatggtat cctctgatta ttttcaggaa    6840
ctgtatcatt gacatgaatg ctaggattgg gaagaacgtg gtgatcacaa acagtaaggt    6900
gagcgagcgc acctacatgg gtgcagaatc ttgtgtgctc atctatccta attcggtaat    6960
tcctatccag cgctagtctt gtgaccatgg ggcatgggtt cgactctgtg acagggcatc    7020
caagaggctg atcacccgga agaagggtac tacataaggt ctggaatcgt ggtgatcttg    7080
aagaatgcaa ccatcaacga tgggtctgtc atatagatcg gctgcgtgtg cgtctacaaa    7140
acaagaacct acaatggtat tgcatcgatg gatcgtgtaa ccttggtatg gtaagagccg    7200
cttgacagaa agtcgagcgt tcgggcaaga tgcgtagtct ggcatgctgt tccttgacca    7260
tttgtgctgc tagtatgtac tgttataagc tgccctagaa gttgcagcaa acctttttat    7320
gaacctttgt atttccatta cctgctttgg atcaactata tctgtcatcc tatatattac    7380
taaattttta cgtgttttc  taattcggtg ctgcttttgg gatctggctt cgatgaccgc    7440
tcgaccctgg gccattggtt cagctctgtt ccttagagca actccaagga gtcctaaatt    7500
ttgtattaga tacgaaggac ttcagccgtg tatgtcgtcc tcaccaaacg ctcttttttgc   7560
atagtgcagg ggttgtagac ttgtagcccct tgtttaaaga ggaatttgaa tatcaaatta    7620
taagtattaa atatatattt aattaggtta acaaatttgg ctcgttttta gtctttattt     7680
atgtaattag ttttaaaaat agacctatat ttcaatacga aatatcatta acatcgata      7739
```

<210> SEQ ID NO 2
<211> LENGTH: 2712

```
<212> TYPE: DNA
<213> ORGANISM: Zea mays
<220> FEATURE:
<221> NAME/KEY: misc_feature
<223> OTHER INFORMATION: cDNA
<300> PUBLICATION INFORMATION:
<302> TITLE: Isolation of SU1, a Starch Debranching Enzyme, the Product
      of the Maize Gene Sugary1
<310> PATENT DOCUMENT NUMBER: U.S. Patent No. 5,912,413
<311> PATENT FILING DATE: 1995-03-24
<312> PUBLICATION DATE: 1999-06-15

<400> SEQUENCE: 2
cgtctcgtca cacactccac tcgaacgcac tacttgatcg gccaaagcca aacgaactgg     60
gctccctccc ctccacttcc tctccccatg gcgcagcagc tcccctgcgt ctcgtcgccg    120
cgcccgctgc tcgccgtgcc cgcgggccgg tggcgcgccg gcgtgcgggg ccggcccaat    180
gtggcgggac tggggcgggg gcggctgtct ctccacgccg ccgccgcgcg gcccgtggcc    240
gaggcggtgc aggcggagga ggacgacgac gacgacgacg aggaggtggc cgaggagagg    300
ttcgcgctgg gcggcgcgtg ccgggtgctc gcggaatgc ccgcgccgct cggcgccacc    360
gcgctccgcg gcggtgtcaa cttcgccgtc tactccagcg gtgcctccgc cgcgtcgctg    420
agcctcttcg ctcccggcga cctcaaggcg atagggtga ccgaggaggt gcccctcgat    480
cccctgctca accgaacggg aaacgtgtgg cacgtgttca tccacgggga cgagctgcac    540
ggcatgctct gcggatacag gttcgatggc gtgttcgccc tgagcgcgg acagtactac    600 gatgtgtcca acgttgtggt ggatccatac gctaaggcag tggtaagccg aggtgaatat    660
ggtgtgcctg cgcctggtgg tagttgttgg cctcaaatgg ctggtatgat ccctcttccc    720
tataataagt ttgattggca aggtgaccta ccccttgggt accatcagaa ggaccttgtc    780
atatatgaaa tgcatttgcg tggattcaca aagcacaact caagcaagac aaaacaccca    840
ggaacttaca ttggtgctgt gtcaaagctt gaccatctaa aggaacttgg agtgaactgt    900
atagagctaa tgccctgcca tgagttcaat gagctagagt acttcagctc ctcttcgaag    960
atgaacttct ggggatattc cacaataaat ttttctcac caatggcaag atattcttca   1020
agtggcataa gagactctgg atgtggtgcc ataaatgaat ttaaagcttt tgtaagggag   1080
gcccacaaac ggggaattga ggtgatcatg gatgttgtct tcaatcatac agctgaaggt   1140
aatgagaaag gcccaatatt atcctttagg gggatagata atagtacata ctacatgctt   1200
gcacctaagg gagagtttta taattattct ggttgtggaa ataccttcaa ttgtaatcat   1260
cctgtagtcc gtgaatttat agtggattgc ttgagatact gggtaacaga aatgcatgtt   1320
gatggttttc gttttgacct tgcatctata ctgaccagag gatgcagtct atgggatcca   1380
gttaatgtgt atgaagtcc aatggaaggt gacatgatta cgacagggac acctcttgtt   1440
gccccaccac ttattgacat gattagcaat gacccaattc ttggaaatgt caagctcatt   1500
gctgaagcat gggatgcagg aggtctctat caagaaggtc agtttcctca ctggaacgtt   1560
tggtcagagt ggaatggaaa gtatcgcgat accgtgcgtc agttcatcaa aggcacagat   1620
ggatttgctg gtgcttttgc tgaatgccta tgtggaagtc cacagttata ccaggcaggg   1680
gggaggaagc cttggcacag tatcggcttt gtatgtgcac acgatggatt tacactggct   1740
gatttggtca catacaatag caagtacaac ttgtcaaatg gtgaggactt cagagatggg   1800
gaaaatcata atcttagctg gaattgtggg gaggaaggag aatttgcaag tctgtcagtc   1860
cgaagattaa ggaagaggca aatgcgcaat ttctttgttt gtcttatggt ttctcaggga   1920
gttccaatgt tctacatggg cgatgaatat ggtcacacaa agggagggaa caacaatacg   1980
```

-continued

```
tactgccatg accattatgt caattatttc cgttgggata agaaggaaga acaatcctct    2040
gatttgtaca gattctgccg tctcatgacc gaattccgca aagaatgtga atctcttggc    2100
cttgaggact tcccgacttc agaacggttg aaatggcacg gtcatcagcc cgggaagcct    2160
gactggtcag aggcaagccg attcgttgcc ttcaccatga aggacgaaac caaaggcgag    2220
atctacgtgg ccttcaacac cagtcacctt ccggtggttg ttgggcttcc agagcgctct    2280
gggttccgat gggagccggt ggtggacacc ggcaaggagg caccatatga cttcctcacc    2340
gatggcctgc cagatcgtgc tgtcaccgtc taccagttct ctcatttcct caactccaat    2400
ctctatccta tgctcagcta ctcctccatc atccttgtat gcgccctga tgtctgaaag    2460 aagcagatac aatagagtat actatagcgg ttgttctcta ggctgtagca tgcagtggaa    2520 actgaaaat gttggggttg ctctgttgtc ggtagtttac atgcgcatgt cggtatgtgt    2580
acataaagct ggtggatctc agttctcaga tcggactcga gacggcaaaa ccattgccag    2640
ttggctggtt ctctgaagtt ttgtttggtg taaagaaatg gtggtccatc atctactctt    2700
tttttttttt tt                                                        2712
```

<210> SEQ ID NO 3
<211> LENGTH: 817
<212> TYPE: PRT
<213> ORGANISM: Zea mays
<300> PUBLICATION INFORMATION:
<302> TITLE: Isolation of SU1, a Starch Debranching Enzyme, the Product of the Maize Gene Sugary1
<310> PATENT DOCUMENT NUMBER: U.S. Patent No. 5,912,413
<311> PATENT FILING DATE: 1995-03-24
<312> PUBLICATION DATE: 1999-06-15

<400> SEQUENCE: 3

```
Arg Leu Val Thr His Ser Thr Arg Thr His Tyr Leu Ile Gly Gln Ser
1               5                   10                  15

Gln Thr Asn Trp Ala Pro Ser Pro Leu Pro Leu Pro Met Ala Gln
            20                  25                  30

Gln Leu Pro Cys Val Ser Ser Pro Arg Pro Leu Leu Ala Val Pro Ala
        35                  40                  45

Gly Arg Trp Arg Ala Gly Val Arg Gly Arg Pro Asn Val Ala Gly Leu
    50                  55                  60

Gly Arg Gly Arg Leu Ser Leu His Ala Ala Ala Arg Pro Val Ala
65                  70                  75                  80

Glu Ala Val Ala Glu Glu Asp Asp Asp Asp Glu Glu Val Ala
                85                  90                  95

Glu Glu Arg Phe Ala Leu Gly Gly Ala Cys Arg Val Leu Ala Gly Met
            100                 105                 110

Pro Ala Pro Leu Gly Ala Thr Ala Leu Arg Gly Gly Val Asn Phe Ala
        115                 120                 125

Val Tyr Ser Ser Gly Ala Ser Ala Ala Ser Leu Ser Leu Phe Ala Pro
    130                 135                 140

Gly Asp Leu Lys Ala Asp Arg Val Thr Glu Glu Val Pro Leu Asp Pro
145                 150                 155                 160

Leu Leu Asn Arg Thr Gly Asn Val Trp His Val Phe Ile His Gly Asp
                165                 170                 175

Glu Leu His Gly Met Leu Cys Gly Tyr Arg Phe Asp Gly Val Phe Ala
            180                 185                 190

Pro Glu Arg Gly Gln Tyr Tyr Asp Val Ser Asn Val Val Asp Pro
        195                 200                 205
```

```
Tyr Ala Lys Ala Val Val Ser Arg Gly Glu Tyr Gly Val Pro Ala Pro
            210                 215                 220

Gly Gly Ser Cys Trp Pro Gln Met Ala Gly Met Ile Pro Leu Pro Tyr
225                 230                 235                 240

Asn Lys Phe Asp Trp Gln Gly Asp Leu Pro Leu Gly Tyr His Gln Lys
                245                 250                 255

Asp Leu Val Ile Tyr Glu Met His Leu Arg Gly Phe Thr Lys His Asn
            260                 265                 270

Ser Ser Lys Thr Lys His Pro Gly Thr Tyr Ile Gly Ala Val Ser Lys
        275                 280                 285

Leu Asp His Leu Lys Glu Leu Gly Val Asn Cys Ile Glu Leu Met Pro
290                 295                 300

Cys His Glu Phe Asn Glu Leu Glu Tyr Phe Ser Ser Ser Lys Met
305                 310                 315                 320

Asn Phe Trp Gly Tyr Ser Thr Ile Asn Phe Phe Ser Pro Met Ala Arg
                325                 330                 335

Tyr Ser Ser Ser Gly Ile Arg Asp Ser Gly Cys Gly Ala Ile Asn Glu
            340                 345                 350

Phe Lys Ala Phe Val Arg Glu Ala His Lys Arg Gly Ile Glu Val Ile
        355                 360                 365

Met Asp Val Val Phe Asn His Thr Ala Glu Gly Asn Glu Lys Gly Pro
370                 375                 380

Ile Leu Ser Phe Arg Gly Ile Asp Asn Ser Thr Tyr Tyr Met Leu Ala
385                 390                 395                 400

Pro Lys Gly Glu Phe Tyr Asn Tyr Ser Gly Cys Gly Asn Thr Phe Asn
                405                 410                 415

Cys Asn His Pro Val Val Arg Glu Phe Ile Val Asp Cys Leu Arg Tyr
            420                 425                 430

Trp Val Thr Glu Met His Val Asp Gly Phe Arg Phe Asp Leu Ala Ser
        435                 440                 445

Ile Leu Thr Arg Gly Cys Ser Leu Trp Asp Pro Val Asn Val Tyr Gly
450                 455                 460

Ser Pro Met Glu Gly Asp Met Ile Thr Thr Gly Thr Pro Leu Val Ala
465                 470                 475                 480

Pro Pro Leu Ile Asp Met Ile Ser Asn Asp Pro Ile Leu Gly Asn Val
                485                 490                 495

Lys Leu Ile Ala Glu Ala Trp Asp Ala Gly Gly Leu Tyr Gln Glu Gly
            500                 505                 510

Gln Phe Pro His Trp Asn Val Trp Ser Glu Trp Asn Gly Lys Tyr Arg
        515                 520                 525

Asp Thr Val Arg Gln Phe Ile Lys Gly Thr Asp Gly Phe Ala Gly Ala
530                 535                 540

Phe Ala Glu Cys Leu Cys Gly Ser Pro Gln Leu Tyr Gln Ala Gly Gly
545                 550                 555                 560

Arg Lys Pro Trp His Ser Ile Gly Phe Val Cys Ala His Asp Gly Phe
                565                 570                 575

Thr Leu Ala Asp Leu Val Thr Tyr Asn Ser Lys Tyr Asn Leu Ser Asn
            580                 585                 590

Gly Glu Asp Phe Arg Asp Gly Glu Asn His Asn Leu Ser Trp Asn Cys
        595                 600                 605

Gly Glu Glu Gly Glu Phe Ala Ser Leu Ser Val Arg Arg Leu Arg Lys
610                 615                 620
```

```
Arg Gln Met Arg Asn Phe Phe Val Cys Leu Met Val Ser Gln Gly Val
625                 630                 635                 640

Pro Met Phe Tyr Met Gly Asp Glu Tyr Gly His Thr Lys Gly Gly Asn
                645                 650                 655

Asn Asn Thr Tyr Cys His Asp His Tyr Val Asn Tyr Phe Arg Trp Asp
                660                 665                 670

Lys Lys Glu Glu Gln Ser Ser Asp Leu Tyr Arg Phe Cys Arg Leu Met
            675                 680                 685

Thr Glu Phe Arg Lys Glu Cys Glu Ser Leu Gly Leu Glu Asp Phe Pro
        690                 695                 700

Thr Ser Glu Arg Leu Lys Trp His Gly His Gln Pro Gly Lys Pro Asp
705                 710                 715                 720

Trp Ser Glu Ala Ser Arg Phe Val Ala Phe Thr Met Lys Asp Glu Thr
                725                 730                 735

Lys Gly Glu Ile Tyr Val Ala Phe Asn Thr Ser His Leu Pro Val Val
                740                 745                 750

Val Gly Leu Pro Glu Arg Ser Gly Phe Arg Trp Glu Pro Val Val Asp
            755                 760                 765

Thr Gly Lys Glu Ala Pro Tyr Asp Phe Leu Thr Asp Gly Leu Pro Asp
        770                 775                 780

Arg Ala Val Thr Val Tyr Gln Phe Ser His Phe Leu Asn Ser Asn Leu
785                 790                 795                 800

Tyr Pro Met Leu Ser Tyr Ser Ser Ile Ile Leu Val Leu Arg Pro Asp
                805                 810                 815

Val

<210> SEQ ID NO 4
<211> LENGTH: 2523
<212> TYPE: DNA
<213> ORGANISM: Zea mays
<220> FEATURE:
<221> NAME/KEY: misc_feature
<223> OTHER INFORMATION: Genomic DNA
<300> PUBLICATION INFORMATION:
<302> TITLE: Isolation of SU1, a Starch Debranching Enzyme, the Product
      of the Maize Gene Sugary1
<310> PATENT DOCUMENT NUMBER: U.S. Patent No. 5,912,413
<311> PATENT FILING DATE: 1995-03-24
<312> PUBLICATION DATE: 1999-06-15

<400> SEQUENCE: 4
gaattctctt ttgagttaat taaccaccca caccgtacaa attgagcaag cctttgttat      60
ctccacatac atgtatatta atataagata catatatctc gttttttaaa gaaatatcgc     120
attgggttta ttattatttt aagactagtt tgtaaactct attttttctga gaaattccta    180 tttttcaaga gaaataaac taatttattt gaaaaatgt aaaacttttg ataaaatagg      240
attgtcaaac tagaccttat tatatgtata tgtatatgta taaagtatca ctgtgaaaag     300
tatgaaaaaa gtttagttct tttcttttgg tgaataaag agtataaata ataaaaagtg      360
gaatagtata gtgcctgaaa agcggcaact agatcgtgtt tgccagtacg cgggccccac    420
agaaaaagcc cacgtccgcc tcccgctgcg aaaaaacgac acgggccgag tggacgacgg    480
tggccggacg cagacgcaga cgcttccggc tgtgaaaaaa cgcacgctcc gaccccgccg    540
tccgccgatc cgaggctccg gccccactct gtcagcgtca ctgcgtgagc gagcgggcgg    600
tgtgcgtgat ccggacccgc cctcctcac accgtcgcgc acgggagcca agacgacgcc    660
gcgctccgtc gcatccacct cgtctcgtca cacactccac tcgaacgcac tacttgatcg    720
```

```
gccaaagcca aacgaactgg gctccctccc ctccacttcc tctccccatg gcgcagaagc   780
tccctgcgt ctcgtcgccg cgcccgctgc tcgccgtgcc cgcgggccgg tggcgcgccg   840
gcgtgcgggg ccggcccaat gtggcgggac tggggcgggg gcggttgtct ctccacgccg   900
ccgccgcgcg gcccgtggcc gaggcggtgc aggcggagga ggacgacgac gacgacgacg   960
aggaggtggc cgaggagagg ttcgcgctgg gcggcgcgtg ccgggtgctc gcgggaatgc  1020
ccgcgccgct cggcgccacc gcgctccgcg cggtgtcaa cttcgccgtc tactccagcg  1080
cccaccccta gtctttgatg aatgcaattt ctgcaaccgg tgctcggatc cttctgtgtc  1140
gttcttcttc tcttttggaa tttgaatgga agggaagtcg gcttactaac ttactcctct  1200
atttctctct ctctcgaata acttgcttct cgatgctgta cgctaattgt tggcttcata  1260
cgatacgccg gtgctgaaat ggactgagtt ctctgtattc ctggtatgat gcaggatagg  1320
gtgacgcagg aggtgcccct cgatccctg ctcaaccgaa cgggaaacga gaggcacgtg  1380
ttcatccacg ggaccagct gcacggcatg ctctacggat acaggttcga tgcgtgttcg  1440
cccctgagcg cggacagtac tacgatgtgt ccaacgttgt ggtggatcca tacgctaagg  1500
tgacgggctg ttgtctttac tttggctatg cgtgtgagct gtgacacact cagaaactga  1560
ttgctggggt cttgctcatg ttttagttgt ttacttcttc ttgttgttgt tttctctagg  1620
caggcagtgg taagccgagg tgaatatggt gtgcctgcgc ctggtggtag ttgttggcct  1680
caaatggctg gtatgatccc tcttccctat aataaggtaa gccagaacta ctctcgctca  1740
cactaccttc ctgtttgctt tcatgctgta tccttctctt ccagttttat gatctcccca  1800
tgtctgactc actcacgatt aaacaataaa agaaaccac cgcatatatt tggctcattg  1860
atgcatttga aaagctccgc atgaactaac tgaacaaagc gcctagaact atcaactgta  1920
ggttaggact cattggcttc tgcttactta gtttctgcct ttgccaggtt caaatggagt  1980
cgaagttata tttcacgtgc ctattatgtt gtcctgtatg ataaggttgc atttgcagtt  2040
tgattggcaa ggtgacctac ccttgggtac catcagaagg accttgtcat atatgaaatg  2100
catttgcgtg gattcacaaa gcacaactca agcaagacaa acacccagg aacttacatt  2160
ggtgctgtgt caaagcttga ccatctaaag gtactgttac gaacagacta gctataagtc  2220
tgcgaaagtg tcctcatgca tttgtttagg ttttgcaact atgccaacta tgccaagtaa  2280
tgctgcccta gtctattagt tcataggggc ataaacacag atttt actt gtgcttacat  2340
aaatgttttt tgctcagaac ttgcagtggt attggtcgtc ttagactttt tggcatgtgt  2400
ttgttgttgg aatataatat aagtgaattg tcaaccttct cctatcagct taagcttttg  2460
gatagaaaga attggttggt gcatgtaact taatatggta ttaaagacag aggtcatgaa  2520
ttc                                                               2523
```

<210> SEQ ID NO 5
<211> LENGTH: 740
<212> TYPE: PRT
<213> ORGANISM: Zea mays
<300> PUBLICATION INFORMATION:
<302> TITLE: Isolation of SU1, a Starch Debranching Enzyme, the Product
      of the Maize Gene Sugary1
<310> PATENT DOCUMENT NUMBER: U.S. Patent No. 5,912,413
<311> PATENT FILING DATE: 1995-03-24
<312> PUBLICATION DATE: 1999-06-15

<400> SEQUENCE: 5

```
Arg Pro Val Ala Glu Ala Val Gln Ala Glu Glu Asp Asp Asp Asp Asp
1               5                   10                  15
```

-continued

```
Asp Glu Glu Val Ala Glu Arg Phe Ala Leu Gly Ala Cys Arg
             20                  25                  30

Val Leu Ala Gly Met Pro Ala Pro Leu Gly Ala Thr Ala Leu Arg Gly
         35                  40                  45

Gly Val Asn Phe Ala Val Tyr Ser Ser Gly Ala Ser Ala Ala Ser Leu
     50                  55                  60

Ser Leu Phe Ala Pro Gly Asp Leu Lys Ala Asp Arg Val Thr Glu Glu
65                  70                  75                  80

Val Pro Leu Asp Pro Leu Leu Asn Arg Thr Gly Asn Val Trp His Val
                 85                  90                  95

Phe Ile His Gly Asp Glu Leu His Gly Met Leu Cys Gly Tyr Arg Phe
             100                 105                 110

Asp Gly Val Arg Ala Pro Glu Arg Gly Gln Tyr Tyr Asp Val Ser Asn
         115                 120                 125

Val Val Val Asp Pro Tyr Ala Lys Ala Val Val Ser Arg Gly Glu Tyr
     130                 135                 140

Gly Val Pro Ala Pro Gly Gly Ser Cys Trp Pro Gln Met Met Ile Pro
145                 150                 155                 160

Leu Pro Tyr Asn Lys Phe Asp Trp Gln Gly Asp Leu Pro Leu Gly Tyr
                 165                 170                 175

His Gln Lys Asp Leu Val Ile Tyr Glu Met His Leu Arg Gly Phe Thr
             180                 185                 190

Lys His Asn Ser Ser Lys Thr Lys His Pro Gly Thr Tyr Ile Gly Ala
         195                 200                 205

Val Ser Lys Leu Asp His Leu Lys Glu Leu Gly Val Asn Cys Ile Glu
     210                 215                 220

Leu Met Pro Cys His Glu Phe Asn Glu Leu Glu Tyr Phe Ser Ser Ser
225                 230                 235                 240

Ser Lys Met Asn Phe Trp Gly Tyr Ser Thr Ile Asn Phe Phe Ser Pro
                 245                 250                 255

Met Ala Arg Tyr Ser Ser Ser Gly Ile Arg Asp Ser Gly Cys Gly Ala
             260                 265                 270

Ile Asn Glu Phe Lys Ala Phe Val Arg Glu Ala His Lys Arg Gly Ile
         275                 280                 285

Glu Val Ile Met Asp Val Val Phe Asn His Thr Ala Glu Gly Asn Glu
     290                 295                 300

Lys Gly Pro Ile Leu Ser Phe Arg Gly Ile Asp Asn Ser Thr Tyr Tyr
305                 310                 315                 320

Met Leu Ala Pro Lys Gly Glu Phe Tyr Asn Tyr Ser Gly Cys Gly Asn
                 325                 330                 335

Thr Phe Asn Cys Asn His Pro Val Val Arg Glu Phe Ile Val Asp Cys
             340                 345                 350

Leu Arg Tyr Trp Val Thr Glu Met His Val Asp Gly Phe Arg Phe Asp
         355                 360                 365

Leu Ala Ser Ile Leu Thr Arg Gly Cys Ser Leu Trp Asp Pro Val Asn
     370                 375                 380

Val Tyr Gly Glu Pro Met Glu Gly Asp Met Ile Thr Thr Gly Thr Pro
385                 390                 395                 400

Leu Val Ala Pro Pro Leu Ile Asp Met Ile Ser Asn Asp Pro Ile Leu
                 405                 410                 415

Gly Asn Val Lys Leu Ile Ala Glu Ala Trp Asp Ala Gly Gly Leu Tyr
             420                 425                 430

Gln Glu Gly Gln Phe Pro His Trp His Val Trp Ser Glu Trp Asn Gly
```

```
                    435                 440                 445
Lys Tyr Arg Asp Thr Val Arg Gln Phe Ile Lys Gly Thr Asp Gly Phe
    450                 455                 460

Ala Gly Ala Phe Ala Glu Cys Leu Cys Gly Ser Pro Gln Leu Tyr Gln
465                 470                 475                 480

Ala Gly Gly Arg Lys Pro Trp His Ser Ile Gly Phe Val Cys Ala His
                485                 490                 495

Asp Gly Phe Thr Leu Ala Asp Leu Val Thr Tyr Asn Ser Lys Tyr Asn
            500                 505                 510

Leu Ser Asn Gly Glu Asp Phe Arg Asp Gly Glu Asn His Asn Leu Ser
        515                 520                 525

Trp Asn Cys Gly Glu Glu Gly Glu Phe Ala Ser Leu Ser Val Arg Arg
    530                 535                 540

Leu Arg Lys Arg Gln Met Arg Asn Phe Val Cys Leu Met Val Ser
545                 550                 555                 560

Gln Gly Val Pro Met Phe Tyr Met Gly Asp Glu Tyr Gly His Thr Lys
                565                 570                 575

Gly Gly Asn Asn Asn Thr Tyr Cys His Asp His Tyr Val Asn Tyr Phe
            580                 585                 590

Arg Trp Asp Lys Lys Glu Glu Gln Ser Ser Asp Leu Tyr Arg Phe Cys
        595                 600                 605

Arg Leu Met Thr Glu Phe Arg Lys Glu Cys Gly Ser Leu Gly Leu Glu
    610                 615                 620

Asp Phe Pro Thr Ser Glu Arg Leu Lys Trp His Gly His Gln Pro Gly
625                 630                 635                 640

Lys Pro Asp Trp Ser Glu Ala Ser Arg Phe Val Ala Phe Thr Met Lys
                645                 650                 655

Asp Glu Thr Lys Gly Glu Ile Tyr Val Ala Phe Asn Thr Ser His Leu
            660                 665                 670

Pro Val Val Val Gly Leu Pro Glu Arg Ser Gly Phe Arg Trp Glu Pro
        675                 680                 685

Val Val Asp Thr Gly Lys Glu Ala Pro Tyr Asp Phe Leu Thr Asp Gly
    690                 695                 700

Leu Pro Asp Arg Ala Val Thr Val Tyr Gln Phe Ser His Phe Leu Asn
705                 710                 715                 720

Ser Asn Leu Tyr Pro Met Leu Ser Tyr Ser Ser Ile Ile Leu Val Leu
                725                 730                 735

Thr Pro Asp Val
            740

<210> SEQ ID NO 6
<211> LENGTH: 24
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 6
caccggaaca ccttcttaca gttt                                            24

<210> SEQ ID NO 7
<211> LENGTH: 21
<212> TYPE: DNA
<213> ORGANISM: Zea mays
<220> FEATURE:
<221> NAME/KEY: misc_feature
```

<223> OTHER INFORMATION: Genomic DNA

<400> SEQUENCE: 7
cgaaaccttc tcgtgatgag c                                              21

<210> SEQ ID NO 8
<211> LENGTH: 20
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 8
tcctcttgct ctccatgtcc                                                20

<210> SEQ ID NO 9
<211> LENGTH: 20
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 9
acagctgcgt agcttcttcc                                                20

<210> SEQ ID NO 10
<211> LENGTH: 19
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 10
caactgacgc tgatggatg                                                 19

<210> SEQ ID NO 11
<211> LENGTH: 22
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 11
ttgcggtgtt aagcaattct cc                                             22

<210> SEQ ID NO 12
<211> LENGTH: 23
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 12
ctggttcgga tgcaagtagt cag                                            23

<210> SEQ ID NO 13
<211> LENGTH: 24
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 13
aaactcactg aacatgatcc tggc                                              24

<210> SEQ ID NO 14
<211> LENGTH: 24
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 14
acataaataa aacgtgtgcc gcag                                              24

<210> SEQ ID NO 15
<211> LENGTH: 23
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 15
gtacgtacgc agccacttgt cag                                               23

<210> SEQ ID NO 16
<211> LENGTH: 18
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 16
gtgcttggga caaaaagg                                                     18

<210> SEQ ID NO 17
<211> LENGTH: 18
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 17
agtccactcc agaggatg                                                     18

<210> SEQ ID NO 18
<211> LENGTH: 20
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 18
cggacgatct tatgcaaaca                                                   20

<210> SEQ ID NO 19
<211> LENGTH: 20
<212> TYPE: DNA
<213> ORGANISM: Zea mays
<220> FEATURE:
<221> NAME/KEY: misc_feature
<223> OTHER INFORMATION: Genomic DNA

```
<400> SEQUENCE: 19
acggtctgcg acaggatatt                                              20

<210> SEQ ID NO 20
<211> LENGTH: 24
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 20
ctcttcacgc tcaataaacc cagt                                         24

<210> SEQ ID NO 21
<211> LENGTH: 24
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 21
taactgcaga aacggtggtc aata                                         24

<210> SEQ ID NO 22
<211> LENGTH: 20
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 22
ccttttcatg ttgctttccc                                              20

<210> SEQ ID NO 23
<211> LENGTH: 18
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 23
gcccaatcct tccttcct                                                18

<210> SEQ ID NO 24
<211> LENGTH: 18
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 24
cagtctgcca cgaagcaa                                                18

<210> SEQ ID NO 25
<211> LENGTH: 20
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 25
```

```
ctgtcggttt cggtcttctt                                               20

<210> SEQ ID NO 26
<211> LENGTH: 24
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 26
ttcttccgcg gcttcaattt gacc                                          24

<210> SEQ ID NO 27
<211> LENGTH: 20
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 27
gcatcaggac ccgcagagtc                                               20

<210> SEQ ID NO 28
<211> LENGTH: 24
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 28
tggtgctcgt tgccaaatct acga                                          24

<210> SEQ ID NO 29
<211> LENGTH: 24
<212> TYPE: DNA
<213> ORGANISM: Zea mays
<220> FEATURE:
<221> NAME/KEY: misc_feature
<223> OTHER INFORMATION: Genomic DNA

<400> SEQUENCE: 29
gcagtggtgg tttcgaacag acaa                                          24
```